United States Patent [19]

Hogan et al.

[11] Patent Number: 6,093,538
[45] Date of Patent: Jul. 25, 2000

[54] NUCLEIC ACID PROBES TO UREAPLASMA

[75] Inventors: James J. Hogan, Coronado; Diane L. McAllister, San Diego; Patricia Gordon, Spring Valley; Philip W. Hammond, Tehachapi, all of Calif.

[73] Assignee: Gen-Probe Incorporated, San Diego, Calif.

[21] Appl. No.: 08/109,037

[22] Filed: Aug. 18, 1993

Related U.S. Application Data

[63] Continuation-in-part of application No. 07/879,686, May 6, 1992, abandoned.
[51] Int. Cl.$^7$ .............................. C12Q 1/68; C07H 21/04
[52] U.S. Cl. ........................ 435/6; 536/24.32; 536/24.33; 536/23.1
[58] Field of Search ............................. 435/6; 536/24.32, 536/24.33, 23.1; 935/878; 514/44

[56] References Cited

U.S. PATENT DOCUMENTS

| | | | |
|---|---|---|---|
| 4,851,330 | 7/1989 | Kohne | 435/6 |
| 5,030,557 | 7/1991 | Hogan | 435/6 |
| 5,185,439 | 2/1993 | Arnold et al. | 536/243 |
| 5,654,418 | 8/1997 | Sheiness et al. | 536/24.32 |
| 5,843,667 | 12/1998 | Weisburg et al. | 435/6 |

FOREIGN PATENT DOCUMENTS

| | | |
|---|---|---|
| 0250662 | 1/1988 | European Pat. Off. |
| 0281390 | 9/1988 | European Pat. Off. |
| 288618 | 11/1988 | European Pat. Off. |
| 309230 | 3/1989 | European Pat. Off. |
| 313219 | 4/1989 | European Pat. Off. |
| 0408295 | 1/1991 | European Pat. Off. |
| 8703009 | 6/1988 | WIPO . |

OTHER PUBLICATIONS

Robertson et al; J. Clin Microbiol. (1993) 31;824–830.
Rogers et al Proc Natl Acad Sci (1985) 82:1160–1164.
Van Rappeveld et al Appl Environ Microbiol (1992) 58:2606–2615.
Hammond et al. 91st General Meeting of the American Soc for Microbiol. (1991) ISSN–0067–2777, Abstract D–17.
Arnold et al Clin Chem (1989) 35:1588–1594.
Harsawa et al., "Genomic Characteristics of *Ureaplasma urealyticum*," Abstract D17, S30–6 UIMS Meeting, Osaka, Japan (1990).
Robertson et al., "Polymerase Chain Reaction Using 16S rRNA Gene Sequences Distinguishes the Two Biovars of *Ureaplasma urealyticum*," *Journal of Clinical Microbiology*31:824–830 (1993).
Brunner et al., "Quantitative Studies on the Role of *Ureaplams urealyticum* in Non–Gonococcal Urethritis and Chronic Prostatitis," *The Yale Journal of Biology and Medicine* 56:545–550 (1983).
Cassell et al., "Role of *Ureaplasma urealyticum* in amnionitis," *Pediatr. Infec. Dis.* t:S247–S252 (1986).
Stagno et al., "Infant Pneumonitis Associated with Cytomegalovirus, *Chlamydia*, *Pneumocystis*, and *Ureaplasma*: A Prospective Study," *Pediatrics*68:322–329 (1981).

Waites et al., "Chronic *Ureaplasma urealyticum* and *Mycoplasma hominis* Infections of Central Nervous System in Preterm," *The Lancet* 8575:17–21 (1988).
Lee et al., "Molecular Diagnosis of *Urealasma urealyticum* Septic Arthritis in a Patient with Hypogammaglobulineamia," *Arthritis and Rheumatism* 35:443–448 (1992).
Roberts et al., "DNA Probes for the Detection of Mycoplasmas in Genital Specimens," *Israel Journal of Medical Sciences* 23:618–620 (1987).
Ohse and Göbel, Analysis of rRNA Operons in *Ureaplasma urealyticum*, *Israel Journal of Medical Sciences* 23:352–356 (1987).
Willoughby et al., "Isolation and Detection of Urease Genes in *Ureaplasma urealyticum*," *Infection and Immunity* 59:2463–2469 (1991).
Deng et al., "Detection of PCR and Differentiation by Restriction Fragment Length Polymorphism of *Acholeplasma, Spiroplasma, Mycoplasma,* and *Ureaplasma*, Based upon 16S rRNA Genes," *PCR Methods and Applications* 1:202–204 (1992).
Brogan et al., "Development of a DNA probe for *Ureaplasma urealyticum*" *Molecular and Cellular Probes* 6:411–416 (1992).
Weisburg et al., "A Phylogenetic Analysis of the Mycoplasmas: Basis for Their Classification," *Journal of Bacteriology* 171:6455–6467 (1989).
Rogers et al., "Construction of the mycoplasma evolutionary tree from 5S rRNA sequence data," *Proc. Natl. Acad. Sci. USA* 82:1160–1164 (1985).
Southern, "Detection of Specific Sequences Among DNA Fragments Separated by Gel Electrophoresis," *J. Mol. Biol.* 98:503–517 (1975).
Arnold et al., "Assay Formats Involving Acridinium–Ester–Labeled DNA Probes," *Clinical Chemistry* 35:1588–1594 (1989).
Hammond et al., *Abstract D–16, Session 60, American Society for Microbiology Annual Meeting*, (1991).
Gonzales et al., *Abstract D–16, Session 60, American Society for Microbiology Annual Meeting*, (1991).
Stemke and Robertson, "Problems Associated with Serotyping Strains of *Ureaplasma urealyticum*," *Dian. Microbiol. Infect. Dis.* 3:311–320 (1985).
Hammond et al., 91st General Meeting of the American Society for Microbiology (1991) ISSN–0067–2777, Abstract D–17 and Poster Information.
Gonzales et al., 91st General Meeting of the American Society for Microbiology (1991) ISSN–0067–2777, Abstract D–16 and Poster Information.
Gobel et al., "Oligonucleotide probes complementary to variable regions of ribosomal RNA discriminate between Mycoplasma species," *J. General Microbiology* 133:1969–1974 (1987).

*Primary Examiner*—Carla J. Myers
*Attorney, Agent, or Firm*—Brobeck, Phleger & Harrison

[57] ABSTRACT

Hybridization assay probes are described which are able to distinguish Ureaplasma and known strains or serotypes of the species *Ureaplasma urealyticum* found in humans from other related organisms.

107 Claims, No Drawings

6,093,538

SEQUENCE LISTING (1) GENERAL INFORMATION:

(iii) NUMBER OF SEQUENCES: 141

(2) INFORMATION FOR SEQ ID NO: 1:

(i) SEQUENCE CHARACTERISTICS:
      (A) LENGTH: 28
      (B) TYPE: nucleic acid
      (C) STRANDEDNESS: single
      (D) TOPOLOGY: linear (ii) SEQUENCE DESCRIPTION: SEQ ID NO: 1:

TCATTGACTT GGTGAGCCAT TACCTCAC                                28

(2) INFORMATION FOR SEQ ID NO: 2:

(i) SEQUENCE CHARACTERISTICS:
        (A) LENGTH:          21
        (B) TYPE:            nucleic acid
        (C) STRANDEDNESS:    single
        (D) TOPOLOGY:        linear (ii) SEQUENCE DESCRIPTION: SEQ ID NO: 2:

ACCTCTCAGT ACAGCTACGC G                                       21

(2) INFORMATION FOR SEQ ID NO: 3:

(i) SEQUENCE CHARACTERISTICS:
        (A) LENGTH:          30
        (B) TYPE:            nucleic acid
        (C) STRANDEDNESS:    single
        (D) TOPOLOGY:        linear (ii) SEQUENCE DESCRIPTION: SEQ ID NO: 3:

GCCGTGTCTC AGTCCCATTG TGGCTGTTCT                              30

(2) INFORMATION FOR SEQ ID NO: 4:

(i) SEQUENCE CHARACTERISTICS:
        (A) LENGTH:          47
        (B) TYPE:            nucleic acid
        (C) STRANDEDNESS:    single
        (D) TOPOLOGY:        linear (ii) SEQUENCE DESCRIPTION: SEQ ID NO: 4:

ATATAAAGA ACTTTACAAT CTATAAGACC TTCATCGTTC ACGCGGC            47

(2) INFORMATION FOR SEQ ID NO: 5:

(i) SEQUENCE CHARACTERISTICS:
        (A) LENGTH:          26
        (B) TYPE:            nucleic acid
        (C) STRANDEDNESS:    single
        (D) TOPOLOGY:        linear (ii) SEQUENCE DESCRIPTION: SEQ ID NO: 5:

CATTTCCTAT CTTAGCGTTT CTTCCC                                  26

(2) INFORMATION FOR SEQ ID NO: 6:

(i) SEQUENCE CHARACTERISTICS:
        (A) LENGTH:          42
        (B) TYPE:            nucleic acid
        (C) STRANDEDNESS:    single
        (D) TOPOLOGY:        linear (ii) SEQUENCE DESCRIPTION: SEQ ID NO: 6:

GGCACATAGT TAGCCGATAC TTATTCAAAT GGTACAGTCA AA                42

(2) INFORMATION FOR SEQ ID NO: 7:

(i) SEQUENCE CHARACTERISTICS:
        (A) LENGTH:          38
        (B) TYPE:            nucleic acid
        (C) STRANDEDNESS:    single
        (D) TOPOLOGY:        linear (ii) SEQUENCE DESCRIPTION: SEQ ID NO: 7:

```
CCTGCGCTCG TTTTACGCCC AGTAAATCCG GATAACGC                                 38

(2) INFORMATION FOR SEQ ID NO:   8:

(i) SEQUENCE CHARACTERISTICS:
        (A) LENGTH:           39
        (B) TYPE:             nucleic acid
        (C) STRANDEDNESS:     single
        (D) TOPOLOGY:         linear (ii) SEQUENCE DESCRIPTION: SEQ ID NO: 8:

CGTTAAGCAT CTAGATTTAA TACCAAACTT ACAAACCCG                                39

(2) INFORMATION FOR SEQ ID NO:   9:

(i) SEQUENCE CHARACTERISTICS:
        (A) LENGTH:           40
        (B) TYPE:             nucleic acid
        (C) STRANDEDNESS:     single
        (D) TOPOLOGY:         linear (ii) SEQUENCE DESCRIPTION: SEQ ID NO: 9:

CCTACTACAC TCTAGGTTTA CAGTTTTTGA TACAGCTAGA                               40

(2) INFORMATION FOR SEQ ID NO:   10:

(i) SEQUENCE CHARACTERISTICS:
        (A) LENGTH:           32
        (B) TYPE:             nucleic acid
        (C) STRANDEDNESS:     single
        (D) TOPOLOGY:         linear (ii) SEQUENCE DESCRIPTION: SEQ ID NO: 10:

GCCTTCGCCA CCGGTGTTCT TCCATATATC TA                                       32

(2) INFORMATION FOR SEQ ID NO:   11:

(i) SEQUENCE CHARACTERISTICS:
        (A) LENGTH:           22
        (B) TYPE:             nucleic acid
        (C) STRANDEDNESS:     single
        (D) TOPOLOGY:         linear (ii) SEQUENCE DESCRIPTION: SEQ ID NO: 11:

GTCAGTGATA GTCCAAGTTG GC                                                  22

(2) INFORMATION FOR SEQ ID NO:   12:

(i) SEQUENCE CHARACTERISTICS:
        (A) LENGTH:           37
        (B) TYPE:             nucleic acid
        (C) STRANDEDNESS:     single
        (D) TOPOLOGY:         linear (ii) SEQUENCE DESCRIPTION: SEQ ID NO: 12:

CTAATCCTAT TTGCTCCCCA CACTTTCGAG CCTAAGC                                  37

(2) INFORMATION FOR SEQ ID NO:   13:

(i) SEQUENCE CHARACTERISTICS:
        (A) LENGTH:           25
        (B) TYPE:             nucleic acid
        (C) STRANDEDNESS:     single
        (D) TOPOLOGY:         linear (ii) SEQUENCE DESCRIPTION: SEQ ID NO: 13:
```

TTTACGGTGT GGACTACTAG GGTAT                                              25

(2) INFORMATION FOR SEQ ID NO: 14:

(i) SEQUENCE CHARACTERISTICS:
        (A) LENGTH:           28
        (B) TYPE:             nucleic acid
        (C) STRANDEDNESS:     single
        (D) TOPOLOGY:         linear (ii) SEQUENCE DESCRIPTION: SEQ ID NO: 14:

CGTTCGAGCC GACATTTAAT GATGATCG                                           28

(2) INFORMATION FOR SEQ ID NO: 15:

(i) SEQUENCE CHARACTERISTICS:
        (A) LENGTH:           21
        (B) TYPE:             nucleic acid
        (C) STRANDEDNESS:     single
        (D) TOPOLOGY:         linear (ii) SEQUENCE DESCRIPTION: SEQ ID NO: 15:

GCGTTAGCTA CAACACCGAC T                                                  21

(2) INFORMATION FOR SEQ ID NO: 16:

(i) SEQUENCE CHARACTERISTICS:
        (A) LENGTH:           46
        (B) TYPE:             nucleic acid
        (C) STRANDEDNESS:     single
        (D) TOPOLOGY:         linear (ii) SEQUENCE DESCRIPTION: SEQ ID NO: 16:

GTAAGGTTCT ACGTGTATTG TCAAATTAAG CAACATGCTC CACCAC                       46

(2) INFORMATION FOR SEQ ID NO: 17:

(i) SEQUENCE CHARACTERISTICS:
        (A) LENGTH:           25
        (B) TYPE:             nucleic acid
        (C) STRANDEDNESS:     single
        (D) TOPOLOGY:         linear (ii) SEQUENCE DESCRIPTION: SEQ ID NO: 17:

GCGTCGCAAT AGATGTCAAA CCTAG                                              25

(2) INFORMATION FOR SEQ ID NO: 18:

(i) SEQUENCE CHARACTERISTICS:
        (A) LENGTH:           39
        (B) TYPE:             nucleic acid
        (C) STRANDEDNESS:     single
        (D) TOPOLOGY:         linear (ii) SEQUENCE DESCRIPTION: SEQ ID NO: 18:

CGACAACCAT GCACCACCTG TCATATTGTT AACCTCAAC                               39

(2) INFORMATION FOR SEQ ID NO: 19:

(i) SEQUENCE CHARACTERISTICS:
        (A) LENGTH:           37
        (B) TYPE:             nucleic acid
        (C) STRANDEDNESS:     single
        (D) TOPOLOGY:         linear (ii) SEQUENCE DESCRIPTION: SEQ ID NO: 19:

TAGCACGTTT GCAGCCCTAG ATATAAGGGG CATGATG                                 37

(2) INFORMATION FOR SEQ ID NO:    20:

(i) SEQUENCE CHARACTERISTICS:
        (A) LENGTH:                    30
        (B) TYPE:                      nucleic acid
        (C) STRANDEDNESS:              single
        (D) TOPOLOGY:                  linear (ii) SEQUENCE DESCRIPTION: SEQ ID NO: 20:

CGATTTTGCA GCAGTTTGTA TTAGCCATTG                                                   30

(2) INFORMATION FOR SEQ ID NO:    21:

(i) SEQUENCE CHARACTERISTICS:
        (A) LENGTH:                    42
        (B) TYPE:                      nucleic acid
        (C) STRANDEDNESS:              single
        (D) TOPOLOGY:                  linear (ii) SEQUENCE DESCRIPTION: SEQ ID NO: 21:

CGAATTGCAG CCCTCTATCC GAACTGAGAC TAACTTTTTC TG                            42

(2) INFORMATION FOR SEQ ID NO:    22:

(i) SEQUENCE CHARACTERISTICS:
        (A) LENGTH:                    43
        (B) TYPE:                      nucleic acid
        (C) STRANDEDNESS:              single
        (D) TOPOLOGY:                  linear (ii) SEQUENCE DESCRIPTION: SEQ ID NO: 22:

GCTATTTTCG GCTCTAGAGT GCTTGACTTC TGTGTTCGGG ATG                          43

(2) INFORMATION FOR SEQ ID NO:    23:

(i) SEQUENCE CHARACTERISTICS:
        (A) LENGTH:                    30
        (B) TYPE:                      nucleic acid
        (C) STRANDEDNESS:              single
        (D) TOPOLOGY:                  linear (ii) SEQUENCE DESCRIPTION: SEQ ID NO: 23:

CGGCTCTAGA GTGCTTGACT TCTGTGTTCG                                                   30

(2) INFORMATION FOR SEQ ID NO:    24:

(i) SEQUENCE CHARACTERISTICS:
        (A) LENGTH:                    34
        (B) TYPE:                      nucleic acid
        (C) STRANDEDNESS:              single
        (D) TOPOLOGY:                  linear (ii) SEQUENCE DESCRIPTION: SEQ ID NO: 24:

GGAACAGGTA TTTCCACTCT GATATGATCA CTAC                                      34

(2) INFORMATION FOR SEQ ID NO:    25:

(i) SEQUENCE CHARACTERISTICS:
        (A) LENGTH:                    26
        (B) TYPE:                      nucleic acid
        (C) STRANDEDNESS:              single
        (D) TOPOLOGY:                  linear (ii) SEQUENCE DESCRIPTION: SEQ ID NO: 25:

GCGTAGCGAT GACCTATTTT ACTTGC                                                       26

-continued (2) INFORMATION FOR SEQ ID NO:   26:

(i) SEQUENCE CHARACTERISTICS:
        (A) LENGTH:            36
        (B) TYPE:              nucleic acid
        (C) STRANDEDNESS:      single
        (D) TOPOLOGY:          linear (ii) SEQUENCE DESCRIPTION: SEQ ID NO: 26:

GGATGGGAAC AGGTATTTCC ACTCTGATAT GATCAC                                36

(2) INFORMATION FOR SEQ ID NO:   27:

(i) SEQUENCE CHARACTERISTICS:
        (A) LENGTH:            34
        (B) TYPE:              nucleic acid
        (C) STRANDEDNESS:      single
        (D) TOPOLOGY:          linear (ii) SEQUENCE DESCRIPTION: SEQ ID NO: 27:

CGTAGCGAT GACCTATTTT ACTTGCGCTA TTTT                                   34

(2) INFORMATION FOR SEQ ID NO:   28:

(i) SEQUENCE CHARACTERISTICS:
        (A) LENGTH:            58
        (B) TYPE:              nucleic acid
        (C) STRANDEDNESS:      single
        (D) TOPOLOGY:          linear (ii) SEQUENCE DESCRIPTION: SEQ ID NO: 28:

GAGATCAACG GATTAAAGCC TCTTATCAGC TACCCGTTGC TTATCGCAGA TTAGCACG        58

(2) INFORMATION FOR SEQ ID NO:   29:

(i) SEQUENCE CHARACTERISTICS:
        (A) LENGTH:            39
        (B) TYPE:              nucleic acid
        (C) STRANDEDNESS:      single
        (D) TOPOLOGY:          linear (ii) SEQUENCE DESCRIPTION: SEQ ID NO: 29:

CAGTAATCTA ATTCTCATTA GACTGAGTTT CCTCATTCG                             39

(2) INFORMATION FOR SEQ ID NO:   30:

(i) SEQUENCE CHARACTERISTICS:
        (A) LENGTH:            44
        (B) TYPE:              nucleic acid
        (C) STRANDEDNESS:      single
        (D) TOPOLOGY:          linear (ii) SEQUENCE DESCRIPTION: SEQ ID NO: 30:

CACTTCACCA GGTATCGCTC TGTTAAACTA TGAATTCATT TATA                       44

(2) INFORMATION FOR SEQ ID NO:   31:

(i) SEQUENCE CHARACTERISTICS:
        (A) LENGTH:            21
        (B) TYPE:              nucleic acid
        (C) STRANDEDNESS:      single
        (D) TOPOLOGY:          linear (ii) SEQUENCE DESCRIPTION: SEQ ID NO: 31:

ACCUCUCAGU ACAGCUACGC G                                                21

```
(2) INFORMATION FOR SEQ ID NO:      32:

(i) SEQUENCE CHARACTERISTICS:
        (A) LENGTH:                 21
        (B) TYPE:                   nucleic acid
        (C) STRANDEDNESS:           single
        (D) TOPOLOGY:               linear (ii) SEQUENCE DESCRIPTION: SEQ ID NO: 32:

CGCGTAGCTG TACTGAGAGG T                                              21

(2) INFORMATION FOR SEQ ID NO:      33:

(i) SEQUENCE CHARACTERISTICS:
        (A) LENGTH:                 21
        (B) TYPE:                   nucleic acid
        (C) STRANDEDNESS:           single
        (D) TOPOLOGY:               linear (ii) SEQUENCE DESCRIPTION: SEQ ID NO: 33:

CGCGUAGCUG UACUGAGAGG U                                              21

(2) INFORMATION FOR SEQ ID NO:      34:

(i) SEQUENCE CHARACTERISTICS:
        (A) LENGTH:                 26
        (B) TYPE:                   nucleic acid
        (C) STRANDEDNESS:           single
        (D) TOPOLOGY:               linear (ii) SEQUENCE DESCRIPTION: SEQ ID NO: 34:

CAUUUCCUAU CUUAGCGUUU CUUCCC                                         26

(2) INFORMATION FOR SEQ ID NO:      35:

(i) SEQUENCE CHARACTERISTICS:
        (A) LENGTH:                 26
        (B) TYPE:                   nucleic acid
        (C) STRANDEDNESS:           single
        (D) TOPOLOGY:               linear (ii) SEQUENCE DESCRIPTION: SEQ ID NO: 35:

GGGAAGAAAC GCTAAGATAG GAAATG                                         26

(2) INFORMATION FOR SEQ ID NO:      36:

(i) SEQUENCE CHARACTERISTICS:
        (A) LENGTH:                 26
        (B) TYPE:                   nucleic acid
        (C) STRANDEDNESS:           single
        (D) TOPOLOGY:               linear (ii) SEQUENCE DESCRIPTION: SEQ ID NO: 36:

GGGAAGAAAC GCUAAGAUAG GAAAUG                                         26

(2) INFORMATION FOR SEQ ID NO:      37:

(i) SEQUENCE CHARACTERISTICS:
        (A) LENGTH:                 39
        (B) TYPE:                   nucleic acid
        (C) STRANDEDNESS:           single
        (D) TOPOLOGY:               linear (ii) SEQUENCE DESCRIPTION: SEQ ID NO: 37:

CGUUAAGCAU CUAGAUUUAA UACCAAACUU ACAAACCCG                           39

(2) INFORMATION FOR SEQ ID NO:      38:
```

```
        (i) SEQUENCE CHARACTERISTICS:
            (A) LENGTH:            39
            (B) TYPE:              nucleic acid
            (C) STRANDEDNESS:      single
            (D) TOPOLOGY:          linear (ii) SEQUENCE DESCRIPTION: SEQ ID NO: 38:

CGGGTTTGTA AGTTTGGTAT TAAATCTAGA TGCTTAACG                              39

(2) INFORMATION FOR SEQ ID NO:    39:

(i) SEQUENCE CHARACTERISTICS:
            (A) LENGTH:            39
            (B) TYPE:              nucleic acid
            (C) STRANDEDNESS:      single
            (D) TOPOLOGY:          linear (ii) SEQUENCE DESCRIPTION: SEQ ID NO: 39:

CGGGUUUGUA AGUUUGGUAU UAAAUCUAGA UGCUUAACG                              39

(2) INFORMATION FOR SEQ ID NO:    40:

(i) SEQUENCE CHARACTERISTICS:
            (A) LENGTH:            40
            (B) TYPE:              nucleic acid
            (C) STRANDEDNESS:      single
            (D) TOPOLOGY:          linear (ii) SEQUENCE DESCRIPTION: SEQ ID NO: 40:

CCUACUACAC UCUAGGUUUA CAGUUUUUGA UACAGCUAGA                             40

(2) INFORMATION FOR SEQ ID NO:    41:

(i) SEQUENCE CHARACTERISTICS:
            (A) LENGTH:            40
            (B) TYPE:              nucleic acid
            (C) STRANDEDNESS:      single
            (D) TOPOLOGY:          linear (ii) SEQUENCE DESCRIPTION: SEQ ID NO: 41:

TCTAGCTGTA TCAAAAACTG TAAACCTAGA GTGTAGTAGG                             40

(2) INFORMATION FOR SEQ ID NO:    42:

(i) SEQUENCE CHARACTERISTICS:
            (A) LENGTH:            40
            (B) TYPE:              nucleic acid
            (C) STRANDEDNESS:      single
            (D) TOPOLOGY:          linear (ii) SEQUENCE DESCRIPTION: SEQ ID NO: 42:

UCUAGCUGUA UCAAAAACUG UAAACCUAGA GUGUAGUAGG                             40

(2) INFORMATION FOR SEQ ID NO:    43:

(i) SEQUENCE CHARACTERISTICS:
            (A) LENGTH:            22
            (B) TYPE:              nucleic acid
            (C) STRANDEDNESS:      single
            (D) TOPOLOGY:          linear (ii) SEQUENCE DESCRIPTION: SEQ ID NO: 43:

GUCAGUGAUA GUCCAAGUUG GC                                               22

(2) INFORMATION FOR SEQ ID NO:    44:
```

```
    (i) SEQUENCE CHARACTERISTICS:
         (A) LENGTH:          22
         (B) TYPE:            nucleic acid
         (C) STRANDEDNESS:    single
         (D) TOPOLOGY:        linear (ii) SEQUENCE DESCRIPTION: SEQ ID NO: 44:

GCCAACTTGG ACTATCACTG AC                                              22

(2) INFORMATION FOR SEQ ID NO:    45:

(i) SEQUENCE CHARACTERISTICS:
         (A) LENGTH:          22
         (B) TYPE:            nucleic acid
         (C) STRANDEDNESS:    single
         (D) TOPOLOGY:        linear (ii) SEQUENCE DESCRIPTION: SEQ ID NO: 45:

GCCAACUUGG ACUAUCACUG AC                                              22

(2) INFORMATION FOR SEQ ID NO:    46:

(i) SEQUENCE CHARACTERISTICS:
         (A) LENGTH:          28
         (B) TYPE:            nucleic acid
         (C) STRANDEDNESS:    single
         (D) TOPOLOGY:        linear (ii) SEQUENCE DESCRIPTION: SEQ ID NO: 46:

CGUUCGAGCC GACAUUUAAU GAUGAUCG                                        28

(2) INFORMATION FOR SEQ ID NO:    47:

(i) SEQUENCE CHARACTERISTICS:
         (A) LENGTH:          28
         (B) TYPE:            nucleic acid
         (C) STRANDEDNESS:    single
         (D) TOPOLOGY:        linear (ii) SEQUENCE DESCRIPTION: SEQ ID NO: 47:

CGATCATCAT TAAATGTCGG CTCGAACG                                        28

(2) INFORMATION FOR SEQ ID NO:    48:

(i) SEQUENCE CHARACTERISTICS:
         (A) LENGTH:          28
         (B) TYPE:            nucleic acid
         (C) STRANDEDNESS:    single
         (D) TOPOLOGY:        linear (ii) SEQUENCE DESCRIPTION: SEQ ID NO: 48:

CGAUCAUCAU UAAAUGUCGG CUCGAACG                                        28

(2) INFORMATION FOR SEQ ID NO:    49:

(i) SEQUENCE CHARACTERISTICS:
         (A) LENGTH:          25
         (B) TYPE:            nucleic acid
         (C) STRANDEDNESS:    single
         (D) TOPOLOGY:        linear (ii) SEQUENCE DESCRIPTION: SEQ ID NO: 49:

GCGUCGCAAU AGAUGUCAAA CCUAG                                           25

(2) INFORMATION FOR SEQ ID NO:    50:

(i) SEQUENCE CHARACTERISTICS:
```

```
           (A) LENGTH:               25
           (B) TYPE:                 nucleic acid
           (C) STRANDEDNESS:         single
           (D) TOPOLOGY:             linear (ii) SEQUENCE DESCRIPTION: SEQ ID NO: 50:

CTAGGTTTGA CATCTATTGC GACGC                                              25

(2) INFORMATION FOR SEQ ID NO:   51:

(i) SEQUENCE CHARACTERISTICS:
           (A) LENGTH:               25
           (B) TYPE:                 nucleic acid
           (C) STRANDEDNESS:         single
           (D) TOPOLOGY:             linear (ii) SEQUENCE DESCRIPTION: SEQ ID NO: 51:

CUAGGUUUGA CAUCUAUUGC GACGC                                              25

(2) INFORMATION FOR SEQ ID NO:   52:

(i) SEQUENCE CHARACTERISTICS:
           (A) LENGTH:               30
           (B) TYPE:                 nucleic acid
           (C) STRANDEDNESS:         single
           (D) TOPOLOGY:             linear (ii) SEQUENCE DESCRIPTION: SEQ ID NO: 52:

CGAUUUUGCA GCAGUUUGUA UUAGCCAUUG                                         30

(2) INFORMATION FOR SEQ ID NO:   53:

(i) SEQUENCE CHARACTERISTICS:
           (A) LENGTH:               30
           (B) TYPE:                 nucleic acid
           (C) STRANDEDNESS:         single
           (D) TOPOLOGY:             linear (ii) SEQUENCE DESCRIPTION: SEQ ID NO: 53:

CAATGGCTAA TACAAACTGC TGCAAAATCG                                         30

(2) INFORMATION FOR SEQ ID NO:   54:

(i) SEQUENCE CHARACTERISTICS:
           (A) LENGTH:               30
           (B) TYPE:                 nucleic acid
           (C) STRANDEDNESS:         single
           (D) TOPOLOGY:             linear (ii) SEQUENCE DESCRIPTION: SEQ ID NO: 54:

CAAUGGCUAA UACAAACUGC UGCAAAAUCG                                         30

(2) INFORMATION FOR SEQ ID NO:   55:

(i) SEQUENCE CHARACTERISTICS:
           (A) LENGTH:               43
           (B) TYPE:                 nucleic acid
           (C) STRANDEDNESS:         single
           (D) TOPOLOGY:             linear (ii) SEQUENCE DESCRIPTION: SEQ ID NO: 55:

GCUAUUUUCG GCUCUAGAGU GCUUGACUUC UGUGUUCGGG AUG                          43

(2) INFORMATION FOR SEQ ID NO:   56:

(i) SEQUENCE CHARACTERISTICS:
           (A) LENGTH:               43
```

```
        (B) TYPE:               nucleic acid
        (C) STRANDEDNESS:       single
        (D) TOPOLOGY:           linear (ii) SEQUENCE DESCRIPTION: SEQ ID NO: 56:

CATCCCGAAC ACAGAAGTCA AGCACTCTAG AGCCGAAAAT AGC                    43

(2) INFORMATION FOR SEQ ID NO:   57:

(i) SEQUENCE CHARACTERISTICS:
        (A) LENGTH:             43
        (B) TYPE:               nucleic acid
        (C) STRANDEDNESS:       single
        (D) TOPOLOGY:           linear (ii) SEQUENCE DESCRIPTION: SEQ ID NO: 57:

CAUCCCGAAC ACAGAAGUCA AGCACUCUAG AGCCGAAAAU AGC                    43

(2) INFORMATION FOR SEQ ID NO:   58:

(i) SEQUENCE CHARACTERISTICS:
        (A) LENGTH:             30
        (B) TYPE:               nucleic acid
        (C) STRANDEDNESS:       single
        (D) TOPOLOGY:           linear (ii) SEQUENCE DESCRIPTION: SEQ ID NO: 58:

CGGCUCUAGA GUGCUUGACU UCUGUGUUCG                                   30

(2) INFORMATION FOR SEQ ID NO:   59:

(i) SEQUENCE CHARACTERISTICS:
        (A) LENGTH:             30
        (B) TYPE:               nucleic acid
        (C) STRANDEDNESS:       single
        (D) TOPOLOGY:           linear (ii) SEQUENCE DESCRIPTION: SEQ ID NO: 59:

CGAACACAGA AGTCAAGCAC TCTAGAGCCG                                   30

(2) INFORMATION FOR SEQ ID NO:   60:

(i) SEQUENCE CHARACTERISTICS:
        (A) LENGTH:             30
        (B) TYPE:               nucleic acid
        (C) STRANDEDNESS:       single
        (D) TOPOLOGY:           linear (ii) SEQUENCE DESCRIPTION: SEQ ID NO: 60:

CGAACACAGA AGUCAAGCAC UCUAGAGCCG                                   30

(2) INFORMATION FOR SEQ ID NO:   61:

(i) SEQUENCE CHARACTERISTICS:
        (A) LENGTH:             39
        (B) TYPE:               nucleic acid
        (C) STRANDEDNESS:       single
        (D) TOPOLOGY:           linear (ii) SEQUENCE DESCRIPTION: SEQ ID NO: 61:

CAGUAAUCUA AUUCUCAUUA GACUGAGUUU CCUCAUUCG                         39

(2) INFORMATION FOR SEQ ID NO:   62:

(i) SEQUENCE CHARACTERISTICS:
        (A) LENGTH:             39
        (B) TYPE:               nucleic acid
```

```
        (C) STRANDEDNESS:         single
        (D) TOPOLOGY:             linear (ii) SEQUENCE DESCRIPTION: SEQ ID NO: 62:

CGAATGAGGA AACTCAGTCT AATGAGAATT AGATTACTG                              39

(2) INFORMATION FOR SEQ ID NO:   63:

(i) SEQUENCE CHARACTERISTICS:
        (A) LENGTH:               39
        (B) TYPE:                 nucleic acid
        (C) STRANDEDNESS:         single
        (D) TOPOLOGY:             linear (ii) SEQUENCE DESCRIPTION: SEQ ID NO: 63:

CGAAUGAGGA AACUCAGUCU AAUGAGAAUU AGAUUACUG                              39

(2) INFORMATION FOR SEQ ID NO:   64:

(i) SEQUENCE CHARACTERISTICS:
        (A) LENGTH:               28
        (B) TYPE:                 nucleic acid
        (C) STRANDEDNESS:         single
        (D) TOPOLOGY:             linear (ii) SEQUENCE DESCRIPTION: SEQ ID NO: 64:

UCAUUGACUU GGUGAGCCAU UACCUCAC                                          28

(2) INFORMATION FOR SEQ ID NO:   65:

(i) SEQUENCE CHARACTERISTICS:
        (A) LENGTH:               28
        (B) TYPE:                 nucleic acid
        (C) STRANDEDNESS:         single
        (D) TOPOLOGY:             linear (ii) SEQUENCE DESCRIPTION: SEQ ID NO: 65:

GTGAGGTAAT GGCTCACCAA GTCAATGA                                          28

(2) INFORMATION FOR SEQ ID NO:   66:

(i) SEQUENCE CHARACTERISTICS:
        (A) LENGTH:               28
        (B) TYPE:                 nucleic acid
        (C) STRANDEDNESS:         single
        (D) TOPOLOGY:             linear (ii) SEQUENCE DESCRIPTION: SEQ ID NO: 66:

GUGAGGUAAU GGCUCACCAA GUCAAUGA                                          28

(2) INFORMATION FOR SEQ ID NO:   67:

(i) SEQUENCE CHARACTERISTICS:
        (A) LENGTH:               30
        (B) TYPE:                 nucleic acid
        (C) STRANDEDNESS:         single
        (D) TOPOLOGY:             linear (ii) SEQUENCE DESCRIPTION: SEQ ID NO: 67:

GCCGUGUCUC AGUCCCAUUG UGGCUGUUCU                                        30

(2) INFORMATION FOR SEQ ID NO:   68:

(i) SEQUENCE CHARACTERISTICS:
        (A) LENGTH:               30
        (B) TYPE:                 nucleic acid
        (C) STRANDEDNESS:         single
```

(D) TOPOLOGY:              linear (ii) SEQUENCE DESCRIPTION: SEQ ID NO: 68:

AGAACAGCCA CAATGGGACT GAGACACGGC                                    30

(2) INFORMATION FOR SEQ ID NO:   69:

(i) SEQUENCE CHARACTERISTICS:
        (A) LENGTH:                30
        (B) TYPE:                  nucleic acid
        (C) STRANDEDNESS:          single
        (D) TOPOLOGY:              linear (ii) SEQUENCE DESCRIPTION: SEQ ID NO: 69:

AGAACAGCCA CAAUGGGACU GAGACACGGC                                    30

(2) INFORMATION FOR SEQ ID NO:   70:

(i) SEQUENCE CHARACTERISTICS:
        (A) LENGTH:                47
        (B) TYPE:                  nucleic acid
        (C) STRANDEDNESS:          single
        (D) TOPOLOGY:              linear (ii) SEQUENCE DESCRIPTION: SEQ ID NO: 70:

AUAUAAAGA ACUUUACAAU CUAUAAGACC UUCAUCGUUC ACGCGGC                   47

(2) INFORMATION FOR SEQ ID NO:   71:

(i) SEQUENCE CHARACTERISTICS:
        (A) LENGTH:                47
        (B) TYPE:                  nucleic acid
        (C) STRANDEDNESS:          single
        (D) TOPOLOGY:              linear (ii) SEQUENCE DESCRIPTION: SEQ ID NO: 71:

GCCGCGTGAA CGATGAAGGT CTTATAGATT GTAAAGTTCT TTTATAT                  47

(2) INFORMATION FOR SEQ ID NO:   72:

(i) SEQUENCE CHARACTERISTICS:
        (A) LENGTH:                47
        (B) TYPE:                  nucleic acid
        (C) STRANDEDNESS:          single
        (D) TOPOLOGY:              linear (ii) SEQUENCE DESCRIPTION: SEQ ID NO: 72:

GCCGCGUGAA CGAUGAAGGU CUUAUAGAUU GUAAAGUUCU UUUAUAU                  47

(2) INFORMATION FOR SEQ ID NO:   73:

(i) SEQUENCE CHARACTERISTICS:
        (A) LENGTH:                42
        (B) TYPE:                  nucleic acid
        (C) STRANDEDNESS:          single
        (D) TOPOLOGY:              linear (ii) SEQUENCE DESCRIPTION: SEQ ID NO: 73:

GGCACAUAGU UAGCCGAUAC UUAUUCAAAU GGUACAGUCA AA                       42

(2) INFORMATION FOR SEQ ID NO:   74:

(i) SEQUENCE CHARACTERISTICS:
        (A) LENGTH:                42
        (B) TYPE:                  nucleic acid
        (C) STRANDEDNESS:          single
        (D) TOPOLOGY:              linear (ii) SEQUENCE DESCRIPTION: SEQ ID NO: 74:

TTTGACTGTA CCATTTGAAT AAGTATCGGC TAACTATGTG CC                42

(2) INFORMATION FOR SEQ ID NO:   75:

(i) SEQUENCE CHARACTERISTICS:
        (A) LENGTH:           42
        (B) TYPE:             nucleic acid
        (C) STRANDEDNESS:     single
        (D) TOPOLOGY:         linear (ii) SEQUENCE DESCRIPTION: SEQ ID NO: 75:

UUUGACUGUA CCAUUUGAAU AAGUAUCGGC UAACUAUGUG CC                42

(2) INFORMATION FOR SEQ ID NO:   76:

(i) SEQUENCE CHARACTERISTICS:
        (A) LENGTH:           38
        (B) TYPE:             nucleic acid
        (C) STRANDEDNESS:     single
        (D) TOPOLOGY:         linear (ii) SEQUENCE DESCRIPTION: SEQ ID NO: 76:

CCUGCGCUCG UUUUACGCCC AGUAAAUCCG GAUAACGC                     38

(2) INFORMATION FOR SEQ ID NO:   77:

(i) SEQUENCE CHARACTERISTICS:
        (A) LENGTH:           38
        (B) TYPE:             nucleic acid
        (C) STRANDEDNESS:     single
        (D) TOPOLOGY:         linear (ii) SEQUENCE DESCRIPTION: SEQ ID NO: 77:

GCGTTATCCG GATTTACTGG GCGTAAAACG AGCGCAGG                     38

(2) INFORMATION FOR SEQ ID NO:   78:

(i) SEQUENCE CHARACTERISTICS:
        (A) LENGTH:           38
        (B) TYPE:             nucleic acid
        (C) STRANDEDNESS:     single
        (D) TOPOLOGY:         linear (ii) SEQUENCE DESCRIPTION: SEQ ID NO: 78:

GCGUUAUCCG GAUUUACUGG GCGUAAAACG AGCGCAGG                     38

(2) INFORMATION FOR SEQ ID NO:   79:

(i) SEQUENCE CHARACTERISTICS:
        (A) LENGTH:           32
        (B) TYPE:             nucleic acid
        (C) STRANDEDNESS:     single
        (D) TOPOLOGY:         linear (ii) SEQUENCE DESCRIPTION: SEQ ID NO: 79:

GCCUUCGCCA CCGGUGUUCU UCCAUAUAUC UA                           32

(2) INFORMATION FOR SEQ ID NO:   80:

(i) SEQUENCE CHARACTERISTICS:
        (A) LENGTH:           32
        (B) TYPE:             nucleic acid
        (C) STRANDEDNESS:     single
        (D) TOPOLOGY:         linear (ii) SEQUENCE DESCRIPTION: SEQ ID NO: 80:

TAGATATATG GAAGAACACC GGTGGCGAAG GC                                    32

(2) INFORMATION FOR SEQ ID NO:    81:

(i) SEQUENCE CHARACTERISTICS:
        (A) LENGTH:            32
        (B) TYPE:              nucleic acid
        (C) STRANDEDNESS:      single
        (D) TOPOLOGY:          linear (ii) SEQUENCE DESCRIPTION: SEQ ID NO: 81:

UAGAUAUAUG GAAGAACACC GGUGGCGAAG GC                                    32

(2) INFORMATION FOR SEQ ID NO:    82:

(i) SEQUENCE CHARACTERISTICS:
        (A) LENGTH:            37
        (B) TYPE:              nucleic acid
        (C) STRANDEDNESS:      single
        (D) TOPOLOGY:          linear (ii) SEQUENCE DESCRIPTION: SEQ ID NO: 82:

CUAAUCCUAU UUGCUCCCCA CACUUUCGAG CCUAAGC                               37

(2) INFORMATION FOR SEQ ID NO:    83:

(i) SEQUENCE CHARACTERISTICS:
        (A) LENGTH:            37
        (B) TYPE:              nucleic acid
        (C) STRANDEDNESS:      single
        (D) TOPOLOGY:          linear (ii) SEQUENCE DESCRIPTION: SEQ ID NO: 83:

GCTTAGGCTC GAAAGTGTGG GGAGCAAATA GGATTAG                               37

(2) INFORMATION FOR SEQ ID NO:    84:

(i) SEQUENCE CHARACTERISTICS:
        (A) LENGTH:            37
        (B) TYPE:              nucleic acid
        (C) STRANDEDNESS:      single
        (D) TOPOLOGY:          linear (ii) SEQUENCE DESCRIPTION: SEQ ID NO: 84:

GCUUAGGCUC GAAAGUGUGG GGAGCAAAUA GGAUUAG                               37

(2) INFORMATION FOR SEQ ID NO:    85:

(i) SEQUENCE CHARACTERISTICS:
        (A) LENGTH:            25
        (B) TYPE:              nucleic acid
        (C) STRANDEDNESS:      single
        (D) TOPOLOGY:          linear (ii) SEQUENCE DESCRIPTION: SEQ ID NO: 85:

UUUACGGUGU GGACUACUAG GGUAU                                            25

(2) INFORMATION FOR SEQ ID NO:    86:

(i) SEQUENCE CHARACTERISTICS:
        (A) LENGTH:            25
        (B) TYPE:              nucleic acid
        (C) STRANDEDNESS:      single
        (D) TOPOLOGY:          linear (ii) SEQUENCE DESCRIPTION: SEQ ID NO: 86:

```
ATACCCTAGT AGTCCACACC GTAAA                                                    25

(2) INFORMATION FOR SEQ ID NO:     87:

(i) SEQUENCE CHARACTERISTICS:
         (A) LENGTH:              25
         (B) TYPE:                nucleic acid
         (C) STRANDEDNESS:        single
         (D) TOPOLOGY:            linear (ii) SEQUENCE DESCRIPTION: SEQ ID NO: 87:

AUACCCUAGU AGUCCACACC GUAAA                                                    25

(2) INFORMATION FOR SEQ ID NO:     88:

(i) SEQUENCE CHARACTERISTICS:
         (A) LENGTH:              21
         (B) TYPE:                nucleic acid
         (C) STRANDEDNESS:        single
         (D) TOPOLOGY:            linear (ii) SEQUENCE DESCRIPTION: SEQ ID NO: 88:

GCGUUAGCUA CAACACCGAC U                                                        21

(2) INFORMATION FOR SEQ ID NO:     89:

(i) SEQUENCE CHARACTERISTICS:
         (A) LENGTH:              21
         (B) TYPE:                nucleic acid
         (C) STRANDEDNESS:        single
         (D) TOPOLOGY:            linear (ii) SEQUENCE DESCRIPTION: SEQ ID NO: 89:

AGTCGGTGTT GTAGCTAACG C                                                        21

(2) INFORMATION FOR SEQ ID NO:     90:

(i) SEQUENCE CHARACTERISTICS:
         (A) LENGTH:              21
         (B) TYPE:                nucleic acid
         (C) STRANDEDNESS:        single
         (D) TOPOLOGY:            linear (ii) SEQUENCE DESCRIPTION: SEQ ID NO: 90:

AGUCGGUGUU GUAGCUAACG C                                                        21

(2) INFORMATION FOR SEQ ID NO:     91:

(i) SEQUENCE CHARACTERISTICS:
         (A) LENGTH:              46
         (B) TYPE:                nucleic acid
         (C) STRANDEDNESS:        single
         (D) TOPOLOGY:            linear (ii) SEQUENCE DESCRIPTION: SEQ ID NO: 91:

GUAAGGUUCU ACGUGUAUUG UCAAAUUAAG CAACAUGCUC CACCAC                              46

(2) INFORMATION FOR SEQ ID NO:     92:

(i) SEQUENCE CHARACTERISTICS:
         (A) LENGTH:              46
         (B) TYPE:                nucleic acid
         (C) STRANDEDNESS:        single
         (D) TOPOLOGY:            linear (ii) SEQUENCE DESCRIPTION: SEQ ID NO: 92:
```

GTGGTGGAGC ATGTTGCTTA ATTTGACAAT ACACGTAGAA CCTTAC        46

(2) INFORMATION FOR SEQ ID NO: 93:

(i) SEQUENCE CHARACTERISTICS:
        (A) LENGTH:           46
        (B) TYPE:             nucleic acid
        (C) STRANDEDNESS:     single
        (D) TOPOLOGY:         linear (ii) SEQUENCE DESCRIPTION: SEQ ID NO: 93:

GUGGUGGAGC AUGUUGCUUA AUUUGACAAU ACACGUAGAA CCUUAC        46

(2) INFORMATION FOR SEQ ID NO: 94:

(i) SEQUENCE CHARACTERISTICS:
        (A) LENGTH:           39
        (B) TYPE:             nucleic acid
        (C) STRANDEDNESS:     single
        (D) TOPOLOGY:         linear (ii) SEQUENCE DESCRIPTION: SEQ ID NO: 94:

CGACAACCAU GCACCACCUG UCAUAUUGUU AACCUCAAC        39

(2) INFORMATION FOR SEQ ID NO: 95:

(i) SEQUENCE CHARACTERISTICS:
        (A) LENGTH:           39
        (B) TYPE:             nucleic acid
        (C) STRANDEDNESS:     single
        (D) TOPOLOGY:         linear (ii) SEQUENCE DESCRIPTION: SEQ ID NO: 95:

GTTGAGGTTA ACAATATGAC AGGTGGTGCA TGGTTGTCG        39

(2) INFORMATION FOR SEQ ID NO: 96:

(i) SEQUENCE CHARACTERISTICS:
        (A) LENGTH:           39
        (B) TYPE:             nucleic acid
        (C) STRANDEDNESS:     single
        (D) TOPOLOGY:         linear (ii) SEQUENCE DESCRIPTION: SEQ ID NO: 96:

GUUGAGGUUA ACAAUAUGAC AGGUGGUGCA UGGUUGUCG        39

(2) INFORMATION FOR SEQ ID NO: 97:

(i) SEQUENCE CHARACTERISTICS:
        (A) LENGTH:           37
        (B) TYPE:             nucleic acid
        (C) STRANDEDNESS:     single
        (D) TOPOLOGY:         linear (ii) SEQUENCE DESCRIPTION: SEQ ID NO: 97:

UAGCACGUUU GCAGCCCUAG AUAUAAGGGG CAUGAUG        37

(2) INFORMATION FOR SEQ ID NO: 98:

(i) SEQUENCE CHARACTERISTICS:
        (A) LENGTH:           37
        (B) TYPE:             nucleic acid
        (C) STRANDEDNESS:     single
        (D) TOPOLOGY:         linear (ii) SEQUENCE DESCRIPTION: SEQ ID NO: 98:

CATCATGCCC CTTATATCTA GGGCTGCAAA CGTGCTA        37

(2) INFORMATION FOR SEQ ID NO:    99:

(i) SEQUENCE CHARACTERISTICS:
        (A) LENGTH:          37
        (B) TYPE:            nucleic acid
        (C) STRANDEDNESS:    single
        (D) TOPOLOGY:        linear (ii) SEQUENCE DESCRIPTION: SEQ ID NO: 99:

CAUCAUGCCC CUUAUAUCUA GGGCUGCAAA CGUGCUA                    37

(2) INFORMATION FOR SEQ ID NO:    100:

(i) SEQUENCE CHARACTERISTICS:
        (A) LENGTH:          42
        (B) TYPE:            nucleic acid
        (C) STRANDEDNESS:    single
        (D) TOPOLOGY:        linear (ii) SEQUENCE DESCRIPTION: SEQ ID NO: 100:

CGAAUUGCAG CCCUCUAUCC GAACUGAGAC UAACUUUUUC UG            42

(2) INFORMATION FOR SEQ ID NO:    101:

(i) SEQUENCE CHARACTERISTICS:
        (A) LENGTH:          42
        (B) TYPE:            nucleic acid
        (C) STRANDEDNESS:    single
        (D) TOPOLOGY:        linear (ii) SEQUENCE DESCRIPTION: SEQ ID NO: 101:

CAGAAAAGT TAGTCTCAGT TCGGATAGAG GGCTGCAATT CG             42

(2) INFORMATION FOR SEQ ID NO:    102:

(i) SEQUENCE CHARACTERISTICS:
        (A) LENGTH:          42
        (B) TYPE:            nucleic acid
        (C) STRANDEDNESS:    single
        (D) TOPOLOGY:        linear (ii) SEQUENCE DESCRIPTION: SEQ ID NO: 102:

CAGAAAAAGU UAGUCUCAGU UCGGAUAGAG GGCUGCAAUU CG            42

(2) INFORMATION FOR SEQ ID NO:    103:

(i) SEQUENCE CHARACTERISTICS:
        (A) LENGTH:          34
        (B) TYPE:            nucleic acid
        (C) STRANDEDNESS:    single
        (D) TOPOLOGY:        linear (ii) SEQUENCE DESCRIPTION: SEQ ID NO: 103:

GGAACAGGUA UUUCCACUCU GAUAUGAUCA CUAC                      34

(2) INFORMATION FOR SEQ ID NO:    104:

(i) SEQUENCE CHARACTERISTICS:
        (A) LENGTH:          34
        (B) TYPE:            nucleic acid
        (C) STRANDEDNESS:    single
        (D) TOPOLOGY:        linear (ii) SEQUENCE DESCRIPTION: SEQ ID NO: 104:

GTAGTGATCA TATCAGAGTG GAAATACCTG TTCC                      34

(2) INFORMATION FOR SEQ ID NO: 105:

(i) SEQUENCE CHARACTERISTICS:
        (A) LENGTH:         34
        (B) TYPE:           nucleic acid
        (C) STRANDEDNESS:  single
        (D) TOPOLOGY:      linear (ii) SEQUENCE DESCRIPTION: SEQ ID NO: 105:

GUAGUGAUCA UAUCAGAGUG GAAAUACCUG UUCC                      34

(2) INFORMATION FOR SEQ ID NO: 106:

(i) SEQUENCE CHARACTERISTICS:
        (A) LENGTH:         26
        (B) TYPE:           nucleic acid
        (C) STRANDEDNESS:  single
        (D) TOPOLOGY:      linear (ii) SEQUENCE DESCRIPTION: SEQ ID NO: 106:

GCGUAGCGAU GACCUAUUUU ACUUGC                                26

(2) INFORMATION FOR SEQ ID NO: 107:

(i) SEQUENCE CHARACTERISTICS:
        (A) LENGTH:         26
        (B) TYPE:           nucleic acid
        (C) STRANDEDNESS:  single
        (D) TOPOLOGY:      linear (ii) SEQUENCE DESCRIPTION: SEQ ID NO: 107:

GCAAGTAAAA TAGGTCATCG CTACGC                                26

(2) INFORMATION FOR SEQ ID NO: 108:

(i) SEQUENCE CHARACTERISTICS:
        (A) LENGTH:         26
        (B) TYPE:           nucleic acid
        (C) STRANDEDNESS:  single
        (D) TOPOLOGY:      linear (ii) SEQUENCE DESCRIPTION: SEQ ID NO: 108:

GCAAGUAAAA UAGGUCAUCG CUACGC                                26

(2) INFORMATION FOR SEQ ID NO: 109:

(i) SEQUENCE CHARACTERISTICS:
        (A) LENGTH:         36
        (B) TYPE:           nucleic acid
        (C) STRANDEDNESS:  single
        (D) TOPOLOGY:      linear (ii) SEQUENCE DESCRIPTION: SEQ ID NO: 109:

GGAUGGGAAC AGGUAUUUCC ACUCUGAUAU GAUCAC                    36

(2) INFORMATION FOR SEQ ID NO: 110:

(i) SEQUENCE CHARACTERISTICS:
        (A) LENGTH:         36
        (B) TYPE:           nucleic acid
        (C) STRANDEDNESS:  single
        (D) TOPOLOGY:      linear (ii) SEQUENCE DESCRIPTION: SEQ ID NO: 110:

GTGATCATAT CAGAGTGGAA ATACCTGTTC CCATCC                    36

(2) INFORMATION FOR SEQ ID NO: 111:

(i) SEQUENCE CHARACTERISTICS:
        (A) LENGTH:        36
        (B) TYPE:          nucleic acid
        (C) STRANDEDNESS:  single
        (D) TOPOLOGY:     linear (ii) SEQUENCE DESCRIPTION: SEQ ID NO: 111:

GUGAUCAUAU CAGAGUGGAA AUACCUGUUC CCAUCC                    36

(2) INFORMATION FOR SEQ ID NO: 112:

(i) SEQUENCE CHARACTERISTICS:
        (A) LENGTH:        34
        (B) TYPE:          nucleic acid
        (C) STRANDEDNESS:  single
        (D) TOPOLOGY:     linear (ii) SEQUENCE DESCRIPTION: SEQ ID NO: 112:

GCGUAGCGAU GACCUAUUUU ACUUGCGCUA UUUU                      34

(2) INFORMATION FOR SEQ ID NO: 113:

(i) SEQUENCE CHARACTERISTICS:
        (A) LENGTH:        34
        (B) TYPE:          nucleic acid
        (C) STRANDEDNESS:  single
        (D) TOPOLOGY:     linear (ii) SEQUENCE DESCRIPTION: SEQ ID NO: 113:

AAAATAGCGC AAGTAAAATA GGTCATCGCT ACGC                      34

(2) INFORMATION FOR SEQ ID NO: 114:

(i) SEQUENCE CHARACTERISTICS:
        (A) LENGTH:        34
        (B) TYPE:          nucleic acid
        (C) STRANDEDNESS:  single
        (D) TOPOLOGY:     linear (ii) SEQUENCE DESCRIPTION: SEQ ID NO: 114:

AAAAUAGCGC AAGUAAAAUA GGUCAUCGCU ACGC                      34

(2) INFORMATION FOR SEQ ID NO: 115:

(i) SEQUENCE CHARACTERISTICS:
        (A) LENGTH:        58
        (B) TYPE:          nucleic acid
        (C) STRANDEDNESS:  single
        (D) TOPOLOGY:     linear (ii) SEQUENCE DESCRIPTION: SEQ ID NO: 115:

GAGAUCAACG GAUUAAAGCC UCUUAUCAGC UACCCGUUGC UUAUCGCAGA UUAGCACG      58

(2) INFORMATION FOR SEQ ID NO: 116:

(i) SEQUENCE CHARACTERISTICS:
        (A) LENGTH:        58
        (B) TYPE:          nucleic acid
        (C) STRANDEDNESS:  single
        (D) TOPOLOGY:     linear (ii) SEQUENCE DESCRIPTION: SEQ ID NO: 116:

CGTGCTAATC TGCGATAAGC AACGGGTAGC TGATAAGAGG CTTTAATCCG TTGATCTC      58

(2) INFORMATION FOR SEQ ID NO: 117:

(i) SEQUENCE CHARACTERISTICS:
           (A) LENGTH:           58
           (B) TYPE:             nucleic acid
           (C) STRANDEDNESS:     single
           (D) TOPOLOGY:         linear (ii) SEQUENCE DESCRIPTION: SEQ ID NO: 117:

CGUGCUAAUC UGCGAUAAGC AACGGGUAGC UGAUAAGAGG CUUUAAUCCG UUGAUCUC        58

(2) INFORMATION FOR SEQ ID NO:    118:

(i) SEQUENCE CHARACTERISTICS:
           (A) LENGTH:           44
           (B) TYPE:             nucleic acid
           (C) STRANDEDNESS:     single
           (D) TOPOLOGY:         linear (ii) SEQUENCE DESCRIPTION: SEQ ID NO: 118:

CACUUCACCA GGUAUCGCUC UGUUAAACUA UGAAUUCAUU UAUA                       44

(2) INFORMATION FOR SEQ ID NO:    119:

(i) SEQUENCE CHARACTERISTICS:
           (A) LENGTH:           44
           (B) TYPE:             nucleic acid
           (C) STRANDEDNESS:     single
           (D) TOPOLOGY:         linear (ii) SEQUENCE DESCRIPTION: SEQ ID NO: 119:

TATAAATGAA TTCATAGTTT AACAGAGCGA TACCTGGTGA AGTG                       44

(2) INFORMATION FOR SEQ ID NO:    120:

(i) SEQUENCE CHARACTERISTICS:
           (A) LENGTH:           44
           (B) TYPE:             nucleic acid
           (C) STRANDEDNESS:     single
           (D) TOPOLOGY:         linear (ii) SEQUENCE DESCRIPTION: SEQ ID NO: 120:

UAUAAAUGAA UUCAUAGUUU AACAGAGCGA UACCUGGUGA AGUG                       44

(2) INFORMATION FOR SEQ ID NO:    121:

(i) SEQUENCE CHARACTERISTICS:
           (A) LENGTH:           20
           (B) TYPE:             nucleic acid
           (C) STRANDEDNESS:     single
           (D) TOPOLOGY:         linear (ii) SEQUENCE DESCRIPTION: SEQ ID NO: 121:

CAACACCGAC TCGTTCGAGC                                                  20

(2) INFORMATION FOR SEQ ID NO:    122:

(i) SEQUENCE CHARACTERISTICS:
           (A) LENGTH:           18
           (B) TYPE:             nucleic acid
           (C) STRANDEDNESS:     single
           (D) TOPOLOGY:         linear (ii) SEQUENCE DESCRIPTION: SEQ ID NO: 122:

CAACACCGAC CCATTCGG                                                    18

(2) INFORMATION FOR SEQ ID NO:    123:

```
    (i) SEQUENCE CHARACTERISTICS:
         (A) LENGTH:            33
         (B) TYPE:              nucleic acid
         (C) STRANDEDNESS:      single
         (D) TOPOLOGY:          linear (ii) SEQUENCE DESCRIPTION: SEQ ID NO: 123:

CGACATTTAA TGATGATCGT TTACGGTGTG GAC                                33

(2) INFORMATION FOR SEQ ID NO:  124:

(i) SEQUENCE CHARACTERISTICS:
         (A) LENGTH:            35
         (B) TYPE:              nucleic acid
         (C) STRANDEDNESS:      single
         (D) TOPOLOGY:          linear (ii) SEQUENCE DESCRIPTION: SEQ ID NO: 124:

GCCGACATTT AATGATGATC GTTTACGGTG TGGAC                              35

(2) INFORMATION FOR SEQ ID NO:  125:

(i) SEQUENCE CHARACTERISTICS:
         (A) LENGTH:            29
         (B) TYPE:              nucleic acid
         (C) STRANDEDNESS:      single
         (D) TOPOLOGY:          linear (ii) SEQUENCE DESCRIPTION: SEQ ID NO: 125:

CCCAGGCACA TCATTTAATG CGTTAGCTA                                     29

(2) INFORMATION FOR SEQ ID NO:  126:

(i) SEQUENCE CHARACTERISTICS:
         (A) LENGTH:            20
         (B) TYPE:              nucleic acid
         (C) STRANDEDNESS:      single
         (D) TOPOLOGY:          linear (ii) SEQUENCE DESCRIPTION: SEQ ID NO: 126:

CAACACCGAC UCGUUCGAGC                                               20

(2) INFORMATION FOR SEQ ID NO:  127:

(i) SEQUENCE CHARACTERISTICS:
         (A) LENGTH:            18
         (B) TYPE:              nucleic acid
         (C) STRANDEDNESS:      single
         (D) TOPOLOGY:          linear (ii) SEQUENCE DESCRIPTION: SEQ ID NO: 127:

CAACACCGAC CCAUUCGG                                                 18

(2) INFORMATION FOR SEQ ID NO:  128:

(i) SEQUENCE CHARACTERISTICS:
         (A) LENGTH:            33
         (B) TYPE:              nucleic acid
         (C) STRANDEDNESS:      single
         (D) TOPOLOGY:          linear (ii) SEQUENCE DESCRIPTION: SEQ ID NO: 128:

CGACAUUUAA UGAUGAUCGU UUACGGUGUG GAC                                33

(2) INFORMATION FOR SEQ ID NO:  129:

(i) SEQUENCE CHARACTERISTICS:
```

```
            (A) LENGTH:              35
            (B) TYPE:                nucleic acid
            (C) STRANDEDNESS:        single
            (D) TOPOLOGY:            linear (ii) SEQUENCE DESCRIPTION: SEQ ID NO: 129:

GCCGACAUUU AAUGAUGAUC GUUUACGGUG UGGAC                              35

(2) INFORMATION FOR SEQ ID NO:    130:

(i) SEQUENCE CHARACTERISTICS:
            (A) LENGTH:              29
            (B) TYPE:                nucleic acid
            (C) STRANDEDNESS:        single
            (D) TOPOLOGY:            linear (ii) SEQUENCE DESCRIPTION: SEQ ID NO: 130:

CCCAGGCACA UCAUUUAAUG CGUUAGCUA                                     29

(2) INFORMATION FOR SEQ ID NO:    131:

(i) SEQUENCE CHARACTERISTICS:
            (A) LENGTH:              20
            (B) TYPE:                nucleic acid
            (C) STRANDEDNESS:        single
            (D) TOPOLOGY:            linear (ii) SEQUENCE DESCRIPTION: SEQ ID NO: 131:

GCTCGAACGA GTCGGTGTTG                                               20

(2) INFORMATION FOR SEQ ID NO:    132:

(i) SEQUENCE CHARACTERISTICS:
            (A) LENGTH:              18
            (B) TYPE:                nucleic acid
            (C) STRANDEDNESS:        single
            (D) TOPOLOGY:            linear (ii) SEQUENCE DESCRIPTION: SEQ ID NO: 132:

CCGAATGGGT CGGTGTTG                                                 18

(2) INFORMATION FOR SEQ ID NO:    133:

(i) SEQUENCE CHARACTERISTICS:
            (A) LENGTH:              33
            (B) TYPE:                nucleic acid
            (C) STRANDEDNESS:        single
            (D) TOPOLOGY:            linear (ii) SEQUENCE DESCRIPTION: SEQ ID NO: 133:

GTCCACACCG TAAACGATCA TCATTAAATG TCG                                33

(2) INFORMATION FOR SEQ ID NO:    134:

(i) SEQUENCE CHARACTERISTICS:
            (A) LENGTH:              35
            (B) TYPE:                nucleic acid
            (C) STRANDEDNESS:        single
            (D) TOPOLOGY:            linear (ii) SEQUENCE DESCRIPTION: SEQ ID NO: 134:

GTCCACACCG TAAACGATCA TCATTAAATG TCGGC                              35

(2) INFORMATION FOR SEQ ID NO:    135:

(i) SEQUENCE CHARACTERISTICS:
            (A) LENGTH:              29
```

```
            (B) TYPE:              nucleic acid
            (C) STRANDEDNESS:      single
            (D) TOPOLOGY:          linear (ii) SEQUENCE DESCRIPTION: SEQ ID NO: 135:

TAGCTAACGC ATTAAATGAT GTGCCTGGG                                          29

(2) INFORMATION FOR SEQ ID NO:   136:

(i) SEQUENCE CHARACTERISTICS:
            (A) LENGTH:            20
            (B) TYPE:              nucleic acid
            (C) STRANDEDNESS:      single
            (D) TOPOLOGY:          linear (ii) SEQUENCE DESCRIPTION: SEQ ID NO: 136:

GCUCGAACGA GUCGGUGUUG                                                    20

(2) INFORMATION FOR SEQ ID NO:   137:

(i) SEQUENCE CHARACTERISTICS:
            (A) LENGTH:            18
            (B) TYPE:              nucleic acid
            (C) STRANDEDNESS:      single
            (D) TOPOLOGY:          linear (ii) SEQUENCE DESCRIPTION: SEQ ID NO: 137:

CCGAAUGGGU CGGUGUUG                                                      18

(2) INFORMATION FOR SEQ ID NO:   138:

(i) SEQUENCE CHARACTERISTICS:
            (A) LENGTH:            33
            (B) TYPE:              nucleic acid
            (C) STRANDEDNESS:      single
            (D) TOPOLOGY:          linear (ii) SEQUENCE DESCRIPTION: SEQ ID NO: 138:

GUCCACACCG UAAACGAUCA UCAUUAAAUG UCG                                     33

(2) INFORMATION FOR SEQ ID NO:   139:

(i) SEQUENCE CHARACTERISTICS:
            (A) LENGTH:            35
            (B) TYPE:              nucleic acid
            (C) STRANDEDNESS:      single
            (D) TOPOLOGY:          linear (ii) SEQUENCE DESCRIPTION: SEQ ID NO: 139:

GUCCACACCG UAAACGAUCA UCAUUAAAUG UCGGC                                   35

(2) INFORMATION FOR SEQ ID NO:   140:

(i) SEQUENCE CHARACTERISTICS:
            (A) LENGTH:            29
            (B) TYPE:              nucleic acid
            (C) STRANDEDNESS:      single
            (D) TOPOLOGY:          linear (ii) SEQUENCE DESCRIPTION: SEQ ID NO: 140:

UAGCUAACGC AUUAAAUGAU GUGCCUGGG                                          29

(2) INFORMATION FOR SEQ ID NO:   141:

(i) SEQUENCE CHARACTERISTICS:
            (A) LENGTH:            53
            (B) TYPE:              nucleic acid
```

(C) STRANDEDNESS:        single
        (D) TOPOLOGY:            linear (ii) SEQUENCE DESCRIPTION: SEQ ID NO: 141:

AATTTAATAC GACTCACTAT AGGGAGAGCG TAGCGATGAC CTATTTTACT TGC          53

1

NUCLEIC ACID PROBES TO UREAPLASMA

This application is a continuation-in-part of Kacian et al., entitled "Nucleic Acid Sequence Amplification Method, Composition and Kit," U.S. Ser. No. 07/879,686 filed May 6, 1992, now abandoned hereby incorporated by reference herein.

FIELD OF THE INVENTION

The invention described and claimed herein relates to the design and use of nucleic acid probes capable of detecting organisms of the genus Ureaplasma, and known strains or serotypes of the species Ureaplasma urealyticum, in test samples, e.g., from urogenital and endocervical specimens, tissue samples, amniotic and other body fluids, and from cultures.

BACKGROUND OF THE INVENTION

Two single strands of deoxyribo- ("DNA") or ribo- ("RNA") nucleic acid, formed from nucleotides, (including the bases adenine (A), cytosine (C), thymidine (T), guanine (G), uracil (U), or inosine (I)), may hybridize to form a double-stranded structure held together by hydrogen bonds between pairs of complementary bases. Generally, A is hydrogen bonded to T or U, while G or I are hydrogen bonded to C. Along the chain, classical base pairs AT or AU, TA or UA, GC, or CG are present. Additionally, some mismatched base pairs (e.g., AG, GU) may be present.

Bringing together two single strands of nucleic acid containing sufficient contiguous complementary bases, under conditions which will promote their hybridization, results in double-stranded nucleic acid. Under appropriate conditions, DNA/DNA, RNA/DNA, or RNA/RNA hybrids can form.

A probe is generally a single-stranded nucleic acid sequence complementary to some degree to a nucleic acid sequence sought to be detected ("target sequence"). A probe may be labeled with a reporter group moiety such as a radioisotope, a fluorescent or chemiluminescent moiety, or with an enzyme or other ligand which can be used for detection. Background descriptions of the use of nucleic acid hybridization to detect particular nucleic acid sequences are given in Kohne, U.S. Pat. No. 4,851,330 issued Jul. 25, 1989, and by Hogan et al., International Patent Application No. PCT/US87/03009, entitled "Nucleic Acid Probes for Detection and/or Quantitation of Non-Viral Organisms," both references hereby incorporated by reference herein. Hogan et al., supra, describe methods for determining the presence of a non-viral organism or a group of non-viral organisms in a sample (e.g., sputum, urine, blood and tissue sections, food, soil and water).

The genera Ureaplasma and Mycoplasma are prokaryotes and comprise the taxonomic Mollicutes class. Mollicutes lack a bacterial cell wall and have a small genome size. They are considered one of the smallest of the free-living microorganisms. Ureaplasma are unique among Mollicutes because of their characteristic ability to metabolize urea. There are fourteen known serotypes of *U. urealyticum* (Stemke and Robertson, *Diagn. Microbiol. Infect. Dis.* 31: 311 (1985)). The fourteen serotypes can be divided into at least two subspecies ("biotypes") based upon restriction fragment length polymorphism ("RFLP") of *U. urealyticum* genomic DNA (Harasawa et al., *Abstract S30-6 UIMS Meeting*, Osaka Japan (1990), and Robertson et al., *J. Clin. Microbiol.* 31: 824 (1993)), or based upon rRNA sequences (Hammond et al., *Abstract D17. Session* 60, *American Society for Microbiology General Meeting*, (1991)).

2

*U. urealyticum* is commonly found in the human urogenital tract but has been implicated in a wide spectrum of pathologies. Several studies have implicated *U. urealyticum* as a possible etiologic agent in diseases affecting adult males, fetuses and infants. Brunner et al., *Yale J. Biol. Med.* 56: 545 (1983), identified *U. urealyticum* as the etiologic agent responsible for nongonococcal urethritis (NGU) in approximately 30 percent of adult males tested who had NGU. Cassell et al., *Pediatr. Infect. Dis.* 5: S247 (1986), implicated *U. urealyticum* as a possible cause of chorioamnionitis, which could in turn adversely affect the outcome of pregnancy and the health of neonates. Stagno et al., *Pediatrics* 68: 322 (1981), found *U. urealyticum* in 21% of infants with pneumonia and found the association of *U. urealyticum* with pneumonia to be "statistically significant." Waites et al., *Lancet* 8575: 17 (1988), found *U. urealyticum* in 8 percent of the cerebrospinal fluid specimens taken from a high-risk population of newborn infants (100 predominantly pre-term infants). According to these investigators *U. urealyticum* was the most common organism isolated of those sought. *U. urealyticum* has also been implicated in a number of other pathogenic states including septic arthritis (Lee et al., *Arthritis and Rheumatism* 35: 43 (1992)).

Standard microbiological techniques generally identify *U. urealyticum* by observing the hydrolysis of urea. These techniques usually involve inoculating both a complex broth medium and an agar medium containing urea and other nutrients with a freshly obtained specimen (Brunner et al., supra).

References concerning detection of Ureaplasma include the following: Roberts et al., *Israel J. Med. Sci.,* 23: 618 (1987), describe the use of whole chromosomal DNA probes for detection of Ureaplasma in genital specimens; Ohse and Göbel, *Israel J. Med. Sci.* 23: 352 (1987) describe hybridization of *U. urealyticum* rRNA genes to cloned DNA of the *E. coli* rRNA operon; Gobel and Stanbridge ("Detection of Mycoplasma by DNA Hybridization", EPO application number 86304919.3, publication number 0 250 662) mention biological probes for detecting Mycoplasmas or prokaryotes in general, or specific Mycoplasma and eubacterial species; Gonzales et al. (*American Society for Microbiology Annual Meeting* 1991, *Abstract D*-16) mentions a method to detect Ureaplasma using a DNA probe directed to rRNA; Lee et al., supra, and Willoughby et al., *Infection and Immunity* 59: 2463 (1991), describe a procedure for detecting the *U. urealyticum* urease gene utilizing PCR; Deng et al., *PCR Methods and Applications* 1: 202 (1992), suggest that PCR-RFLP techniques should be capable of detecting Mollicutes; Brogan et al., *Molecular and Cellular Probes* 6: 411 (1992), describe the amplification of a 186 base pair genomic *U. urealyticum* DNA fragment; Robertson et al., supra, describe a technique involving the polymerase chain reaction using biotype specific primers to 16S rRNA gene sequences to distinguish the two *U. urealyticum* biotypes.

SUMMARY OF THE INVENTION

The featured invention discloses and claims novel oligonucleotide probes which are either targeted to a specific Ureaplasma nucleic acid target sequence or consist essentially of a specified nucleic acid sequence. The probes function by hybridizing to target *U. urealyticum* rRNA and/or rRNA gene sequences under stringent hybridization assay conditions. Thus, the probes can distinguish the genus Ureaplasma, including clinically significant *U. urealyticum* serotypes, from their known closest phylogenetic neighbors (Mycoplasma) and from other microorganism inhabitants of the human urogenital tract. Accordingly, the probes may be used in an assay to detect and/or quantitate Ureaplasma and U. urealyticum organisms.

Species of Mycoplasma found in humans include M. genitalium, M. pneumoniae and M. hominis. M. pneumoniae appears to be the most closely related Mycoplasma to U. urealyticum. M. genitalium is very similar in nucleic acid sequence to M. pneumoniae and has been isolated from the human genital tract. M. hominis is the most commonly isolated Mycoplasma from the genital tract.

Thus, in a first aspect, the invention described herein features hybridization assay probes able to selectively hybridize to a Ureaplasma target nucleic acid sequence. A Ureaplasma target nucleic acid sequence is a nucleic acid sequence present in Ureaplasma, preferably U. urealyticum nucleic acid, or a sequence complementary thereto. Preferably, the target nucleic acid sequence is not present in closely related Mycoplasma (e.g., M. pneumoniae). Sequences complementary to a target sequence may be generated by target amplification techniques such as polymerase chain reaction (PCR) or transcription mediated amplification (e.g., Kacian and Fultz, entitled "Nucleic Acid Amplification Methods", EPO application number 90307503.4; and Kacian et al., supra entitled "Nucleic Acid Sequence Amplification Method, Composition and Kit."

The featured probes can detect U. urealyticum and distinguish the genus Ureaplasma and known strains or serotypes of U. urealyticum found in humans from other bacteria including the phylogenetic closely related M. pneumoniae.

A hybridization assay probe is comprised of an oligonucleotide having a nucleic acid sequence sufficiently complementary to hybridize, under stringent hybridization assay conditions, to a 5S, 16S, or 23S rRNA, or to the corresponding ribosomal DNA ("rDNA") nucleic acid sequence, or to a nucleic acid sequence complementary thereto, of U. urealyticum. Stringent hybridization assay conditions, refer to conditions wherein a specific probe hybridizes with target nucleic acid (e.g., rRNA of Ureaplasma) and not another nucleic acid present in the test sample from either other microorganisms (e.g., Mycoplasma pneumonia) or humans. The probes are preferably 10 to 100 nucleotides in length.

By "probe" is meant to exclude naturally occurring nucleic acids. Purified oligonucleotide probes may be produced by techniques known in the art such as chemical synthesis and by in vitro or in vivo expression from recombinant nucleic acid molecules, e.g., retroviral vectors.

An oligonucleotide is made of nucleotide subunits covalently joined together. The sugar groups of the nucleotide subunits may be ribose, deoxyribose, or modified derivatives thereof such as O-methyl ribose. The nucleotide subunits may by joined by linkages such as phosphodiester linkages, modified linkages, or by non-nucleotide moieties that do not prevent hybridization of the oligonucleotide. Modified linkages include those linkages in which a standard phosphodiester linkage is replaced with a different linkage, such as a phosphorothioate linkage, or methylphosphonate linkage. When used as a hybridization assay probe, the oligonucleotide preferably contains a reporter group such as acridinium ester or a radioisotope to help identify hybridization of the probe to its target sequence.

In a related aspect, the invention described herein features hybridization assay probes able to selectively hybridize to a U. urealyticum nucleic acid target sequence present on either biotype 1 or biotype 2. The claimed target sequence is present in only one of the biotypes. Thus, an oligonucleotide probe directed to either biotype 1 or biotype 2 target site can distinguish between the biotypes.

In another related aspect, hybridization assay probes having a specific nucleic acid sequences complementary to rRNA or rDNA of Ureaplasma, are described. The probes are useful for detecting and/or quantitating Ureaplasma which may be present. These probes are complementary to a region of rRNA or rDNA which varies between Ureaplasma and Mycoplasma. Specific probes able to hybridize to Ureaplasma nucleic acid and distinguish Ureaplasma from Mycoplasma, comprise, consist essentially of, or consist of the sequences (written 5' to 3'):

(SEQ ID NO: 2) ACCTCTCAGT ACAGCTACGC G
(SEQ ID NO: 5) CATTTCCTAT CTTAGCGTTT CTTCCC
(SEQ ID NO: 8) CGTTAAGCAT CTAGATTTAA TACCAAACTT ACAAACCCG
(SEQ ID NO: 9) CCTACTACAC TCTAGGTTTA CAGTTTTTGA TACAGCTAGA
(SEQ ID NO: 11) GTCAGTGATA GTCCAAGTTG GC
(SEQ ID NO: 14) CGTTCGAGCC GACATTTAAT GATGATCG
(SEQ ID NO: 17) GCGTCGCAAT AGATGTCAAA CCTAG
(SEQ ID NO: 20) CGATTTTGCA GCAGTTTGTA TTAGCCATTG
(SEQ ID NO: 22) GCTATTTTCG GCTCTAGAGT GCTTGACTTC TGTGTTCGGG ATG
(SEQ ID NO: 23) CGGCTCTAGA GTGCTTGACT TCTGTGTTCG
(SEQ ID NO: 26) GGATGGGAAC AGGTATTTCC ACTCTGATAT GATCAC
(SEQ ID NO: 29) CAGTAATCTA ATTCTCATTA GACTGAGTTT CCTCATTCG and RNA equivalents thereto (SEQ ID NOs: 31, 34, 37, 40, 43, 46, 49, 52, 55, 58, 61, and 109), oligonucleotides complementary thereto (SEQ ID NOs: 32, 35, 38, 41, 44, 47, 50, 53, 56, 59, 62 and 110), and RNA equivalents to the oligonucleotides complementary thereto (SEQ ID NOs: 33, 36, 39, 42, 45, 48, 51, 54, 57, 60, 63, 111). Preferably, helper probe are used to facilitate the hybridization of the assay probe to its target nucleic acid sequence.

The phrases "consists essentially of" or "consisting essentially of" mean that the probe is provided as an oligonucleotide which hybridizes under stringent hybridization assay conditions to a target nucleic acid sequence of a particular organism and preferably does not hybridize with Mycoplasma described herein. A hybridization probe may be linked to other nucleic acids which do not affect hybridization. Generally, it is preferred that the probe be between 10 and 100 (most preferably between 15 and 50) nucleotides in length. Additionally, the probe may be provided in a vector.

For the listed probes, two sets of stringent hybridization assay conditions were used. One set comprised hybridization at 60° C. for one hour in a solution containing 0.095 M lithium succinate pH 5, 0.31 M lithium lauryl sulfate, 1.5 mM ethylenediaminetetraacetic acid (EDTA), 1.5 mM ethylene glycol bis (beta-amino ethyl ether) N, N, N', N' tetraacetic acid (EGTA). After the one hour, hybrids were separated from unhybridized probe by binding to magnetic amine microspheres in a solution containing 0.76 M sodium borate pH 7.5, 6% Triton at 60° C. for ten minutes and washed once in a solution containing 80 mM sodium borate pH 10.4 at room temperature.

Another set of stringent hybridization assay conditions was comprised of hybridization in 0.05 M lithium succinate pH 5, 0.6 M LiCl, 1% (w/v) lithium lauryl sulfate, 10 mM EDTA, 10 mM EGTA at 60° C. for 15 minutes, followed by the addition of 300 µl of 0.6 M sodium borate pH 8.5, 1% Triton X-100 at 60° C. for 5–7 minutes. Additional sets of stringent hybridization conditions can be determined based upon techniques known in the art and the present disclosure.

In another aspect, specific probes able to distinguish between different biotypes are described. Specific probes able to hybridize to a nucleic acid sequence present in only one Ureaplasma biotype comprise, consist essentially of, or consist of the sequences (written 5' to 3'):
SEQ ID NO. 121: CAACACCGAC TCGTTCGAGC
SEQ ID NO. 122: CAACACCGAC CCATTCGG and RNA equivalents thereto (SEQ ID NOs: 126 and 127), oligonucleotides complementary thereto (SEQ ID NOs: 131 and 132), and RNA equivalents to the oligonucleotides complementary thereto (SEQ ID NOs: 136 and 137). Preferably, a helper probe is used to facilitate the hybridization of the assay probe to its target nucleic acid sequence.

In another aspect, specific helper probe oligonucleotide sequences have been determined. Helper probes are used to facilitate the rate of hybridization of a hybridization assay probe to its target nucleic acid as described by Hogan and Milliman, U.S. Pat. No. 5,030,557 entitled "Means and Method for Enhancing Nucleic Acid Hybridization," issued Jul. 9, 1991 and hereby incorporated by reference herein. Helper probes featured herein include: SEQ ID NOs. 1, 3, 4, 6, 7, 8, 9, 10, 12, 13, 15, 16, 18, 19, 21, 24, 25, 26, 27, 28, 30, 123, 124, 125; RNA equivalents thereto, SEQ ID NOs. 37, 40, 64, 67, 70, 73, 76, 79, 82, 85, 88, 91, 94, 97, 100, 103, 106, 109, 112, 115, 118, 128, 129, 130; oligonucleotides complementary thereto, SEQ ID NOs. 38, 41, 65, 68, 71, 74, 77, 80, 83, 86, 89, 92, 95, 98, 101, 104, 107, 110, 113, 116, 119, 133, 134, 135; and RNA equivalents to the oligonucleotides complementary thereto, SEQ ID Nos. 39, 42, 66, 69, 72, 75, 78, 81, 84, 87, 90, 93, 96, 99, 102, 105, 108, 111, 114, 117, 120, 138, 139, 140.

Some oligonucleotide probes can be used as an assay probe or a helper probe (e.g., SEQ ID Nos. 8, 9, and 26, RNA equivalents thereto, SEQ ID Nos. 37, 40, and 109, oligonucleotides complementary thereto, 38, 41, and 110, and RNA equivalents to the oligonucleotides complementary thereto 39, 42, and 111.

In another related aspect, the invention features compositions comprising a nucleic acid hybrid between a hybridization assay probe and a nucleic acid sequence substantially complementary thereto (probe:target). "Substantially complementary" means there is sufficient complementarity between the nucleic acids such that the hybrid is stable under stringent hybridization conditions. One use of the formed hybrid is to detect the presence of a target sequence. For example, acridinium ester ("AE") present in hybrids is resistant to hydrolysis in alkali solution whereas acridinium ester present in single-stranded nucleic acid is hydrolyzed in alkali solution (Arnold et al., entitled "Homogeneous Protection Assay," EPO application number 88308767.8, publication number 309230, hereby incorporated by reference herein). Thus, binding of AE-labeled probe to target can be detected, after hydrolysis of the unbound AE-labeled probe, by measuring chemiluminescence of acridinium ester remaining in the nucleic acid hybrid.

In other related aspects, methods are described for detecting *Ureaplasma urealyticum* and distinguishing *Ureaplasma urealyticum* from Mycoplasma such as *Mycoplasma orale*, *Mycoplasma fermentans*, *Mycoplasma capricolum*, *Mycoplasma lipophilum*, and *Mycoplasma salivarium;* distinguishing between *Ureaplasma urealyticum* biotype 1 and *Ureaplasma urealyticum* biotype 2; and detecting the presence of a *Ureaplasma urealyticum* nucleic acid sequence. These methods can be used on test samples obtained from human specimens.

The probes of this invention offer a rapid, non-subjective method of identifying and quantitating the presence of specific rRNA sequences unique to the genus Ureaplasma and all strains of *U. urealyticum* in a test sample.

Other features and advantages of the invention will be apparent from the following description of the preferred embodiments thereof and from the claims.

DESCRIPTION OF THE PREFERRED EMBODIMENTS

We have identified preferred target sequences present in the rRNA or rDNA of *U. urealyticum* and designed specific oligonucleotide probes to these sequences and their complements which can be used to identify Ureaplasma. The probes can detect the genus Ureaplasma including *U. urealyticum* serotypes and distinguish them from their known and presumably most closely related taxonomic or phylogenetic neighbors. Probes are also described which distinguish *U. urealyticum* biotype 1 and biotype 2. Also described are methods using the featured probes or target sites.

In a preferred embodiment, the nucleic acid hybridization assay probes can distinguish *U. urealyticum* from *M. genitalium, M. pneumoniae,* or *M. hominis.* In another preferred embodiment, the nucleic acid hybridization probes can distinguish *U. urealyticum* from *M. orale, M. fermentans, M. capricolum, M. lipophilum,* and *M. salivarium.* These Mycoplasma have been isolated from humans.

Prokaryotic organisms (excluding viruses) contain rRNA genes encoding 5S rRNA, 16S rRNA and 23S rRNA. Using methods known to those skilled in the art, partial or full rRNA sequences of *U. urealyticum* and Mycoplasma were obtained. These sequences were aligned based on regions of sequence homology. Sequence variations were then identified from the aligned sequences and used as target sequences for hybridization assay probes.

Obtaining rRNA Sequences

Sequence information was obtained experimentally and from published information (see, Weisburg et al., *J. Bacteriol* 171: 6455 (1989); and Rogers et al., Proc. Natl. Acad. Sci., U.S.A., 82: 1160 (1985)). Experimental information was obtained by isolating and sequencing the ribonucleic acid from various organisms using sequence standard techniques known in the art. Nucleic acids were obtained using an oligonucleotide primer complementary to a conserved region of rRNA and extending the primer using reverse transcriptase. Nucleic acid sequences were then derived using the method of dideoxynucleotide chain termination. (e.g., Lane et al., *Proc. Natl. Acad. Sci. U.S.A.,* 82: 6955 (1985)).

Probe Design And Hybridization Conditions

To facilitate the identification of nucleic acid sequences to be used as probes, the nucleotide sequences from different organisms were first aligned to maximize homology. Within the rRNA molecule there is a close relationship between secondary structure and function. This imposes restrictions on evolutionary changes in the primary sequence so that the secondary structure is maintained. For example, if a base is changed on one side of a helix, a compensating change is made on the other side to preserve the complementarity (this is referred to as co-variance). This allows two very different sequences to be aligned based on the conserved primary sequence and also on the conserved secondary structure elements. Potential target sequences for the hybridization probes were identified by noting variations in the homology of the aligned sequences.

The sequence evolution at each of the variable regions is mostly divergent. Because of the divergence, more distant phylogenetic relatives of U. urealyticum show greater variability to U. urealyticum at the variable region than phylogenetically closer relatives. We observed sufficient variation between *U. urealyticum* and strains of Mycoplasma found in the same sample to design several useful probes and identify preferred target sites.

Selective hybridization of probe to target can be accomplished by choosing the appropriate hybridization assay conditions and proper probe design. The stability of the probe:target nucleic acid hybrid should be chosen to be compatible with the assay and washing conditions so that hybrids will only form between highly complementary sequences. Manipulation of one or more of the different assay conditions determines the exact sensitivity and specificity of a particular probe. The following guidelines are useful for designing probes and determining stringent hybridization assay conditions.

Probes should be designed to have an appropriate melting temperature ($T_m$). The appropriate $T_m$ can be obtained by varying the probe length and nucleotide composition (percentage of G+C versus A+T). The probe length and nucleotide composition should preferably be chosen to correspond to a $T_m$ about 2–10° C. higher than the temperature at which the final assay will be performed.

In general, the optimal hybridization temperature for oligonucleotide probes of about 10–50 bases in length is approximately 5° C. below the melting temperature for a given duplex. Incubation at temperatures below the optimum temperature may allow mismatched base sequences to hybridize and can therefore decrease specificity. The longer the probe, the more hydrogen bonding between base pairs and, in general, the higher the $T_m$. Increasing the percentage of G and C also increases the $T_m$ because G-C base pairs exhibit additional hydrogen bonding and therefore greater thermal stability than A-T base pairs.

The preferred method to determine $T_m$ measures hybridization using a Hybridization Protection Assay (HPA) according to Arnold et al., supra entitled "Homogeneous Protection Assay." $T_m$ can be measured using HPA in the following manner. A probe:target hybrid is formed in a lithium succinate buffered solution (0.1 M lithium succinate buffer, pH 5.0, 2 mM EDTA, 2 mM EGTA, 10% (w/v) lithium lauryl sulfate) using an excess amount of target. Aliquots of the hybrid are then diluted in the lithium succinate buffered solution and incubated for five minutes at various temperatures starting below that of the anticipated $T_m$ (typically 55° C.) and increasing in 2–5° C. increments. This solution is then diluted with a mild alkaline borate buffer (0.15 M sodium tetraborate, pH 7.6, 5% (v/v) Triton X-100)) and incubated at a lower temperature (for example 50° C.) for ten minutes. Under these conditions the acridinium ester attached to a single-stranded probe is hydrolyzed while the acridinium ester attached to hybridized probe is relatively protected from hydrolysis. Thus, the amount of acridinium ester remaining is proportional to the amount of hybrid and can be measured by the chemiluminescence produced from the acridinium ester upon the addition of hydrogen peroxide followed by alkali. Chemiluminescence can be measured in a luminometer (e.g., the Gen-Probe LEADER I or LEADER 50). The resulting data is plotted as percent of maximum signal (usually from the lowest temperature) versus temperature. The $T_m$ is defined as the temperature at which 50% of the maximum signal remains. In addition to the method above, $T_m$ may be determined by isotopic methods well known to those skilled in the art (e.g., Hogan et al., supra).

It should be noted that the $T_m$ for a given hybrid varies depending on the hybridization solution used. Factors such as the salt concentration, detergents, and other solutes can affect hybrid stability during thermal denaturation (J. Sambrook, E. F. Fritsch and T. Maniatis, *Molecular Cloning,* ch. 11 (2d ed. 1989)). Conditions such as ionic strength and incubation temperature under which a probe will be used to hybridize to target should be taken into account in constructing a probe. Thermal stability of hybrids increases as the ionic strength of the reaction mixture increases. On the other hand, chemical reagents which disrupt hydrogen bonds, such as formamide, urea, dimethyl sulfoxide and alcohols, can greatly reduce the thermal stability of the hybrids.

To ensure specificity of probe for target, it is desirable to have probes which hybridize only under conditions of high stringency. Under conditions of high stringency only highly complementary nucleic acid hybrids will form; hybrids without a sufficient degree of complementarity will not form. Accordingly, the stringency of the assay conditions determines the amount of complementarity needed between two nucleic acid strands to form a hybrid. Stringency is chosen to maximize the difference in stability between the hybrid formed with the target and other nucleic acid sequences.

Proper specificity may be achieved by minimizing the length of perfect complementarity to non-target organisms, avoiding G and C rich regions of homology to non-target sequences, and by constructing the probe to contain as many destabilizing mismatches to nontarget sequences as possible. Whether a probe sequence is useful to detect only a specific type of organism depends largely on the thermal stability difference between probe:target hybrids versus probe:non-target hybrids. In designing probes, the differences in these $T_m$ values should be as large as possible (preferably 2° C.–5° C. or more).

The length of the target nucleic acid sequence, and accordingly the length of the probe sequence, can also be important. In some cases, there may be several sequences from a particular region, varying in location and length, which yield probes with the desired hybridization characteristics. In other cases, one sequence may be significantly better than another which differs merely by a single base. While it is possible for nucleic acids that are not perfectly complementary to hybridize, the longest stretch of perfectly homologous base sequence will generally determine hybrid stability. Oligonucleotide probes of different lengths and base composition may be used. Preferably, oligonucleotide probes are between 10 to 100 and, more preferably, between 15 to 50 bases in length.

Regions of rRNA known to form strong internal structures inhibitory to hybridization are less preferred target regions. Likewise, probes with extensive self-complementarity should be avoided. As explained above, hybridization is the association of two single strands of complementary nucleic acid to form a hydrogen-bonded double strand. It is implicit that if one of the two strands is wholly or partially involved in an intramolecular or intermolecular hybrid it will be less able to participate in the formation of a new intermolecular probe:target hybrid. In the case of rRNA, the molecule is known to form very stable intramolecular hybrids. By designing a probe so that a substantial portion of the targeted sequence is single-stranded, the rate and extent of hybridization between probe and target may be greatly increased.

An rDNA target occurs naturally in a double-stranded form as does the product of the polymerase chain reaction (PCR). These double-stranded targets are naturally inhibitory to hybridization with a probe and require denaturation prior to hybridization. Appropriate denaturation and hybridization conditions are known in the art (e.g., E. M. Southern, *J. Mol. Biol.* 98: 503 (1975)).

Probe Synthesis

Once a presumptive unique target sequence has been identified, a complementary oligonucleotide probe is selected and synthesized. Defined oligonucleotide probes may be produced by any of several well-known methods, including automated solid-phase chemical synthesis using cyanoethylphosphoramidite precursors (Barone et al., *Nucleic Acids Research* 12: 4051 (1984)), and as described in J. Sambrook, E. F. Fritsch and T. Maniatis, *Molecular Cloning*, ch. 11 (2d ed. 1989). Following synthesis and purification of a particular oligonucleotide probe, several different procedures may be utilized to determine the acceptability of the probe in terms of size and purity. One such procedure is polyacrylamide gel electrophoresis. Another such procedure is High Pressure Liquid Chromatography ("HPLC"). These procedures are well known to those skilled in the art.

Once synthesized, selected oligonucleotide probes may be labeled with a reporter group by any of several well-known methods (e.g., supra, J. Sambrook et al.). Useful labels include radioisotopes and non-radioactive reporting groups. Isotopic labels include $^3$H, $^{35}$S, $^{32}$P, $^{125}$I, $^{57}$Co and $^{14}$C. Isotopic labels can be introduced into the oligonucleotide by techniques known in the art such as nick translation, end labeling, second strand synthesis, the use of reverse transcription, and by chemical methods. When using radio-labeled probes, hybridization can be detected by autoradiography, scintillation counting, or gamma counting. The detection method selected will depend upon the particular radioisotope used for labeling.

Non-isotopic materials can also be used for labeling and may be introduced internally into the nucleic acid sequence or at the end of the nucleic acid sequence. Modified nucleotides may be incorporated enzymatically or chemically. Chemical modifications of the probe may be performed during or after synthesis of the probe, for example, through the use of non-nucleotide linker groups as described by Arnold et al., entitled "Non-Nucleotide Linking Reagents for Nucleotide Probes," EPO application number 88308766.0, publication number 313219, hereby incorporated by reference herein. Non-isotopic labels include fluorescent molecules, chemiluminescent molecules, enzymes, cofactors, enzyme substrates, haptens or other ligands.

Preferably, the probes are labeled with an acridinium ester. Acridinium ester labeling may be performed as described by Arnold et al., U.S. Pat. No. 5,185,439 entitled "Acridinium Ester Labeling and Purification of Nucleotide Probes" issued Feb. 9, 1993 and hereby incorporated by reference herein.

Helper Probes

The rate of nucleic acid hybridization of an assay probe with its target nucleic acid is enhanced by the use of "Helper Probes" as disclosed in Hogan and Milliman, U.S. Pat. No. 5,030,557 and hereby incorporated by reference herein. Helper probes are selected to hybridize to nucleic acid sequences located near the region targeted by the assay probe. Hybridization of the helper probe alters the secondary and tertiary structure and thereby renders the targeted area of the nucleic acid more accessible for the detection probe. Helper probes to be used with the assay probes described herein include oligonucleotides having the following nucleotide sequences (written 5' to 3'):

(SEQ ID NO: 1) TCATTGACTT GGTGAGCCAT TACCTCAC (SEQ ID NO: 3) GCCGTGTCTC AGTCCCATTG TGGCTGTTCT (SEQ ID NO: 4) ATATAAAAGA ACTTTACAAT CTATAAGACC TTCATCGTTC ACGCGGC (SEQ ID NO: 6) GGCACATAGT TAGCCGATAC TTATTCAAAT GGTACAGTCA AA (SEQ ID NO: 7) CCTGCGCTCG TTTTACGCCC AGTAAATCCG GATAACGC (SEQ ID NO: 8) CGTTAAGCAT CTAGATTTAA TACCAAACTT ACAAACCCG (SEQ ID NO: 9) CCTACTACAC TCTAGGTTTA CAGTTTTTGA TACAGCTAGA (SEQ ID NO: 10) GCCTTCGCCA CCGGTGTTCT TCCATATATC TA (SEQ ID NO: 12) CTAATCCTAT TTGCTCCCCA CACTTTCGAG CCTAAGC (SEQ ID NO: 13) TTTACGGTGT GGACTACTAG GGTAT (SEQ ID NO: 15) GCGTTAGCTA CAACACCGAC T (SEQ ID NO: 16) GTAAGGTTCT ACGTGTATTG TCAAATTAAG CAACATGCTC CACCAC (SEQ ID NO: 18) CGACAACCAT GCACCACCTG TCATATTGTT AACCTCAAC (SEQ ID NO: 19) TAGCACGTTT GCAGCCCTAG ATATAAGGGG CATGATG (SEQ ID NO: 21) CGAATTGCAG CCCTCTATCC GAACTGAGAC TAACTTTTTC TG (SEQ ID NO: 24) GGAACAGGTA TTTCCACTCT GATATGATCA CTAC, (SEQ ID NO: 25) GCGTAGCGAT GACCTATTTT ACTTGC (SEQ ID NO: 26) GGATGGGAAC AGGTATTTCC ACTCTGATAT GATCAC, (SEQ ID NO: 27) GCGTAGCGAT GACCTATTTT ACTGCGCTA TTTT (SEQ ID NO: 28) GAGATCAACG GATTAAAGCC TCTTATCAGC TACCCGTTGC TTATCGCAGA TTAGCACG (SEQ ID NO: 30) CACTTCACCA GGTATCGCTC TGTTAAACTA TGAATTCATT TATA (SEQ ID NO: 123) CGACATTTAA TGATGATCGT TTACGGTGTG GAC, (SEQ ID NO: 124) GCCGACATTT AATGATGATC GTTTACGGTG TGGAC, (SEQ ID NO: 125) CCCAGGCACA TCATTTAATG CGTTAGCTA, RNA equivalents thereto, SEQ ID NOs. 37, 40, 64, 67, 70, 73, 76, 79, 82, 85, 88, 91, 94, 97, 100, 103, 106, 109, 112, 115, 118, 128, 129, 130; oligonucleotides complementary thereto, SEQ ID NOs. 38, 41, 65, 68, 71, 74, 77, 80, 83, 86, 89, 92, 95, 98, 101, 104, 107, 110, 113, 116, 119, 133, 134, 135; and RNA equivalents to the oligonucleotides complementary thereto, SEQ ID Nos. 39, 42, 66, 69, 72, 75, 78, 81, 84, 87, 90, 93, 96, 98, 102, 105, 108, 111, 114, 117, 120, 138, 139, 140.

Preferably, the following hybridization assay probe and helper probe combinations are used:

| | Hybridization probe | Helper probes |
|---|---|---|
| SEQ ID NOs: | 2 | 1 and 3 |
| SEQ ID NOs: | 5 | 4 and 6 |
| SEQ ID NOs: | 8 | 7 and 9 |
| SEQ ID NOs: | 9 | 8 and 10 |
| SEQ ID NOs: | 11 | 10 and 12 |
| SEQ ID NOs: | 14 | 13 and 15 |
| SEQ ID NOs: | 17 | 16 and 18 |
| SEQ ID NOs: | 20 | 19 and 21 |
| SEQ ID NOs: | 22 | 24 and 25 |
| SEQ ID NOs: | 23 | 26 and 27 |

-continued

| | Hybridization probe | Helper probes |
|---|---|---|
| SEQ ID NOs: | 29 | 28 and 30 |
| SEQ ID NOs: | 121 | 123 and 125 |
| SEQ ID NOs: | 122 | 124 and 125 |

EXAMPLES

Examples are provided below to illustrate different aspects and embodiments of the present invention. These examples are not intended in any way to limit the disclosed invention.

Probes specific for Ureaplasma were identified by sequencing with primers complementary to the 16S and 23S rRNAs of *U. urealyticum* T-960 (CX-8), or from published 5S sequences. The nucleic acid sequence from phylogenetically near neighbors, including *M. genitalium, M. pneumoniae, M. iowae, M. muris, M. pirum* and *M. gallisepticum*, were used as comparisons with the nucleic sequence from *U. urealyticum* to determine variable regions.

The following hybridization assay probe sequences are featured in the examples described below::
(SEQ ID NO: 2) ACCTCTCAGT ACAGCTACGC G
(SEQ ID NO: 5) CATTTCCTAT CTTAGCGTTT CTTCCC
(SEQ ID NO: 8) CGTTAAGCAT CTAGATTTAA TAC-CAAACTT ACAAACCCG
(SEQ ID NO: 9) CCTACTACAC TCTAGGTTTA CAGTTTTTGA TACAGCTAGA
(SEQ ID NO: 11) GTCAGTGATA GTCCAAGTTG GC
(SEQ ID NO: 14) CGTTCGAGCC GACATTTAAT GAT-GATCG
(SEQ ID NO: 17) GCGTCGCAAT AGATGTCAAA CCTAG
(SEQ ID NO: 20) CGATTTTGCA GCAGTTTGTA TTAGCCATTG
(SEQ ID NO: 22) GCTATTTTCG GCTCTAGAGT GCT-TGACTTC TGTGTTCGGG ATG
(SEQ ID NO: 23) CGGCTCTAGA GTGCTTGACT TCT-GTGTTCG
(SEQ ID NO: 29) CAGTAATCTA ATTCTCATTA GACT-GAGTTT CCTCATTCG
(SEQ ID NO: 59) CGAACACAGA AGTCAAGCAC TCTAGAGCCG,
(SEQ ID NO: 110) GTGATCATAT CAGAGTGGAA ATACCTGTTC CCATCC,
(SEQ ID NO: 121) CAACACCGAC TCGTTCGAGC, and
(SEQ ID NO: 122) CAACACCGAC CCATTCGG.

The probes were synthesized with a non-nucleotide linker as described by Arnold et al. supra, "Non-Nucleotide Linking Reagents For Nucleotide Probes," then labeled with a chemiluminescent acridinium ester as described by Arnold et al., supra, U.S. Pat. No. 5,185,439. The reactivity and specificity of the probes for *U. urealyticum* were demonstrated using a hybridization and separation format (Example 1, Tables 1–4) or a homogeneous assay format (Examples 2 and 3, Tables 5 and 6; Example 4, Tables 7 and 8). These procedures are described by Arnold et al., supra, "Homogeneous Protection Assay"; Arnold et al., "Polycationic Supports and Nucleic Acid Purification, Separation and Hybridization" EPO application number 88301839.2, publication number 0 281 390 (hereby incorporated by reference herein); and Arnold et al., *Clin. Chem.*, 35:1588 (1989) (hereby incorporated by reference herein).

Results are given in relative light units (RLU). Probes were hybridized to a cell lysate or RNA purified according to J. Sambrook, E. F. Fritsch and T. Maniatis, *Molecular Cloning* (2d ed. 1989). Alternatively, lysates, especially of Mycobacteria, Gram positive organisms, or yeasts, could be obtained utilizing a method described by Murphy et al., "Method for Releasing RNA and DNA from Cells," EPO application number 87303641.2, publication number 288618, hereby incorporated by reference herein. The following examples describe hybridization assay probes targeted to *U. urealyticum* rRNA sequences, or the corresponding gene, and their use in a hybridization assay.

Example 1

This example illustrates the ability of a mixture containing acridinium ester-labeled probes targeted to Ureaplasma 16S rRNA to detect various Ureaplasma strains but not other microorganisms. The mixture contained assay probes having SEQ ID NOs. 2, 5, 8, 9, 11, 14, 17 and 20, and the corresponding unlabeled "Helper Probes" (as described above).

Table 1 presents data using these probes with an excess of RNA released from liquid broth cultures containing $10^6$–$10^8$ organisms. An equal volume of cell lysate and hybridization solution containing 0.19 M lithium succinate pH 5, 0.62 M lithium lauryl sulfate, 3 mM ethylenediaminetetraacetic acid (EDTA), 3 mM ethylene glycol bis (beta-amino ethyl ether) N, N, N', N' tetraacetic acid (EGTA) were mixed and incubated at 60° C. for one hour. Hybrids were then bound to magnetic amine microspheres (Advanced Magnetics, Inc., Cambridge, Mass.) in a solution containing 0.76 M sodium borate pH 7.5, 6% Triton and washed once in a solution containing 80 mM sodium borate pH 10.4. The chemiluminescence associated with the particles, from the hybridized acridinium ester-labeled probes, was measured in a luminometer equipped with automatic injection of 0.1% hydrogen peroxide in 1 mM nitric acid, followed by injection of a 1N sodium hydroxide solution. RLU from a hybridization reaction containing 1 ng of non-target RNA was subtracted from the values shown. The data in Table 1 show that the probes hybridize to known strains or serotypes of *U. urealyticum* found in humans as well as to *U. cati, U. diversum* and *U. gallorale* of animal origin.

Table 2 shows that the probes distinguish Ureaplasma from several closely related Mycoplasma, Acholeplasma, or Spiroplasma species. A net RLU value greater than 300 RLU was considered a positive reaction. An all-bacteria/yeast probe mixture was used as a control to demonstrate the presence of bacterial nucleic acid (data not shown). Hogan et al., supra, entitled "Nucleic Acid Probes for Detection and/or Quantitation of Non-Viral Organisms," gives examples of suitable all-bacteria/yeast probe mixtures. The all-bacteria probe used in the examples described herein is a derivative of all-bacteria probe No. 7 described by Hogan et al., (the all-bacteria probe used in the examples described herein is shifted so that it is four nucleotides shorter on the 5' end but 5 bases longer on the 3' end probe than the Hogan probe No. 7). The yeast probe is a derivative of fungal probe No. 1 described in Hogan et al.

Table 3 shows that the assay probe mixture distinguishes Ureaplasma from members of a panel of urogenital microbes. The all-bacteria/yeast probe mixture was also used as a control in this experiment.

Table 4 shows that the assay probes distinguish Ureaplasma from twenty-seven bacterial genera representing a phylogenetic cross section of microorganisms. Again, the all-bacteria/yeast probe mixture was used as a control in this experiment.

TABLE 1

HYBRIDIZATION OF UREAPLASMA 16S rRNA PROBES WITH UREAPLASMA STRAINS AND SEROTYPES

| ATCC NO. | ORGANISM/ STRAIN | SEROTYPE | NET RLU[a] |
|---|---|---|---|
| | *U. urealyticum* strain | | |
| 27813 | 7 | 1 | 634,146 |
| 27618 | T-960(CX8) | 8 | 592,533 |
| 27814 | 23 | 2 | 775,013 |
| 27816 | 58 | 4 | 758,427 |
| 27619 | K510(CX4) | — | 906,488 |
| 27815 | 27 | 3 | 703,288 |
| 27817 | 354 | 5 | 474,113 |
| 27818 | Pi | 6 | 769,951 |
| 27819 | Co | 7 | 780,741 |
| 29557 | K71-21 | 4 | 876,253 |
| 29558 | K42-35 | 4 | 933,227 |
| 29559 | K12-19 | 4/8 | 892,978 |
| 33175 | Vancouver | 9 | 576,453 |
| 33695 | K2 | 11 | 875,684 |
| 33696 | U24 | 12 | 863,070 |
| 33697 | U26 | 14 | 677,350 |
| 33698 | U38 | 13 | 749,523 |
| 33699 | Western | 10 | 862,237 |
| 49228 | *U. cati* | — | 467,562 |
| 43321 | *U. diversum* | — | 772,938 |
| 43346 | *U. gallorale* | — | 1,161,922 |

[a]Chemiluminescence was measured in a Gen-Probe LEADER I luminometer and data are expressed in net Relative Light Units (signal minus the negative control containing 1 ng non-Ureaplasma rRNA).

TABLE 2

HYBRIDIZATION OF UREAPLASMA 16S rRNA PROBES WITH OTHER MOLLICUTES

| ORGANISM | ATCC NO. | EXPERIMENT NO. | PROBE MIX NET RLU |
|---|---|---|---|
| *Mycoplasma fermentans*[a] | 15474 | 1 | 15 |
| *Mycoplasma gallisepticum*[a] | 19610 | 1 | 30 |
| *Mycoplasma genitalium*[a] | 33530 | 1 | 31 |
| *Mycoplasma hominis*[a] | 23114 | 1 | 38 |
| *Mycoplasma iowae*[a] | 33552 | 1 | 81 |
| *Mycoplasma muris*[a] | 33757 | 1 | 17 |
| *Mycoplasma pirum*[a] | 25960 | 1 | 26 |
| *Mycoplasma pneumoniae*[a] | 15531 | 1 | 62 |
| *Spiroplasma mirum*[a] | 29335 | 1 | 105 |
| Spiroplasma sp. MQ-1[a] | 33825 | 1 | 66 |
| *Acholeplasma laidlawii*[c] | 29804 | 2 | 180 |
| *Mycoplasma arthritidis*[c] | 35943 | 2 | 14 |
| *Mycoplasma buccale*[c] | 23636 | 2 | 58 |
| *Mycoplasma orale*[c] | 23714 | 2 | −18 |
| *Mycoplasma primatum*[c] | 15497 | 2 | −29 |
| *Mycoplasma salivarium*[c] | 14277 | 2 | 11 |
| *Ureaplasma urealyticum*[b] | 27618 | 2 | 938 |

[a]0.10 ng purified RNA.
[b]0.01 ng purified RNA.
[c]Whole cell lysates from $10^7$–$10^8$ organisms.

TABLE 3

HYBRIDIZATION OF UREAPLASMA 16S rRNA PROBES WITH UROGENITAL MICROBES

| ORGANISM[a] | ATCC NO. | UREAPLASMA 16S PROBES NET RLU | ALL-BACTERIA/ YEAST PROBES NET RLU |
|---|---|---|---|
| *Bacteroides fragilis* | 23745 | 43 | 605,178 |
| *Bacteroides ureolyticus* | 43605 | 37 | 112,716 |
| *Candida albicans* | 18804 | 26 | 13,380 |
| *Chlamydia trachomatis* | VR-878 | −1 | 76,109 |
| *Clostridium perfringens* | 13124 | −8 | 419,044 |
| *Eikenella corrodens* | 23834 | −13 | 812,060 |
| *Gardnerella vaginalis* | 14018 | 11 | 55,694 |
| *Haemophilus influenzae* | 9795 | 6 | 1,203,162 |
| *Lactobacillus acidophilus* | 4356 | −10 | 424,616 |
| *Listeria monocytogenes* | 35152 | −8 | 33,993 |
| *Mycobacterium smegmatis* | 14468 | 1 | 14,392 |
| *Neisseria gonorrhoeae* | 19424 | 122 | 147,963 |
| *Peptostreptococcus anaerobius* | 27337 | −8 | 290,081 |
| *Staphylococcus aureus* | 12598 | 29 | 16,256 |
| *Staphylococcus epidermidis* | 12228 | 66 | 4,519 |
| *Torulopsis glabrata* | 2001 | 0 | 646,442 |

[a]Whole cell lysates were tested at a concentration of $10^7$ cells per reaction.

TABLE 4

HYBRIDIZATION OF UREAPLASMA 16S rRNA PROBES WITH A PHYLOGENETIC PANEL

| ORGANISM[a] | ATCC NO. | UREAPLASMA 16S PROBES NET RLU | ALL-BACTERIA/ YEAST PROBES NET RLU |
|---|---|---|---|
| *Ureaplasma urealyticum* | 27618 | 1,170 | ND |
| *Alcaligenes faecalis* | 8750 | −6 | 751,053 |
| *Bacillus subtilis* | 6051 | 14 | 19,523 |
| *Campylobacter jejuni* | 33560 | 2 | 1,079,901 |
| *Chromobacterium violaceum* | 29094 | 10 | 1,026,462 |
| *Citrobacter freundii* | 6750 | 2 | 758,996 |
| *Actinomyces pyogenes* | 19411 | 12 | 148,548 |
| *Corynebacterium xerosis* | 373 | 38 | 2,091 |
| *Deinococcus radiodurans* | 35073 | −4 | 78,908 |
| *Derxia gummosa* | 15994 | 20 | 753,002 |
| *Enterobacter aerogenes* | 13048 | 8 | 967,109 |
| *Enterobacter cloacae* | 10699 | 5 | 1,078,720 |
| *Enterococcus avium* | 14025 | 32 | 10,594 |
| *Enterococcus faecalis* | 19433 | 42 | 32,000 |
| *Erwinia herbicola* | 33243 | 9 | 821,862 |
| *Escherichia coli* | 10798 | 66 | 959,572 |
| *Klebsiella pneumoniae* | 23357 | 12 | 1,326,216 |
| *Legionella pneumophila* | 33152 | 34 | 869,560 |
| *Micrococcus luteus* | 9341 | 50 | 6,256 |
| *Plesiomonas shigelloides* | 14029 | 17 | 837,909 |
| *Proteus mirabilis* | 25933 | 17 | 927,223 |
| *Pseudomonas aeruginosa* | 10145 | 5 | 1,285,353 |
| *Pseudomonas fluorescens* | 13525 | 10 | 1,318,299 |
| *Rhodospirillum rubrum* | 11170 | 25 | 563,898 |
| *Streptococcus agalactiae* | 13813 | 21 | 204,717 |
| *Streptococcus bovis* | 33317 | 7 | 402,823 |
| *Vibrio parahaemolyticus* | 17802 | 7 | 1,138,932 |
| *Yersinia enterocolitica* | 9610 | 7 | 1,136,326 |

[a]Whole cell lysates were tested at a concentration of $10^7$ cells per reaction. The Ureaplasma sample contained 0.01 ng of *Ureaplasma urealyticum* rRNA.
ND = not done.

Example 2

Hybridization of an acridinium ester-labeled probe, targeted to a 23S rRNA *U. urealyticum* region, to *U. urealyti*- cum and other bacteria was evaluated. Lysate (L) or purified RNA was hybridized to probe SEQ ID NO. 29 and helper probes SEQ ID NOs. 28 and 30 in 0.05 M lithium succinate pH 5, 0.6 M LiCl, 1% (w/v) lithium lauryl sulfate, 10 mM EDTA, 10 mM EGTA at 60° C. for 15 minutes, followed by addition of 300 μl of 0.6 M sodium borate pH 8.5, 1% Triton X-100 at 60° C. for 5–7 minutes. Samples were read in a luminometer as described in Example 1. The Ureaplasma sample contained 1 μg of *U. urealyticum* rRNA.

As shown in Table 5, probes targeted to 23S rRNA *U. urealyticum* readily distinguish *U. urealyticum* from other organisms including Mycoplasma. The data in this table is reported in RLU without subtracting background and Negative control values. Values greater than about 20,000 to 30,000 RLU were considered positive results in this assay.

TABLE 5

HYBRIDIZATION OF UREAPLASMA-SPECIFIC 23S rRNA PROBES TO OTHER MOLLICUTES AND *E. COLI*

| ORGANISM | ATCC NO. | 23S PROBE RLU |
|---|---|---|
| Mycoplasma arthritidis (L) | 35943 | 746 |
| Mycoplasma buccale (L) | 23636 | 565 |
| Mycoplasma fermentans (L) | 15474 | 948 |
| Mycoplasma iowae (L) | 33552 | 4,241 |
| Mycoplasma muris (L) | 33757 | 4,346 |
| Mycoplasma pirum (L) | 25960 | 596 |
| Mycoplasma primatum (L) | 15497 | 709 |
| Mycoplasma salivarium (L) | 14277 | 629 |
| Spiroplasma sp. MQ-1 (L) | 33825 | 737 |
| Acholeplasma laidlawii | 29804 | 1,052 |
| Mycoplasma gallisepticum | 19610 | 432 |
| Mycoplasma genitalium | 33530 | 4,503 |
| Mycoplasma hominis | 23114 | 450 |
| Mycoplasma orale | 23714 | 945 |
| Mycoplasma pneumoniae | 15531 | 4,073 |
| Spiroplasma mirum | 29335 | 431 |
| Escherichia coli | 10798 | 772 |
| Ureaplasma urealyticum | 27618 | 1,307,260 |

Example 3

Acridinium ester-labeled probe SEQ ID NOs. 22 or 23 targeted to 5S rRNA was hybridized to an excess of RNA released from cells in the form of cell lysate or purified as described above and assayed as described in Example 2. Probe SEQ ID NO. 22 was hybridized in the presence of helper probes SEQ ID NOs. 24 and 25; probe SEQ ID NO. 23 was hybridized in the presence of helper probes SEQ ID NOs. 26 and 27.

As shown in Table 6, the probes targeted to *Ureaplasma urealyticum* 5S rRNA were able to distinguish this organism from other Mollicutes.

TABLE 6

HYBRIDIZATION OF UREAPLASMA 5S rRNA PROBES TO MOLLICUTES

| ORGANISM | ATCC NO. | PROBE SEQ ID NO. 22 RLU | PROBE SEQ ID NO. 23 RLU |
|---|---|---|---|
| Mycoplasma arginini | 23838 | 1,332 | 3,655 |
| Mycoplasma arthritidis[a] | 35943 | 1,382 | 3,957 |
| Mycoplasma bovigenitalium[a] | 19852 | 1,395 | 4,864 |
| Mycoplasma bovis[a] | 25523 | 1,280 | 4,885 |
| Mycoplasma buccale[a] | 23636 | 1,332 | 5,762 |
| Mycoplasma californicum[a] | 33461 | 1,466 | 6,218 |

TABLE 6-continued

HYBRIDIZATION OF UREAPLASMA 5S rRNA PROBES TO MOLLICUTES

| ORGANISM | ATCC NO. | PROBE SEQ ID NO. 22 RLU | PROBE SEQ ID NO. 23 RLU |
|---|---|---|---|
| Mycoplasma capricolum[a] | 23205 | 1,496 | 5,064 |
| Mycoplasma faucium[a] | 25293 | 1,466 | 6,218 |
| Mycoplasma fermentans[a] | 15474 | 2,017 | 10,572 |
| Mycoplasma gallisepticum | 19610 | 1,355 | 5,657 |
| Mycoplasma genitalium | 33530 | 1,233 | 4,721 |
| Mycoplasma muris[a] | 33757 | 5,640 | 12,462 |
| Mycoplasma iowae[a] | 33552 | 2,537 | 6,498 |
| Mycoplasma pirum[a] | 25960 | 1,674 | 7,354 |
| Mycoplasma lipophylum[a] | 27790 | 1,559 | 5,103 |
| Mycoplasma neurolyticum[a] | 19988 | 1,482 | 5,861 |
| Mycoplasma orale | 23714 | 1,697 | 4,362 |
| Mycoplasma pneumoniae[a] | 15531 | 2,129 | 7,514 |
| Mycoplasma primatum[a] | 15497 | 1,530 | 4,787 |
| Mycoplasma salivarium[a] | 23064 | 1,662 | 4,676 |
| Spiroplasma mirum[a] | 29335 | 2,815 | 7,227 |
| Ureaplasma urealyticum[a] | 27815 | 895,233 | 676,817 |
| Ureaplasma urealyticum[a] | 27619 | 1,679,357 | 1,449,564 |

[a]Whole cell lysates were tested at a concentration of $10^7$ cells per reaction.

Example 4

This example describes probes which can distinguish biotype 1 from biotype 2. In the course of probe development it was observed that one probe gave signals substantially lower for biotype 1 lysates than biotype 2 lysates. This suggested sequence variability in the probe region. To identify probe sequences targeted to a particular biotype several strains of *Ureaplasma urealyticum* were analyzed. Using the sequence information, biotype specific probes SEQ. ID. NOs. 121 and 122 were synthesized and labeled with acridinium ester. The probes were hybridized to rRNA from 18 strains of *Ureaplasma urealyticum* as described in Example 2 and the data is presented in Table 7. The signal obtained with the all-bacteria/yeast probe mix provides a quantitative indication of the amount of rRNA in each sample. The biotype 1 probe reacted only with biotype 1 strains; the biotype 2 probe reacted only with biotype 2 strains.

A similar experiment was performed to investigate the specificity of the biotype probes against 18 closely related Mycoplasma species and two Spiroplasma species. Results shown in Table 8 are the net RLU (i.e., the RLU from sample tested minus the RLU from a negative control sample). As seen in Table 8, the biotype-specific *Ureaplasma urealyticum* probes reacted only with their respective specific biotype strains and did not cross-react with any of the other closely related organisms.

TABLE 7

HYBRIDIZATION OF BIOTYPE PROBES

| | | PROBE, NET RLU | | |
|---|---|---|---|---|
| U. urealyticum ATCC NO. | Biotype | All-Bacteria/ Yeast | Biotype 1 | Biotype 2 |
| 27813 | 1 | 141,390 | 10,830 | 913 |
| 27815 | 1 | 95,249 | 60,145 | 130 |
| 27818 | 1 | 87,785 | 30,091 | 101 |
| 33697 | 1 | 83,584 | 77,891 | 130 |
| 27618 | 2 | 120,574 | 120 | 117,078 |

TABLE 7-continued

HYBRIDIZATION OF BIOTYPE PROBES

| U. urealyticum ATCC NO. | Biotype | PROBE, NET RLU | | |
|---|---|---|---|---|
| | | All-Bacteria/ Yeast | Biotype 1 | Biotype 2 |
| 27814 | 2 | 142,847 | 5 | 128,002 |
| 27816 | 2 | 112,627 | 89 | 148,618 |
| 27619 | 2 | 159,929 | 958 | 180,885 |
| 27817 | 2 | 69,874 | 108 | 69,151 |
| 27819 | 2 | 101,053 | 61 | 146,858 |
| 29557 | 2 | 113,125 | 143 | 128,480 |
| 29558 | 2 | 133,822 | 55 | 104,791 |
| 29559 | 2 | 92,546 | 644 | 150,724 |
| 33175 | 2 | 60,896 | 93 | 95,811 |
| 33695 | 2 | 122,517 | 106 | 143,790 |
| 33696 | 2 | 115,043 | 183 | 134,746 |
| 33698 | 2 | 112,323 | 3 | 125,216 |
| 33699 | 2 | 98,076 | 125 | 127,981 |

TABLE 8

SPECIFICITY OF BIOTYPE PROBES

| ORGANISM | ATCC NO. | PROBE, NET RLU | | |
|---|---|---|---|---|
| | | All-Bacteria/ Yeast | Biotype 1 | Biotype 2 |
| M. arginini | 23838 | 33,238 | 230 | −184 |
| M. arthritidis | 35943 | 141,240 | 82 | 82 |
| M. bovigenitalium | 19852 | 9,543 | 17 | 26 |
| M. bovis | 25523 | 70,824 | −111 | 96 |
| M. buccale | 23636 | 15,210 | −143 | 31 |
| M. californicum | 33461 | 113,936 | 77 | 26 |
| M. capricolum | 23205 | 50,103 | −97 | 95 |
| M. faucium | 25293 | 61,263 | 84 | 21 |
| M. fermentans | 15474 | 34,324 | 2 | −16 |
| M. gallisepticum | 19610 | 62,053 | −119 | 31 |
| M. genitalium | 33530 | 104,629 | 215 | −5 |
| M. pirum | 25960 | 59,082 | 106 | 93 |
| M. neurolyticum | 19988 | 17,383 | 95 | 72 |
| M. orale | 23715 | 29,103 | 22 | 113 |
| M. pneumoniae | 15531 | 34,329 | −161 | −94 |
| M. primatum | 15497 | 40,730 | −18 | 23 |
| M. salivarium | 23064 | 66,612 | −80 | −60 |
| M. hominis | 23114 | 46,680 | −58 | 36 |
| Sp. mirum | 29335 | 53,887 | −19 | 34 |
| Sp. MQ-1 | 33825 | 35,178 | −51 | 24 |
| U. urealy. bio. 1 | 27815 | 62,491 | 42,268 | 163 |
| U. urealy. bio. 2 | 27619 | 108,404 | 125 | 136,790 |

Example 5

This example illustrates the use of assay probes for Ureaplasma of the same sense as the target nucleic acid to detect the products of target nucleic acid amplification. *Ureaplasma urealyticum* rRNA was amplified by incubation at about 37° C. in 100 μL of a solution comprising 0.3 μM of a promoter-primer (SEQ. ID. No. 141), 50 mM Tris-HCl, pH 7.6, 25 mM KCl, 17.5 mM MgCl$_2$, 5 mM dithiothreitol, 2 mM spermidine trihydrochloride, 6.5 mM rATP, 2.5 mM rCTP, 6.5 mM rGTP, 2.5 mM rUTP, 0.2 mM DATP, 0.2 mM dCTP, 0.2 mM dGTP, 0.2 mM dTTP, 600 U MuMLV reverse transcriptase and 400 U T7 RNA polymerase (Kacian et al., supra, entitled "Nucleic Acid Sequence Amplification Method, Composition, and Kit"). The reaction was monitored by removing aliquots at various time points between 15 minutes and 4 hours and assaying for the product using two 5S rRNA probes of the same sense as the target rRNA (SEQ. ID. Nos. 59, 110) and helper probes (SEQ. ID. Nos. 104, 107) using conditions described in Example 2.

TABLE 9

| Time of Incubation | RLU | |
|---|---|---|
| | 1 fmol target | 0.1 fmol target |
| 15 min | 5,389 | 307 |
| 30 min | 10,360 | 778 |
| 60 min | 40,622 | 5,588 |
| 120 min | 144,851 | 13,051 |
| 180 min | 192,618 | 16,249 |
| 240 min | 203,393 | 20,745 |

The data shown in Table 9 demonstrates the ability of assay probes targeted to nucleic acid sequences of the opposite sense as the rRNA of the organism to detect the product from a target amplification procedure. As the amplification time increased, more target sequence was produced resulting in increased signal from probe detection.

The data shown in the various examples described above confirm that the novel probes herein described and claimed are capable of distinguishing Ureaplasma from its known nearest phylogenetic neighbors. The data also demonstrates that probes have been designed which can be used to distinguish Ureaplasma biotypes from each other and from nearest known phylogenetic neighbors. Furthermore, complementary oligonucleotide probes, i.e., those having the same sense as the target, are utilized to detect the products of target amplification procedures now being utilized to increase the detection sensitivity of assays for organisms.

Other embodiments are within the following claims.

---

What is claimed is:

1. A hybridization assay probe 10 to 100 nucleotides in length comprising an oligonucleotide sufficiently complementary to a *Ureaplasma urealyticum* target nucleic acid sequence to form a detectable probe:target hybrid with said *Ureaplasma urealyticum* target nucleic acid sequence under stringent hybridization assay conditions, wherein said *Ureaplasma urealyticum* target nucleic acid sequence is selected from the group consisting of SEQ ID NO: 31: ACCUCUCAGU ACAGCUACGC G,
SEQ ID NO: 33: CGCGUAGCUG UACUGAGAGG U,
SEQ ID NO: 37: CGUUAAGCAU CUAGAUUUAA UACCAAACUU ACAAACCCG,
SEQ ID NO: 39: CGGGUUUGUA AGUUUGGUAU UAAAUCUAGA UGCUUAACG,
SEQ ID NO: 40: CCUACUACAC UCUAGGUUUA CAGUUUUUGA UACAGCUAGA,
SEQ ID NO: 42: UCUAGCUGUA UCAAAAACUG UAAACCUAGA GUGUAGUAGG,
SEQ ID NO: 43: GUCAGUGAUA GUCCAAGUUG GC,
SEQ ID NO: 45: GCCAACUUGG ACUAUCACUG AC,
SEQ ID NO: 61: CAGUAAUCUA AUUCUCAUUA GACUGAGUUU CCUCAUUCG,
SEQ ID NO: 63: CGAAUGAGGA AACUCAGUCU AAUGAGAAUU AGAUUACUG,
SEQ ID NO; 109: GGAUGGGAAC AGGUAUUUCC ACUCUGAUAU GAUCAC, and
SEQ ID NO: 111: GUGAUCAUAU CAGAGUGGAA AUACCUGUC CCAUCC;
    wherein under said stringent hybridization assay conditions said hybridization assay probe does not form a detectable probe:non-target hybrid with nucleic acid from *Mycoplasma hominis*.

2. The hybridization assay probe of claim 1, wherein said hybridization assay probe also does not form said detectable probe:non-target hybrid with nucleic acid from *Mycoplasma genizalium* and *Mycoplasma pneumoniae*.

3. The hybridization assay probe of claim 1, wherein said hybridizaton assay probe also does not form said detectable probe:non-target hybrid with nucleic acid from *Mycoplasma orale, Mycoplasma fermentans, Mycoplasma capricolum, Mycoplasma lipophilum,* and *Mycoplasma salivarium*.

4. The hybridization assay probe of claim 2, wherein said target *Ureaplasma urealyticum* nucleic acid sequence is selected from the group consisting of SEQ ID NO: 31 and SEQ ID NO: 33.

5. The hybridization assay probe of claim 2, wherein said target *Ureaplasma urealyticum* nucleic acid sequence is selected from the group consisting of SEQ ID NO: 37 and SEQ ID NO: 39.

6. The hybridization assay probe of claim 2, wherein said target *Ureaplasma urealyticum* nucleic acid sequence is selected from the group consisting of SEQ ID NO: 40 and SEQ ID NO: 42.

7. The hybridization assay probe of claim 2, wherein said target *Ureaplasma urealyticum* nucleic acid sequence is selected from the group consisting of SEQ ID NO: 43 and SEQ ID NO: 45.

8. The hybridization assay probe of claim 2, wherein said target *Ureaplasma urealyticum* nucleic acid sequence is selected from the group consisting of SEQ ID NO: 61 and SEQ ID NO: 63.

9. The hybridization assay probe of claim 2, wherein said target *Ureaplasma urealyticum* nucleic acid sequence is selected from the group consisting of SEQ ID NO: 109 and SEQ ID NO: 111.

10. A hybridization assay probe for detecting Ureaplasma under stringent hybridization assay conditions which is 21 to 100 nucleotides in length and comprises a nucleotide base sequence selected from the group consisting of:

SEQ ID NO: 2: ACCTCTCAGT ACAGCTACGC G,
SEQ ID NO: 8: CGTTAAGCAT CTAGATTTAA TACCAAACTT ACAAACCCG,
SEQ ID NO: 9: CCTACTACAC TCTAGGTTTA CAGTTTTTGA TACAGCTAGA,
SEQ ID NO: 11: CTCAGTGATA GTCCAAGTTG GC,
SEQ ID NO: 20: CGATTTTGCA GCAGTTTGTA TTAGCCATTG,
SEQ ID NO: 26: GGATGGGAAC AGGTATTTCC ACTCTGATAT GATCAC,
SEQ ID NO: 29: CAGTAATCTA ATTCTCATTA GACTGAGTTT CCTCATTCG,
SEQ ID NO: 31: ACCUCUCAGU ACAGCUACGC G,
SEQ ID NO: 32: CGCGTAGCTG TACTGAGAGG T,
SEQ ID NO: 33: CGCGUAGCUG UACUGAGAGG U,
SEQ ID NO: 37: CGUUAAGCAU CUAGAUUUAA UACCAAACUU ACAAACCCG,
SEQ ID NO: 38: CGGGTTTGTA AGTTTGGTAT TAAATCTAGA TGCTTAACG,
SEQ ID NO: 39: CGGGUUUGUA AGUUUGGUAU UAAAUCUAGA UGCUUAACG,
SEQ ID NO: 40: CCUACUACAC UCUAGGUUUA CAGUUUUUGA UACAGCUAGA,
SEQ ID NO: 41: TCTAGCTGTA TCAAAAACTG TAAACCTAGA GTGTAGTAGG,
SEQ ID NO: 42: UCUAGCUGUA UCAAAAACUG UAAACCUAGA GUGUAGUAGG,
SEQ ID NO: 43: GUCAGUGAUA GUCCAAGUUG GC,
SEQ ID NO: 44: GCCAACTTGG ACTATCACTG AC,
SEQ ID NO: 45: GCCAACUUGG ACUAUCACUG AC,
SEQ ID NO: 52: CGAUUUUGCA GCAGUUUGUA UUAGCCAUUG,
SEQ ID NO: 53: CAATGGCTAA TACAAACTGC TGCAAAATCG,
SEQ ID NO: 61: CAGUAAUCUA AUUCUCAUUA GACUGAGUUU CCUCAUUCG,
SEQ ID NO: 62: CGAATGAGGA AACTCAGTCT AATGAGAATT AGATTACTG,
SEQ ID NO: 63: CGAAUGAGGA AACUCAGUCU AAUGAGAAUU AGAUUACUG,

SEQ ID NO: 109: GGAUGGGAAC AGGUAUUUCC ACUCUGAUAU GAUCAC,

SEQ ID NO: 110: GTGATCATAT CAGAGTGGAA ATACCTGTTC CCATCC, and

SEQ ID NO: 111 GUGAUCAUAU CAGAGUGGAA AUACCUGUUC CCAUCC;

wherein said hybridization assay probe hybridizes to *Ureaplasma urealyticum* nucleic acid to form a detectable probe:target hybrid under stringent hybridization assay conditions, but does not hybridize to nucleic acid from *Mycoplasma genitalium, Mycoplasma hominis* and *Mycoplasma pneumoniae* to form a detectable probe:non-target hybrid under said stringent hybridization assay conditions.

11. The hybridization assay probe of claim 10, wherein said nucleotide base sequence is selected from the group consisting of SEQ ID NO: 2, SEQ ID NO: 31, SEQ ID NO: 32, and SEQ ID NO: 33.

12. The hybridization assay probe of claim 10, wherein said nucleotide base sequence is selected from the group consisting of SEQ ID NO: 8, SEQ ID NO: 37, SEQ ID NO: 38, and SEQ ID NO: 39.

13. The hybridization assay probe of claim 10, wherein said nucleotide base sequence is selected from the group consisting of SEQ ID NO: 9, SEQ ID NO: 40, SEQ ID NO: 41, and SEQ ID NO: 42.

14. The hybridization assay probe of claim 10, wherein said nucleotide base sequence is selected from the group consisting of SEQ ID NO: 11, SEQ ID NO: 43, SEQ ID NO: 44, and SEQ ID NO: 45.

15. The hybridization assay probe of claim 10, wherein said nucleotide base sequence is selected from the group consisting of SEQ ID NO: 20, SEQ ID NO: 52, and SEQ ID NO: 53.

16. The hybridization assay probe of claim 10, wherein said nucleotide base sequence is selected from the group consisting of SEQ ID NO: 26, SEQ ID NO: 109, SEQ ID NO: 110, and SEQ ID NO: 111.

17. The hybridization assay probe of claim 10, wherein said nucleotide base sequence is selected from the group consisting of SEQ ID NO: 29, SEQ ID NO: 61, SEQ ID NO: 62, and SEQ ID NO: 63.

18. The hybridization assay probe of any one of claims 11, 12, 13, 14, 15, 16, and 17, wherein said hybridization assay probe consists of said nucleotide base sequence and one or more reporter groups.

19. A hybridization assay probe 10 to 100 nucleotides in length comprising an oligonucleotide sufficiently complementary to a *Ureaplasma urealyticum* biotype specific target nucleic acid sequence to form a detectable probe:target hybrid under stringent hybridization assay conditions with either *Ureaplasma urealyticum* biotype 1 nucleic acid or *Ureaplasma urealyticum* biotype 2 nucleic acid, wherein said hybridization assay probe does not form said detectable probe:target hybrid with both *Ureaplasma urealyticum* biotype 1 nucleic acid and *Ureaplasma urealyticum* biotype 2 nucleic acid under said stringent hybridization assay conditions, said biotype specific target nucleic acid sequence being selected from the group consisting of:

SEQ ID NO: 126: CAACACCGAC UCGUUCGAGC,

SEQ ID NO: 127: CAACACCGAC CCAUUCGG,

SEQ ID NO: 136: GCUCGAACGA GUCGGUGUUG, and

SEQ ID NO: 137: CCGAAUGGGU CGGUGUUG; and wherein said hybridization assay probe does not hybridize to nucleic acid from *Mycoplasma genitalium,* *Mycoplasma hominis* and *Mycoplasma pneumoniae* to form a detectable probe:non-target hybrid under said stringent hybridization assay conditions.

20. The probe of claim 19, wherein said biotype specific target nucleic acid sequence is either SEQ ID NO: 126 or SEQ ID NO: 136.

21. The probe of claim 19, wherein said biotype specific target nucleic acid sequence is either SEQ ID NO: 127 or SEQ ID NO: 137.

22. A hybridization assay probe for distinguishing between different *Ureaplasma urealyticum* biotypes which is 20 to 100 nucleotides in length and comprises a nucleotide base sequence selected from the group consisting of:

SEQ ID NO: 121: CAACACCGAC TCGTTCGAGC,

SEQ ID NO: 126: CAACACCGAC UCGUUCGAGC,

SEQ ID NO: 131: GCTCGAACGA GTCGGTGTTG, and

SEQ ID NO: 136: GCUCGAACGA GUCGGUGUUG;

provided that under stringent hybridization assay conditions said hybridization assay probe hybridizes with *Ureaplasma urealyticum* biotype 2 nucleic acid to form a detectable probe:target hybrid, and said hybridization assay probe does not form said detectable probe:target hybrid with *Ureaplasma urealyticum* biotype 1 nucleic acid under said stringent hybridization assay conditions, further provided that said hybridization assay probe does not hybridize to nucleic acid from *Mycoplasma genitalium, Mycoplasma hominis* and *Mycoplasma pneumoniae* to form a detectable probe:non-target hybrid under said stringent hybridization assay conditions.

23. The probe of claim 22, wherein said hybridization assay probe consists of said nucleotide base sequence and one or more reporter groups.

24. A hybridization assay probe for distinguishing between different *Ureaplasma urealyticum* biotypes which is 18 to 100 nucleotides in length and comprises a nucleotide base sequence selected from the group consisting of

SEQ ID NO: 122: CAACACCGAC CCATTCGG,

SEQ ID NO: 127: CAACACCGAC CCAUUCGG,

SEQ ID NO: 132: CCGAATGGGT CGGTGTTG, and

SEQ ID NO: 137: CCGAAUGGGU CGGUGUUG provided that under stringent hybridization assay conditions said hybridization assay probe hybridizes with *Ureaplasma urealyticum* biotype 1 nucleic acid to form a detectable probe:target hybrid, and said hybridization assay probe does not form said detectable probe:target hybrid with *Ureaplasma urealyticum* biotype 2 nucleic acid under said stringent hybridization assay conditions, further provided that said hybridization assay probe does not hybridize to nucleic acid from *Mycoplasma genitalium, Mycoplasma hominis* and *Mycoplasma pneumoniae* to form a detectable probe:non-target hybrid under said stringent hybridization assay conditions.

25. The probe of claim 24, wherein said hybridization assay probe consists of said nucleotide base sequence and one or more reporter groups.

26. A probe mix comprising:

a) a hybridization assay probe for detecting Ureaplasma under stringent hybridization assay conditions which is 21 to 100 nucleotides in length and comprises a nucleotide base sequence selected from the group consisting of:

SEQ ID NO: 2: ACCTCTCAGT ACAGCTACGC G,

SEQ ID NO: 8: CGTTAAGCAT CTAGATTTAA TAC-
CAAACTT ACAAACCCG,

SEQ ID NO: 9: CCTACTACAC TCTAGGTTTA
CAGTTTTTGA TACAGCTAGA,

SEQ ID NO: 11: GTCAGTGATA GTCCAAGTTG
GC,

SEQ ID NO: 20: CGATTTTGCA GCAGTTTGTA
TTAGCCATTG,

SEQ ID NO: 26: GGATGGGAAC AGGTATTTCC
ACTCTGATAT GATCAC,

SEQ ID NO: 29: CAGTAATCTA ATTCTCATTA
GACTGAGTTT CCTCATTCG,

SEQ ID NO: 31: ACCUCUCAGU ACAGCUACGC
G,

SEQ ID NO: 32: CGCGTAGCTG TACTGAGAGG T,

SEQ ID NO: 33: CGCGUAGCUG UACUGAGAGG
U,

SEQ ID NO: 37: CGUUAAGCAU CUAGAUUUAA
UACCAAACUU ACAAACCCG,

SEQ ID NO: 38: CGGGTTTGTA AGTTTGGTAT
TAAATCTAGA TGCTTAACG,

SEQ ID NO: 39: CGGGUUUGUA AGUTUGGUAU
UAAAUCUAGA UGCUUAACG,

SEQ ID NO: 40: CCUACUACAC UCUAGGUUUA
CAGUUUUGA UACAGCUAGA,

SEQ ID NO: 41: TCTAGCTGTA TCAAAAACTG
TAAACCTAGA GTGTAGTAGG,

SEQ ID NO: 42: UCUAGCUUGUA UCAAAAACUG
UAAACCUAGA GUGUAGUAGG,

SEQ ID NO: 43: GUCAGUGAUA GUCCAAGUUG
GC,

SEQ ID NO: 44: GCCAACTTGG ACTATCACTG
AC,

SEQ ID NO: 45: GCCAACUUGG ACUAUCACUG
AC,

SEQ ID NO: 52: CGAUUUUGCA GCAGUUUGUA
UUAGCCAUUG,

SEQ ID NO: 53: CAATGGCTAA TACAAACTGC
TGCAAAATCG,

SEQ ID NO: 61: CAGUAAUCUA AUUCUCAUUA
GACUGAGUU CCUCAUUCG,

SEQ ID NO: 62: CGAATGAGGA AACTCAGTCT
AATGAGAATT AGATTACTG,

SEQ ID NO: 63: CGAAUGAGGA AACUCAGUCU
AAUGAGAAUU AGAUUACUG,

SEQ ID NO: 109: GGAUGGGAAC AGGUAUUUCC
ACUCUGAUAU GAUCAC,

SEQ ID NO: 110: GTGATCATAT CAGAGTGGAA
ATACCTGTTC CCATCC, and

SEQ ID NO: 111: GUGAUCAUAU CAGAGUGGAA
AUACCUGUUC CCAUCC;

wherein under stringent hybridization assay conditions
said hybridization assay probe forms a detectable pro-
be:target hybrid with *Ureaplasma urealyticum* nucleic
acid, but does not form a detectable probe:non-target
hybrid with nucleic acid from *Mycoplasma genitalium,
Mycoplasma hominis* and *Mycoplasma pneumoniae*
under said stringent hybridization assay conditions; and b) a helper probe.

27. The probe mix of claim 26, wherein said hybridization
assay probe comprises a nucleotide base sequence selected
from the group consisting of SEQ ID NO: 2, SEQ ID NO:
31, SEQ ID NO: 32, and SEQ ID NO: 33; and said helper
probe comprises a nucleotide base sequence selected from
the group consisting of:

SEQ ID NO: 1: TCATTGACTT GGTGAGCCAT
TACCTCAC,

SEQ ID NO: 3: GCCGTGTCTC AGTCCCATTG
TGGCTGTTCT,

SEQ ID NO: 64: UCAUUGACUU GGUGAGCCAU
UACCUCAC,

SEQ ID NO: 65: GTGAGGTAAT GGCTCACCAA
GTCAATGA,

SEQ ID NO: 66: GUGAGGUAAU GGCUCACCAA
GUCAAUGA,

SEQ ID NO: 67: GCCGUGUCUC AGUCCCAUUG
UGGCUGUUCU,

SEQ ID NO: 68: AGAACAGCCA CAATGGGACT
GAGACACGGC, and

SEQ ID NO: 69: AGAACAGCCA CAAUGGGACU
GAGACACGGC.

28. The probe mix of claim 27, wherein said probe mix is
selected from the group consisting of:

(a) a probe mix comprising
a hybridization assay probe consisting of one or more
reporter groups and the nucleotide base sequence of
either SEQ ID NO: 2 or SEQ ID NO: 31;
a first helper probe consisting of the nucleotide base
sequence of either SEQ ID NO: 1 or SEQ ID NO: 64;
and
a second helper probe consisting of the nucleotide base
sequence of either SEQ ID NO: 3 or SEQ ID NO: 67;
and (b) a probe mix comprising
a hybridization assay probe consisting of one or more
reporter groups and the nucleotide base sequence of
either SEQ ID NO: 32 or SEQ ID NO: 33;
a first helper probe consisting of the nucleotide base
sequence of either SEQ ID NO: 65 or SEQ ID NO:
66; and
a second helper probe consisting of the nucleotide base
sequence of either SEQ ID NO: 68 or SEQ ID NO:
69.

29. A probe mix comprising:

a) a hybridization assay probe for detecting Ureaplasma
under stringent hybridization assay conditions which is
up to 100 nucleotides in length and comprises a nucle-
otide base sequence selected from the group consisting
of SEQ ID NO: 5, SEQ ID NO: 34, SEQ ID NO: 35,
and SEQ ID NO: 36; wherein under stringent hybrid-
ization assay conditions said hybridization assay probe
forms a detectable probe:target hybrid with *Urea-
plasma urealyticum* nucleic acid, but does not form a
detectable probe:non-target hybrid with nucleic acid
from *Mycoplasma genitalium, Mycoplasma hominis*
and *Mycoplasma pneumoniae* under said stringent
hybridization assay conditions; and b) a helper probe comprising a nucleotide base sequence
selected from the group consisting of:

SEQ ID NO: 4: ATATAAAAGA ACTTTACAAT
CTATAAGACC TTCATCGTTC ACGCGGC,

SEQ ID NO: 70: AUAUAAAAGA ACUUUACAAU
CUAUAAGACC UUCAUCGUUC ACGCGGC,

SEQ ID NO: 71: GCCGCGTGAA CGATGAAGGT
CTTATAGATT GTAAAGTTCT TTTATAT, and

SEQ ID NO: 72: GCCGCGUGAA CGAUGAAGGU
CUUAUAGAUU GUAAAGUUCU UUUAUAU.

30. The probe mix of claim 29, wherein said probe mix is
selected from the group consisting of:

(a) a probe mix comprising
a hybridization assay probe consisting of one or more
reporter groups and the nucleotide base sequence of
either SEQ ID NO: 5 or SEQ ID NO: 34;

a first helper probe consisting of the nucleotide base sequence of either SEQ ID NO: 4 or SEQ ID NO: 70; and a second helper probe consisting of the nucleotide base sequence of either SEQ ID NO: 6 or SEQ ID NO: 73; and (b) a probe mix comprising a hybridization assay probe consisting of one or more reporter groups and the nucleotide base sequence of either SEQ ID NO: 35 or SEQ ID NO: 36;

a first helper probe consisting of the nucleotide base sequence of either SEQ ID NO: 71 or SEQ ID NO: 72; and a second helper probe consisting of the nucleotide base sequence of either SEQ ID NO: 74 or SEQ ID NO: 75.

31. The probe mix of claim 26, wherein said hybridization assay probe comprises a nucleotide base sequence selected from the group consisting of SEQ ID NO: 8, SEQ ID NO: 37, SEQ ID NO: 38, and SEQ ID NO: 39; and said helper probe comprises a nucleotide base sequence selected from the group consisting of:

SEQ ID NO: 7: CCTGCGCTCG TTTTACGCCC AGTAAATCCG GATAACGC,

SEQ ID NO: 9: CCTACTACAC TCTAGGTTTA CAGTTTTTGA TACAGCTAGA,

SEQ ID NO: 40: CCUACUACAC UCUAGGUUUA CAGUUUUUGA UACAGCUAGA,

SEQ ID NO: 41: TCTAGCTGTA TCAAAAACTG TAAACCTAGA GTGTAGTAGG,

SEQ ID NO: 42: UCUAGCUGUA UCAAAAACUG UAAACCUAGA GUGUAGUAGG,

SEQ ID NO: 76: CCUGCGCUCG UUUUACGCCC AGUAAAUCCG GAUAACGC,

SEQ ID NO: 77: GCGTTATCCG GATTTACTGG GCGTAAAACG AGCGCAGG, and

SEQ ID NO: 78: GCGUUAUCCG GAUUUACUGG GCGUAAAACG AGCGCAGG.

32. The probe mix of claim 31, wherein said probe mix is selected from the group consisting of:

(a) a probe mix comprising a hybridization assay probe consisting of one or more reporter groups and the nucleotide base sequence of either SEQ ID NO: 8 or SEQ ID NO: 37;

a first helper probe consisting of the nucleotide base sequence of either SEQ ID NO: 7 or SEQ ID NO: 76; and a second helper probe consisting of the nucleotide base sequence of either SEQ ID NO: 9 or SEQ ID NO: 40; and (b) a probe mix comprising a hybridization assay probe consisting of one or more reporter groups and the nucleotide base sequence of either SEQ ID NO: 38 or SEQ ID NO: 39;

a first helper probe consisting of the nucleotide base sequence of either SEQ ID NO: 77 or SEQ ID NO: 78; and a second helper probe consisting of the nucleotide base sequence of either SEQ ID NO: 41 or SEQ ID NO: 42.

33. The probe mix of claim 26, wherein said hybridization assay probe comprises a nucleotide base sequence selected from the group consisting of SEQ ID NO: 9, SEQ ID NO: 40, SEQ ID NO: 41, and SEQ ID NO: 42; and said helper probe comprises a nucleotide base sequence selected from the group consisting of:

SEQ ID NO: 8: CGTTAAGCAT CTAGATTTAA TACCAAACTT ACAAACCCG,

SEQ ID NO: 10: GCCTTCGCCA CCGGTGTTCT TCCATATATC TA,

SEQ ID NO: 37: CGUUAAGCAU CUAGAUUUAA UACCAAACUU ACAAACCCG,

SEQ ID NO: 38: CGGGTTTGTA AGTTTGGTAT TAAATCTAGA TGCTTAACG,

SEQ ID NO: 39: CGGGUUUGUA AGUUUGGUAU UAAAUCUAGA UGCUUAACG,

SEQ ID NO: 79: GCCUUCGCCA CCGGUGUUCU UCCAUAUAUC UA,

SEQ ID NO: 80: TAGATATATG GAAGAACACC GGTGGCGAAG GC, and

SEQ ID NO: 81: UAGAUAUAUG GAAGAACACC GGUGGCGAAG GC.

34. The probe mix of claim 33, wherein said probe mix is selected from the group consisting of:

(a) a probe mix comprising a hybridization assay probe consisting of one or more reporter groups and the nucleotide base sequence of either SEQ ID NO: 9 or SEQ ID NO: 40;

a first helper probe consisting of the nucleotide base sequence of either SEQ ID NO: 8 or SEQ ID NO: 37; and a second helper probe consisting of the nucleotide base sequence of either SEQ ID NO: 10 or SEQ ID NO: 79; and (b) a probe mix comprising a hybridization assay probe consisting of one or more reporter groups and the nucleotide base sequence of either SEQ ID NO: 41 or SEQ ID NO: 42;

a first helper probe consisting of the nucleotide base sequence of either SEQ ID NO: 38 or SEQ ID NO: 39; and a second helper probe consisting of the nucleotide base sequence of either SEQ ID NO: 80 or SEQ ID NO: 81.

35. The probe mix of claim 26, wherein said hybridization assay probe comprises a nucleotide base sequence selected from the group consisting of SEQ ID NO: 11, SEQ ID NO: 43, SEQ ID NO: 44, and SEQ ID NO: 45; and said helper probe comprises a nucleotide base sequence selected from the group consisting of:

SEQ ID NO: 10: GCCTTCGCCA CCGGTGTTCT TCCATATATC TA,

SEQ ID NO: 12: CTAATCCTAT TTGCTCCCCA CACTTTCGAG CCTAAGC,

SEQ ID NO: 79: GCCUUCGCCA CCGGUGUUCU UCCAUAUAUC UA,

SEQ ID NO: 80: TAGATATATG GAAGAACACC GGTGGCGAAG GC,

SEQ ID NO: 81: UAGAUAUAUG GAAGAACACC GGUGGCGAAG GC,

SEQ ID NO: 82: CUAAUCCUAU UUGCUCCCCA CACUUUCGAG CCUAAGC,

SEQ ID NO: 83: GCTTAGGCTC GAAAGTGTGG GGAGCAAATA GGATTAG, and

SEQ ID NO: 84: GCUUAGGCUC GAAAGUGUGG GGAGCAAAUA GGAUUAG.

36. The probe mix of claim 35, wherein said probe mix is selected from the group consisting of:

(a) a probe mix comprising a hybridization assay probe consisting of one or more reporter groups and the nucleotide base sequence of either SEQ ID NO: 11 or SEQ ID NO: 43;

a first helper probe consisting of the nucleotide base sequence of either SEQ ID NO: 10 or SEQ ID NO: 79; and a second helper probe consisting of the nucleotide base sequence of either SEQ ID NO: 12 or SEQ ID NO: 82; and (b) a probe mix comprising a hybridization assay probe consisting of one or more reporter groups and the nucleotide base sequence of either SEQ ID NO: 44 or SEQ ID NO: 45;

a first helper probe consisting of the nucleotide base sequence of either SEQ ID NO: 80 or SEQ ID NO: 81; and a second helper probe consisting of the nucleotide base sequence of either SEQ ID NO: 83 or SEQ ID NO: 84.

37. The probe mix of claim 26, wherein said hybridization assay probe comprises a nucleotide base sequence selected from the group consisting of SEQ ID NO: 20, SEQ ID NO: 52, SEQ ID NO: 53, and SEQ ID NO: 54; and said helper probe comprises a nucleotide base sequence selected from the group consisting of:

SEQ ID NO: 19: TAGCACGTTT GCAGCCCTAG ATATAAGGGG CATGATG,

SEQ ID NO: 21: CGAATTGCAG CCCTCTATCC GAACTGAGAC TAACTTTTTC TG,

SEQ ID NO: 97: UAGCACGUUU GCAGCCCUAG AUAUAAGGGG CAUGAUG,

SEQ ID NO: 98: CATCATGCCC CTTATATCTA GGGCTGCAAA CGTGCTA,

SEQ ID NO: 99: CAUCAUGCCC CUUAUAUCUA GGGCUGCAAA CGUGCUA,

SEQ ID NO: 100: CGAAUUGCAG CCCUCUAUCC GAACUGAGAC UAACUUUUUC UG,

SEQ ID NO: 101: CAGAAAAAGT TAGTCTCAGT TCGGATAGAG GGCTGCAATT CG, and,

SEQ ID NO: 102: CAGAAAAAGU UAGUCUCAGU UCGGAUAGAG GGCUGCAAUU CG.

38. The probe mix of claim wherein 37, said probe mix is selected from the group consisting of:

(a) a probe mix comprising a hybridization assay probe consisting of one or more reporter groups and the nucleotide base sequence of either SEQ ID NO: 20 or SEQ ID NO: 52;

a first helper probe consisting of the nucleotide base sequence of either SEQ ID NO: 19 or SEQ ID NO: 97; and a second helper probe consisting of the nucleotide base sequence of either SEQ ID NO: 21 or SEQ ID NO: 100; and (b) a probe mix comprising a hybridization assay probe consisting of one or more reporter groups and the nucleotide base sequence of either SEQ ID NO: 53 or SEQ ID NO: 54;

a first helper probe consisting of the nucleotide base sequence of either SEQ ID NO: 98 or SEQ ID NO: 99; and a second helper probe consisting of the nucleotide base sequence of either SEQ ID NO: 101 or SEQ ID NO: 102.

39. The probe mix of claim 26, wherein said hybridization assay probe comprises a nucleotide base sequence selected from the group consisting of SEQ ID NO: 29, SEQ ID NO: 61, SEQ ID NO: 62, and SEQ ID NO: 63; and said helper probe comprises a nucleotide base sequence selected from the group consisting of:

SEQ ID NO: 28: GAGATCAACG GATTAAAGCC TCTTATCAGC TACCCGTTGC TTATCGCAGA TTAGCACG,

SEQ ID NO: 30: CACTTCACCA GGTATCGCTC TGTTAAACTA TGAATTCATT TATA,

SEQ ID NO: 115: GAGAUCAACG GAUUAAAGCC UCUUAUCAGC UACCCGUUGC UUAUCGCAGA UUAGCACG,

SEQ ID NO: 116: CGTGCTAATC TGCGATAAGC AACGGGTAGC TGATAAGAGG CTTTAATCCG TTGATCTC,

SEQ ID NO: 117: CGUGCUAAUC UGCGAUAAGC AACGGGUAGC UGAUAAGAGG CUUUAAUCCG UUGAUCUC,

SEQ ID NO: 118: CACUUCACCA GGUAUCGCUC UGUUAAACUA UGAAUUCAUU UAUA,

SEQ ID NO: 119: TATAAATGAA TTCATAGTTT AACAGAGCGA TACCTGGTGA AGTG, and

SEQ ID NO: 120: UAUAAAUGAA UUCAUAGUUU AACAGAGCGA UACCUGGUGA AGUG.

40. The probe mix of claim 39, wherein said probe mix is selected from the group consisting of:

(a) a probe mix comprising a hybridization assay probe consisting of one or more reporter groups and the nucleotide base sequence of either SEQ ID NO: 29 or SEQ ID NO: 61;

a first helper probe consisting of the nucleotide base sequence of either SEQ ID NO: 28 or SEQ ID NO: 115; and a second helper probe consisting of the nucleotide base sequence of either SEQ ID NO: 30 or SEQ ID NO: 118; and (a) a probe mix comprising a hybridization assay probe consisting of one or more reporter groups and the nucleotide base sequence of either SEQ ID NO: 62 or SEQ ID NO: 63;

a first helper probe consisting of the nucleotide base sequence of either SEQ ID NO: 116 or SEQ ID NO: 117; and a second helper probe consisting of the nucleotide base sequence of either SEQ ID NO: 119 or SEQ ID NO: 120.

41. A probe mix comprising a hybridization assay probe 18 to 100 nucleotides in length comprising a nucleotide base sequence selected from the group consisting of:

SEQ ID NO: 121: CAACACCGAC TCGTTCGAGC,

SEQ ID NO: 122: CAACACCGAC CCATTCGG,

SEQ ID NO: 126: CAACACCGAC UCGUUCGAGC,

SEQ ID NO: 127: CAACACCGAC CCAUUCGG,

SEQ ID NO: 131: GCTCGAACGA GTCGGTGTTG,

SEQ ID NO: 132: CCGAATGGGT CGGTGTTG,

SEQ ID NO: 136: GCUCGAACGA GUCGGUGUUG, and

SEQ ID NO: 137: CCGAAUGGGU CGGUGUUG;

provided that said hybridization assay probe forms a detectable probe:target hybrid under stringent hybridization assay conditions with either *Ureaplasma urealyticum* biotype 1 nucleic acid or *Ureaplasma urealyticum* biotype 2 nucleic acid, wherein said hybridization assay probe does not form said detectable probe:target hybrid with both *Ureaplasma urealyticum* biotype 1 nucleic acid and *Ureaplasma urealyticum* biotype 2 nucleic acid under said stringent hybridization assay conditions, further provided that said hybridization assay probe does not hybridize to nucleic acid from *Mycoplasma genitalium, Mycoplasma hominis* and *Mycoplasma pneumoniae* to form a detectable probe:non-target hybrid under said stringent hybridization assay conditions; and a helper probe comprising a nucleotide base sequence selected from the group consisting of:
SEQ ID NO: 123: CGACATTTAA TGATGATCGT TTACGGTGTG GAC,
SEQ ID NO: 124: GCCGACATTT AATGATGATC GTTTACGGTG TGGAC,
SEQ ID NO: 125: CCCAGGCACA TCATTTAATG CGTTAGCTA,
SEQ ID NO: 128: CGACAUUUAA UGAUGAUCGU UUACGGUGUG GAC,
SEQ ID NO: 129: GCCGACAUUU AAUGAUGAUC GUUUACGGUG UGGAC,
SEQ ID NO: 130: CCCAGGCACA UCAUUUAAUG CGUUAGCUA,
SEQ ID NO: 133: GTCCACACCG TAAACGATCA TCATTAAATG TCG,
SEQ ID NO: 134: GTCCACACCG TAAACGATCA TCATTAAATG TCGGC,
SEQ ID NO: 135: TAGCTAACGC ATTAAATGAT GTGCCTGGG,
SEQ ID NO: 138: GUCCACACCG UAAACGAUCA UCAUUAAAUG UCG,
SEQ ID NO: 139: GUCCACACCG UAAACGAUCA UCAUUAAAUG UCGGC, and
SEQ ID NO: 140: UAGCUAACGC AUUAAAUGAU GUGCCUGGG.

42. The probe mix of claim 41, wherein said probe mix is selected from the group consisting of:
(a) a probe mix comprising
a hybridization assay probe consisting of one or more reporter groups and the nucleotide base sequence of either SEQ ID NO: 121 or SEQ ID NO: 126,
a first helper probe consisting of the nucleotide base sequence of either SEQ ID NO: 123 or SEQ ID NO: 128; and
a second helper probe consisting of the nucleotide base sequence of either SEQ ID NO: 125 or SEQ ID NO: 130; and
(b) a probe mix comprising
a hybridization assay probe consisting of one or more reporter groups and the nucleotide base sequence of either SEQ ID NO: 131 or SEQ ID NO: 136;
a first helper probe consisting of the nucleotide base sequence of either SEQ ID NO: 133 or SEQ ID NO: 138; and
a second helper probe consisting of the nucleotide base sequence of either SEQ ID NO: 135 or SEQ ID NO: 140.

43. A probe mix selected from the group consisting of:
(a) a probe mix comprising
a hybridization assay probe consisting of one or more reporter groups and the nucleotide base sequence of either SEQ ID NO: 122 or SEQ ID NO: 127,
a first helper probe consisting of the nucleotide base sequence of either SEQ ID NO: 124 or SEQ ID NO: 129; and
a second helper probe consisting of the nucleotide base sequence of either SEQ ID NO: 125 or SEQ ID NO: 130; and (b) a probe mix comprising
a hybridization assay probe consisting of one or more reporter groups and the nucleotide base sequence of either SEQ ID NO: 132 or SEQ ID NO: 137;
a first helper probe consisting of the nucleotide base sequence of either SEQ ID NO: 134 or SEQ ID NO: 139; and
a second helper probe consisting of the nucleotide base sequence of either SEQ ID NO: 135 or SEQ ID NO: 140.

44. A probe mix comprising
a) a hybridization assay probe for detecting *Ureaplasma urealyticum* under stringent hybridization assay conditions which is 28 to 100 nucleotides in length and comprises a nucleotide base sequence selected from the group consisting of:
SEQ ID NO: 14: CGTTCGAGCC GACATTTAAT GATGATCG,
SEQ ID NO: 46: CGUUCGAGCC GACAUUUAAU GAUGAUCG,
SEQ ID NO: 47: CGATCATCAT TAAATGTCGG CTCGAACG, and
SEQ ID NO: 48: CGAUCAUCAU UAAAUGUCGG CUCGAACG;
wherein under said stringent hybridization assay conditions said hybridization assay probe forms a detectable probe:target hybrid with *Ureaplasma urealyticum* nucleic acid, but does not form a detectable probe:non-target hybrid with nucleic acid from *Mycoplasma genitalium, Mycoplasma hominis* and *Mycoplasma pneumoniae* under said stringent hybridization assay conditions; and
b) a helper probe consisting of a nucleotide base sequence selected from the group consisting of:
SEQ ID NO: 13: TTTACGGTGT GGACTACTAG GGTAT,
SEQ ID NO: 15: GCGTTAGCTA CAACACCGAC T,
SEQ ID NO: 85: UUUACGGUGU GGACUACUAG GGUAU,
SEQ ID NO: 86: ATACCCTAGT AGTCCACACC GTAAA,
SEQ ID NO: 87: AUACCCUAGU AGUCCACACC GUAAA,
SEQ ID NO: 88: GCGUUAGCUA CAACACCGAC U,
SEQ ID NO: 89: AGTCGGTGTT GTAGCTAACG C, and
SEQ ID NO: 90: AGUCGGUGUU GUAGCUAACG C.

45. The probe mix of claim 44, wherein said probe mix is selected from the group consisting of:
(a) a probe mix comprising
a hybridization assay probe consisting of one or more reporter groups and the nucleotide base sequence of either SEQ ID NO: 14 or SEQ ID NO: 46;
a first helper probe consisting of the nucleotide base sequence of either SEQ ID NO: 13 or SEQ ID NO: 85; and
a second helper probe consisting of the nucleotide base sequence of either SEQ ID NO: 15 or SEQ ID NO: 88; and
(b) a probe mix comprising
a hybridization assay probe consisting of one or more reporter groups and the nucleotide base sequence of either SEQ ID NO: 47 or SEQ ID NO: 48;
a first helper probe consisting of the nucleotide base sequence of either SEQ ID NO: 86 or SEQ ID NO: 87; and a second helper probe consisting of the nucleotide base sequence of either SEQ ID NO: 89 or SEQ ID NO: 90.

46. A probe mix comprising
a) a hybridization assay probe for detecting *Ureaplasma urealyticum* under stringent hybridization assay conditions which is 24 to 100 nucleotides in length and comprises a nucleotide base sequence selected from the group consisting of:
SEQ ID NO: 17: GCGTCGCAAT AGATGTCAAA CCTAG,
SEQ ID NO: 49: GCGUCGCAAU AGAUGUCAAA CCUAG,
SEQ ID NO: 50: CTAGGTTTGA CATCTATTGC GACGC, and
SEQ ID NO: 51: CUAGGUUUGA CAUCUAUUGC GACGC;
wherein under said stringent hybridization assay conditions said hybridization assay probe forms a detectable probe:target hybrid with a *Ureaplasma urealyticum* target nucleic acid, but does not form a detectable probe:non-target hybrid with nucleic acid from *Mycoplasma genitalium*, *Mycoplasma hominis* and *Mycoplasma pneumoniae* under said stringent hybridization assay conditions; and
b) a helper probe consisting of a nucleotide base sequence selected from the group consisting of:
SEQ ID NO: 16: GTAAGGTTCT ACGTGTATTG TCAAATTAAG CAACATGCTC CACCAC,
SEQ ID NO: 18: CGACAACCAT GCACCACCTG TCATATTGTT AACCTCAAC,
SEQ ID NO: 91: GUAAGGUUCU ACGUGUAUUG UCAAAUUAAG CAACAUGCUC CACCAC,
SEQ ID NO: 92: GTGGTGGAGC ATGTTGCTTA ATTTGACAAT ACACGTAGAA CCTTAC,
SEQ ID NO: 93: GUGGUGGAGC AUGUUGCUUA AUUUGACAAU ACACGUAGAA CCUUAC,
SEQ ID NO: 94: CGACAACCAU GCACCACCUG UCAUAUUGUU AACCUCAAC,
SEQ ID NO: 95: GTTGAGGTTA ACAATATGAC AGGTGGTGCA TGGTTGTCG, and
SEQ ID NO: 96: GUUGAGGUUA ACAAUAUGAC AGGUGGUGCA UGGUUGUCG.

47. The probe mix of claim 46, wherein said probe mix is selected from the group consisting of:
(a) a probe mix comprising
a hybridization assay probe consisting of one or more reporter groups and the nucleotide base sequence of either SEQ ID NO: 17 or SEQ ID NO: 49;
a first helper probe consisting of the nucleotide base sequence of either SEQ ID NO: 16 or SEQ ID NO: 91; and
a second helper probe consisting of the nucleotide base sequence of either SEQ ID NO: 18 or SEQ ID NO: 94; and
(b) a probe mix comprising
a hybridization assay probe consisting of one or more reporter groups and the nucleotide base sequence of either SEQ ID NO: 50 or SEQ ID NO: 51;
a first helper probe consisting of the nucleotide base sequence of either SEQ ID NO: 92 or SEQ ID NO: 93; and
a second helper probe consisting of the nucleotide base sequence of either SEQ ID NO: 95 or SEQ ID NO: 96.

48. A method for detecting the presence of Ureaplasma in a sample and distinguishing said Ureaplasma from *Mycoplasma genitalium*, *Mycoplasma pneumoniae*, and *Mycoplasma hominis* comprising the steps of:
a) providing to said sample a hybridization assay probe comprising an oligonucleotide which under stringent hybridization assay conditions hybridizes to a *Ureaplasma urealyticum* target nucleic acid selected from the group consisting of
SEQ ID NO: 31: ACCUCUCAGU ACAGCUACGC G,
SEQ ID NO: 33: CGCGUAGCUG UACUGAGAGG U,
SEQ ID NO: 37: CGUUAAGCAU CUAGAUUUAA UACCAAACUU ACAAACCCG,
SEQ ID NO: 39: CGGGUUUGUA AGUUUGGUAU UAAAUCUAGA UGCUUAACG,
SEQ ID NO: 40: CCUACUACAC UCUAGGUUUA CAGUUUUUGA UACAGCUAGA,
SEQ ID NO: 42: UCUAGCUGUA UCAAAAACUG UAAACCUAGA GUGUAGUAGG,
SEQ ID NO: 43: GUCAGUGAUA GUCCAAGUUG GC,
SEQ ID NO: 45: GCCAACUUGG ACUAUCACUG AC,
SEQ ID NO: 52: CGAUUUUGCA GCAGUUUGUA UUAGCCAUUG,
SEQ ID NO: 54: CAAUGGCUAA UACAAACUGC UGCAAAAUCG,
SEQ ID NO: 55: GCUAUUUUCG GCUCUAGAGU GCUUGACUUC UGUGUUCGGG AUG,
SEQ ID NO: 57: CAUCCCGAAC ACAGAAGUCA AGCACUCUAG AGCCGAAAAU AGC,
SEQ ID NO: 58: CGGCUCUAGA GUGCUUGACU UCUGUGUUCG,
SEQ ID NO: 60: CGAACACAGA AGUCAAGCAC UCUAGAGCCG,
SEQ ID NO: 61: CAGUAAUCUA AUUCUCAUUA GACUGAGUUU CCUCAUUCG,
SEQ ID NO: 63: CGAAUGAGGA AACUCAGUCU AAUGAGAAUU AGAUUACUG,
SEQ ID NO: 109: GGAUGGGAAC AGGUAUUUCC ACUCUGAUAU GAUCAC, and
SEQ ID NO: 111: GUGAUCAUAU CAGAGUGGAA AUACCUGUUC CCAUCC;
wherein under said stringent hybridization assay conditions said oligonucleotide hybridizes with said target nucleic acid to form a detectable probe:target hybrid and does not hybridize to form a detectable probe:non-target hybrid with *Mycoplasma genitalium*, *Mycoplasma hominis* and *Mycoplasma pneumoniae* nucleic acid under said stringent hybridization assay conditions; and
b) employing said stringent hybridization assay conditions and detecting the presence of said detectable probe:target hybrid formed under said stringent hybridization assay conditions as an indication that Ureaplasma may be present in said sample.

49. The method of claim 48, wherein target nucleic acid is selected from the group consisting of SEQ ID NO: 31 and SEQ ID NO: 33.

50. The method of claim 48, wherein said target nucleic acid is selected from the group consisting of SEQ ID NO: 37 and SEQ ID NO: 39.

51. The method of claim 48, wherein said target nucleic acid is selected from the group consisting of SEQ ID NO: 40 and SEQ ID NO: 42.

52. The method of claim 48, wherein said target nucleic acid is selected from the group consisting of SEQ ID NO: 43 and SEQ ID NO: 45.

53. The method of claim 48, wherein said target nucleic acid is selected from the group consisting of SEQ ID NO: 52 and SEQ ID NO: 54.

54. The method of claim 48, wherein said target nucleic acid is selected from the group consisting of SEQ ID NO: 55 and SEQ ID NO: 57.

55. The method of claim 48, wherein said target nucleic acid is selected from the group consisting of SEQ ID NO: 58 and SEQ ID NO: 60.

56. The method of claim 48, wherein said target nucleic acid is selected from the group consisting of SEQ ID NO: 61 and SEQ ID NO: 63.

57. The method of claim 48, wherein said target nucleic acid is selected from the group consisting of SEQ ID NO: 109 and SEQ ID NO: 111.

58. A method for detecting the presence of Ureaplasma in a sample and distinguishing said Ureaplasma from *Mycoplasma genitalium, Mycoplasma pneumoniae,* and *Mycoplasma hominis,* comprising the steps of:
   a) providing to said sample a hybridization assay probe comprising a detection nucleotide base sequence selected from the group consisting of:
   SEQ ID NO: 2: ACCTCTCAGT ACAGCTACGC G,
   SEQ ID NO: 8: CGTTAAGCAT CTAGATTTAA TACCAAACTT ACAAACCCG,
   SEQ ID NO: 9: CCTACTACAC TCTAGGTTTA CAGTTTTTGA TACAGCTAGA,
   SEQ ID NO: 11: GTCAGTGATA GTCCAAGTTG GC,
   SEQ ID NO: 20: CGATTTTGCA GCAGTTTGTA TTAGCCATTG,
   SEQ ID NO: 22: GCTATTTTCG GCTCTAGAGT GCTTGACTTC TGTGTTCGGG ATG,
   SEQ ID NO: 23: CGGCTCTAGA GTGCTTGACT TCTGTGTTCG,
   SEQ ID NO: 26: GGATGGGAAC AGGTATTTCC ACTCTGATAT GATCAC,
   SEQ ID NO: 29: CAGTAATCTA ATTCTCATTA GACTGAGTTT CCTCATTCG,
   SEQ ID NO: 31: ACCUCUCAGU ACAGCUACGC G,
   SEQ ID NO: 32: CGCGTAGCTG TACTGAGAGG T,
   SEQ ID NO: 33: CGCGUAGCUG UACUGAGAGG U,
   SEQ ID NO: 37: CGUUAAGCAU CUAGAUUUAA UACCAAACUU ACAAACCCG,
   SEQ ID NO: 38: CGGGTTTGTA AGTTTGGTAT TAAATCTAGA TGCTTAACG,
   SEQ ID NO: 39: CGGGUUUGUA AGUUUGGUAU UAAAUCUAGA UGCUUAACG,
   SEQ ID NO: 40: CCUACUACAC UCUAGGUUUA CAGUUUUUGA UACAGCUAGA,
   SEQ ID NO: 41: TCTAGCTGTA TCAAAAACTG TAAACCTAGA GTGTAGTAGG,
   SEQ ID NO: 42: UCUAGCUGUA UCAAAAACUG UAAACCUAGA GUGUAGUAGG,
   SEQ ID NO: 43: GUCAGUGAUA GUCCAAGUUG GC,
   SEQ ID NO: 44: GCCAACTTGG ACTATCACTG AC,
   SEQ ID NO: 45: GCCAACUUGG ACUAUCACUG AC,
   SEQ ID NO: 52: CGAUUUUGCA GCAGUUUGUA UUAGCCAUUG,
   SEQ ID NO: 53: CAATGGCTAA TACAAACTGC TGCAAAATCG,
   SEQ ID NO: 54: CAAUGGCUAA UACAAACUGC UGCAAAAUCG,
   SEQ ID NO: 55: GCUAUUUUCG GCUCUAGAGU GCUUGACUUC UGUGUUCGGG AUG,
   SEQ ID NO: 56: CATCCCGAAC ACAGAAGTCA AGCACTCTAG AGCCGAAAAT AGC,
   SEQ ID NO: 57: CAUCCCGAAC ACAGAAGUCA AGCACUCUAG AGCCGAAAAU AGC,
   SEQ ID NO: 58: CGGCUCUAGA GUGCUUGACU UCUGUGUUCG,
   SEQ ID NO: 59: CGAACACAGA AGTCAAGCAC TCTAGAGCCG,
   SEQ ID NO: 60: CGAACACAGA AGUCAAGCAC UCUAGAGCCG,
   SEQ ID NO: 61: CAGUAAUCUA AUUCUCAUUA GACUGAGUUU CCUCAUUCG,
   SEQ ID NO: 62: CGAATGAGGA AACTCAGTCT AATGAGAATT AGATTACTG,
   SEQ ID NO: 63: CGAAUGAGGA AACUCAGUCU AAUGAGAAUU AGAUUACUG,
   SEQ ID NO: 109: GGAUGGGAAC AGGUAUUUCC ACUCUGAUAU GAUCAC,
   SEQ ID NO: 110: GTGATCATAT CAGAGTGGAA ATACCTGTTC CCATCC, and
   SEQ ID NO: 111: GUGAUCAUAU CAGAGUGGAA AUACCUGUUC CCAUCC;
   wherein under stringent hybridization assay conditions said hybridization assay probe hybridizes with nucleic acid from *Ureaplasma urealyticum* to form a probe-:target hybrid and does not hybridize to nucleic acid from *Mycoplasma genitalium, Mycoplasma hominis* and *Mycoplasma pneumoniae* to form a detectable probe:non-target hybrid; and
   b) employing said stringent hybridization assay conditions and detecting the presence of said detectable probe:target hybrid formed under said stringent hybridization assay conditions as an indication that Ureaplasma may be present in said sample.

59. The method of claim 58, wherein said hybridization assay probe comprises a detection nucleotide base sequence selected from the group consisting of SEQ ID NO: 2, SEQ ID NO: 31, SEQ ID NO: 32, and SEQ ID NO: 33.

60. The method of claim 59, wherein said method uses one or more helper probes consisting of a nucleotide base sequence selected from the group consisting of:
   SEQ ID NO: 1: TCATTGACTT GGTGAGCCAT TACCTCAC,
   SEQ ID NO: 3: GCCGTGTCTC AGTCCCATTG TGGCTGTTCT,
   SEQ ID NO: 64: UCAUUGACUU GGUGAGCCAU UACCUCAC,
   SEQ ID NO: 65: GTGAGGTAAT GGCTCACCAA GTCAATGA,
   SEQ ID NO: 66: GUGAGGUAAU GGCUCACCAA GUCAAUGA,
   SEQ ID NO: 67: GCCGUGUCUC AGUCCCAUUG UGGCUGUUCU,
   SEQ ID NO: 68: AGAACAGCCA CAATGGGACT GAGACACGGC, and
   SEQ ID NO: 69: AGAACAGCCA CAAUGGGACU GAGACACGGC.

61. A method for detecting the presence of Ureaplasma in a sample and distinguishing said Ureaplasma from *Mycoplasma genitalium, Mycoplasma pneumoniae,* and *Mycoplasma hominis,* comprising the steps of:
   a) providing to said sample a hybridization assay probe comprising a detection nucleotide base sequence selected from the group consisting of: SEQ ID NO: 5, SEQ ID NO: 34, SEQ ID NO: 35, and SEQ ID NO: 36;

wherein under stringent hybridization assay conditions said hybridization assay probe hybridizes with nucleic acid from *Ureaplasma urealyticum* to form a probe:target hybrid and does not hybridize to nucleic acid from *Mycoplasma genitalium, Mycoplasma hominis* and *Mycoplasma pneumoniae* to form a detectable probe:non-target hybrid; and b) employing said stringent hybridization assay conditions and detecting the presence of said detectable probe:target hybrid formed under said stringent hybridization assay conditions as an indication that Ureaplasma may be present in said sample;

wherein said method uses one or more helper probes consisting of a nucleotide base sequence selected from the group consisting of:

SEQ ID NO: 4: ATATAAAAGA ACTTTACAAT CTATAAGACC TTCATCGTTC ACGCGGC,

SEQ ID NO: 6: GGCACATAGT TAGCCGATAC TTATTCAAAT GGTACAGTCA AA,

SEQ ID NO: 70: AUAUAAAAGA ACUUUACAAU CUAUAAGACC UUCAUCGUUC ACGCGGC,

SEQ ID NO: 71: GCCGCGTGAA CGATGAAGGT CTTATAGATT GTAAAGTTCT TTTATAT,

SEQ ID NO: 72: GCCGCGUGAA CGAUGAAGGU CUUAUAGAUU GUAAAGUUCU UUUAUAU,

SEQ ID NO: 73: GGCACAUAGU UAGCCGAUAC UUAUUCAAAU GGUACAGUCA AA,

SEQ ID NO: 74: TTTGACTGTA CCATTTGAAT AAGTATCGGC TAACTATGTG CC, and

SEQ ID NO: 75: UUUGACUGUA CCAUUUGAAU AAGUAUCGGC UAACUAUGUG CC.

62. The method of claim 58, wherein said hybridization assay probe comprises a detection nucleotide base sequence selected from the group consisting of SEQ ID NO: 8, SEQ ID NO: 37, SEQ ID NO: 38, and SEQ ID NO: 39.

63. The method of claim 62, wherein said method uses one or more helper probes consisting of a nucleotide base sequence selected from the group consisting of:

SEQ ID NO: 7: CCTGCGCTCG TTTTACGCCC AGTAAATCCG GATAACGC,

SEQ ID NO: 9: CCTACTACAC TCTAGGTTTA CAGTTTTTGA TACAGCTAGA,

SEQ ID NO: 40: CCUACUACAC UCUAGGUUUA CAGUUUUUGA UACAGCUAGA,

SEQ ID NO: 41: TCTAGCTGTA TCAAAAACTG TAAACCTAGA GTGTAGTAGG,

SEQ ID NO: 42: UCUAGCUGUA UCAAAAACUG UAAACCUAGA GUGUAGUAGG,

SEQ ID NO: 76: CCUGCGCUCG UUUUACGCCC AGUAAAUCCG GAUAACGC,

SEQ ID NO: 77: GCGTTATCCG GATTTACTGG GCGTAAAACG AGCGCAGG, and

SEQ ID NO: 78: GCGUUAUCCG GAUUUACUGG GCGUAAAACG AGCGCAGG.

64. The method of claim 58, wherein said hybridization assay probe comprises a detection nucleotide base sequence selected from the group consisting of SEQ ID NO: 9, SEQ ID NO: 40, SEQ ID NO: 41, and SEQ ID NO: 42.

65. The method of claim 64, wherein said method uses one or more helper probes consisting of a nucleotide base sequence selected from the group consisting of:

SEQ ID NO: 8: CGTTAAGCAT CTAGATTTAA TACCAAACTT ACAAACCCG,

SEQ ID NO: 10: GCCTTCGCCA CCGGTGTTCT TCCATATATC TA,

SEQ ID NO: 37: CGUUAAGCAU CUAGAUUUAA UACCAAACUU ACAAACCCG,

SEQ ID NO: 38: CGGGTTTGTA AGTTTGGTAT TAAATCTAGA TGCTTAACG,

SEQ ID NO: 39: CGGGUUUGUA AGUUUGGUAU UAAAUCUAGA UGCUUAACG,

SEQ ID NO: 79: GCCUUCGCCA CCGGUGUUCU UCCAUAUAUC UA,

SEQ ID NO: 80: TAGATATATG GAAGAACACC GGTGGCGAAG GC, and

SEQ ID NO: 81: UAGAUAUAUG GAAGAACACC GGUGGCGAAG GC.

66. The method of claim 58, wherein said hybridization assay probe comprises a detection nucleotide base sequence selected from the group consisting of SEQ ID NO: 11, SEQ ID NO: 43, SEQ ID NO: 44, and SEQ ID NO: 45.

67. The method of claim 66, wherein said method uses one or more helper probes consisting of a nucleotide base sequence selected from the group consisting of:

SEQ ID NO: 10: GCCTTCGCCA CCGGTGTTCT TCCATATATC TA,

SEQ ID NO: 12: CTAATCCTAT TTGCTCCCCA CACTTTCGAG CCTAAGC,

SEQ ID NO: 79: GCCUUCGCCA CCGGUGUUCU UCCAUAUAUC UA,

SEQ ID NO: 80: TAGATATATG GAAGAACACC GGTGGCGAAG GC,

SEQ ID NO: 81: UAGAUAUAUG GAAGAACACC GGUGGCGAAG GC,

SEQ ID NO: 82: CUAAUCCUAU UUGCUCCCCA CACUUUCGAG CCUAAGC,

SEQ ID NO: 83: GCTTAGGCTC GAAAGTGTGG GGAGCAAATA GGATTAG, and

SEQ ID NO: 84: GCUUAGGCUC GAAAGUGUGG GGAGCAAAUA GGAUUAG.

68. The method of claim 58, wherein said hybridization assay probe comprises a detection nucleotide base sequence selected from the group consisting of SEQ ID NO: 20, SEQ ID NO: 52, SEQ ID NO: 53, and SEQ ID NO: 54.

69. The method of claim 68, wherein said method uses one or more helper probes consisting of a nucleotide base sequence selected from the group consisting of:

SEQ ID NO: 19: TAGCACGTTT GCAGCCCTAG ATATAAGGGG CATGATG,

SEQ ID NO: 21: CGAATTGCAG CCCTCTATCC GAACTGAGAC TAACTTTTTC TG,

SEQ ID NO: 97: UAGCACGUUU GCAGCCCUAG AUAUAAGGGG CAUGAUG,

SEQ ID NO: 98: CATCATGCCC CTTATATCTA GGGCTGCAAA CGTGCTA,

SEQ ID NO: 99: CAUCAUGCCC CUUAUAUCUA GGGCUGCAAA CGUGCUA,

SEQ ID NO: 100: CGAAUUGCAG CCCUCUAUCC GAACUGAGAC UAACUUUUUC UG,

SEQ ID NO: 101: CAGAAAAAGT TAGTCTCAGT TCGGATAGAG GGCTGCAATT CG, and,

SEQ ID NO: 102: CAGAAAAAGU UAGUCUCAGU UCGGAUAGAG GGCUGCAAUU CG.

70. The method of claim 58, wherein said hybridization assay probe comprises a detection nucleotide base sequence selected from the group consisting of SEQ ID NO: 22, SEQ ID NO: 55, SEQ ID NO: 56, and SEQ ID NO: 57.

71. The method of claim 70, wherein said method uses one or more helper probes consisting of a nucleotide base sequence selected from the group consisting of:

SEQ ID NO: 24: GGAACAGGTA TTTCCACTCT GATATGATCA CTAC,

SEQ ID NO: 25: GCGTAGCGAT GACCTATTTT ACTTGC,

SEQ ID NO: 103: GGAACAGGUA UUUCCACUCU GAUAUGAUCA CUAC,

SEQ ID NO: 104: GTAGTGATCA TATCAGAGTG GAAATACCTG TTCC,

SEQ ID NO: 105: GUAGUGAUCA UAUCAGAGUG GAAAUACCUG UUCC,

SEQ ID NO: 106: GCGUAGCGAU GACCUAUUUU ACUUGC,

SEQ ID NO: 107: GCAAGTAAAA TAGGTCATCG CTACGC, and

SEQ ID NO: 108: GCAAGUAAAA UAGGUCAUCG CUACGC.

72. The method of claim 58, wherein said hybridization assay probe comprises a detection nucleotide base sequence selected from the group consisting of SEQ ID NO: 23, SEQ ID NO: 58, SEQ ID NO: 59, and SEQ ID NO: 60.

73. The method of claim 72, wherein said method uses one or more helper probes consisting of a nucleotide base sequence selected from the group consisting of:

SEQ ID NO: 26: GGATGGGAAC AGGTATTTCC ACTCTGATAT GATCAC,

SEQ ID NO: 27: GCGTAGCGAT GACCTATTTT ACTGCGCTA TTTT,

SEQ ID NO: 109: GGAUGGGAAC AGGUAUUCC ACUCUGAUAU GAUCAC,

SEQ ID NO: 110: GTGATCATAT CAGAGTGGAA ATACCTGTTC CCATCC,

SEQ ID NO: 111: GUGAUCAUAU CAGAGUGGAA AUACCUGUUC CCAUCC,

SEQ ID NO: 112: GCGUAGCGAU GACCUAUUUU ACUUGCGCUA UUUU,

SEQ ID NO: 113: AAAATAGCGC AAGTAAAATA GGTCATCGCT ACGC, and

SEQ ID NO: 114: AAAAUAGCGC AAGUAAAAUA GGUCAUCGCU ACGC.

74. The method of claim 58, wherein said hybridization assay probe comprises a detection nucleotide base sequence selected from the group consisting of SEQ ID NO: 29, SEQ ID NO: 61, SEQ ID NO: 62, and SEQ ID NO: 63.

75. The method of claim 74, wherein said method uses one or more helper probes consisting of a nucleotide base sequence selected from the group consisting of:

SEQ ID NO: 28: GAGATCAACG GATTAAAGCC TCTTATCAGC TACCCGTTGC TTATCGCAGA TTAGCACG,

SEQ ID NO: 30: CACTTCACCA GGTATCGCTC TGTTAAACTA TGAATTCATT TATA,

SEQ ID NO: 115: GAGAUCAACG GAUUAAGCC UCUUAUCAGC UACCCGUUGC UUAUCGCAGA UUAGCACG,

SEQ ID NO: 116: CGTGCTAATC TGCGATAAGC AACGGGTAGC TGATAAGAGG CTTTAATCCG TTGATCTC,

SEQ ID NO: 117: CGUGCUAAUC UGCGAUAAGC AACGGGUAGC UGAUAAGAGG CUUUAAUCCG UUGAUCUC,

SEQ ID NO: 118: CACUUCACCA GGUAUCGCUC UGUUAAACUA UGAAUUCAUU UAUA,

SEQ ID NO: 119: TATAAATGAA TTCATAGTTT AACAGAGCGA TACCTGGTGA AGTG, and

SEQ ID NO: 120: UAUAAAUGAA UUCAUAGUUU AACAGAGCGA UACCUGGUGA AGUG.

76. The method of claim 58, wherein said hybridization assay probe comprises a detection nucleotide base sequence selected from the group consisting of SEQ ID NO: 26, SEQ ID NO: 109, SEQ ID NO: 110, and SEQ ID NO: 111.

77. The method of any one of claims 59, 60, and 61–76, wherein said hybridization assay probe consists of said detection nucleotide base sequence and one or more reporter groups.

78. A method for specifically detecting the presence of *Ureaplasma urealyticum* biotype 1 or *Ureaplasma urealyticum* biotype 2 comprising the steps of:

a) contacting a sample with a hybridization assay probe able to hybridize under stringent hybridization assay conditions to a *Ureaplasma urealyticum* biotype specific target nucleic acid sequence to form a probe:target hybrid with either *Ureaplasma urealyticum* biotype 1 or *Ureaplasma urealyticum* biotype 2 nucleic acid, wherein said hybridization assay probe does not hybridize to nucleic acid from both *Ureaplasma urealyticum* biotype 1 and *Ureaplasma urealyticum* biotype 2 under said stringent hybridization assay conditions to form a detectable probe:non-target hybrid, said *Ureaplasma urealyticum* biotype specific target nucleic acid sequence being selected from the group consisting of:

SEQ ID NO: 126: CAACACCGAC UCGUUCGAGC,
SEQ ID NO: 127: CAACACCGAC CCAUUCGG,
SEQ ID NO: 136: GCUCGAACGA GUCGGUGUUG, and
SEQ ID NO: 137: CCGAAUGGGU CGGUGUUG;

provided that under said stringent hybridization conditions said probe does not hybridize to nucleic acid from *Mycoplasma genitalium*, *Mycoplasma hominis* and *Mycoplasma pneumoniae* to form a detectable probe:non-target hybrid; and b) employing said stringent hybridization assay conditions and detecting the presence of said detectable probe:target hybrid formed under said stringent hybridization assay conditions as an indication of the presence of *Ureaplasma urealyticum* biotype 1 or *Ureaplasma urealyticum* biotype 2.

79. The method of claim 78, wherein said target nucleic acid sequence is either SEQ ID NO: 126 or SEQ ID NO: 136.

80. The method of claim 78, wherein said target nucleic acid sequence is either SEQ ID NO: 127 or SEQ ID NO: 137.

81. A method for specifically detecting the presence of *Ureaplasma urealyticum* biotype 1 or *Ureaplasma urealyticum* biotype 2 comprising the steps of:

a) contacting a sample with a hybridization assay probe able to hybridize under stringent hybridization assay conditions with either *Ureaplasma urealyticum* biotype 1 or *Ureaplasma urealyticum* biotype 2 nucleic acid to form a detectable probe:target hybrid, wherein said hybridization assay probe does not hybridize to nucleic acid from both *Ureaplasma urealyticum* biotype 1 and *Ureaplasma urealyticum* biotype 2 under said stringent hybridization assay conditions to form said detectable probe:non-target hybrid, said hybridization assay probe comprising a detection nucleotide base sequence selected from the group consisting of:
SEQ ID NO: 121: CAACACCGAC TCGTTCGAGC,
SEQ ID NO: 122: CAACACCGAC CCATTCGG,
SEQ ID NO: 126: CAACACCGAC UCGUUCGAGC,
SEQ ID NO: 127: CAACACCGAC CCAUUCGG,
SEQ ID NO: 131: GCTCGAACGA GTCGGTGTTG,
SEQ ID NO: 132: CCGAATGGGT CGGTGTTG,
SEQ ID NO: 136: GCUCGAACGA GUCGGUGUUG, and
SEQ ID NO: 137: CCGAAUGGGU CGGUGUUG;
provided that under said stringent hybridization conditions said probe does not hybridize to nucleic acid from *Mycoplasma genitalium, Mycoplasma hominis* and *Mycoplasma pneumoniae* to form a detectable probe:non-target hybrid; and b) employing said stringent hybridization assay conditions and detecting the presence of said detectable probe:target hybrid formed under said stringent hybridization assay conditions as an indication of the presence of either *Ureaplasma urealyticum* biotype 1 or *Ureaplasma urealyticum* biotype 2.

82. The method of claim 81, wherein said hybridization assay probe comprises a detection nucleotide base sequence selected from the group consisting of:
SEQ ID NO: 121: CAACACCGAC TCGTTCGAGC,
SEQ ID NO: 126: CAACACCGAC UCGUUCGAGC,
SEQ ID NO: 131: GCTCGAACGA GTCGGTGTTG, and
SEQ ID NO: 136: GCUCGAACGA GUCGGUGUUG.

83. The method of claim 82, further comprising the use of a helper probe consisting of a sequence selected from the group consisting of:
SEQ ID NO: 123: CGACATTTAA TGATGATCGT TTACGGTGTG GAC,
SEQ ID NO: 125: CCCAGGCACA TCATTTAATG CGTTAGCTA,
SEQ ID NO: 128: CGACAUUUAA UGAUGAUCGU UUACGGUGUG GAC,
SEQ ID NO: 130: CCCAGGCACA UCAUUUAAUG CGUUAGCUA,
SEQ ID NO: 133: GTCCACACCG TAAACGATCA TCATTAAATG TCG,
SEQ ID NO: 135: TAGCTAACGC ATTAAATGAT GTGCCTGGG,
SEQ ID NO: 138: GUCCACACCG UAAACGAUCA UCAUUAAAUG UCG, and
SEQ ID NO: 140: UAGCUAACGC AUUAAAUGAU GUGCCUGGG.

84. The method of claim 81, wherein said hybridization assay probe comprises a detection nucleotide base sequence selected from the group consisting of:
SEQ ID NO: 122: CAACACCGAC CCATTCGG,
SEQ ID NO: 127: CAACACCGAC CCAUUCGG,
SEQ ID NO: 132: CCGAATGGGT CGGTGTTG, and
SEQ ID NO: 137: CCGAAUGGGU CGGUGUUG.

85. The method of claim 84, further comprising the use of a helper probe in said step (a), said helper probe consisting of a sequence selected from the group consisting of:
SEQ ID NO: 124: GCCGACATTT AATGATGATC GTT-TACGGTG TGGAC,
SEQ ID NO: 125: CCCAGGCACA TCATTTAATG CGTTAGCTA,
SEQ ID NO: 129: GCCGACAUUU AAUGAUGAUC GUUUACGGUG UGGAC,
SEQ ID NO: 130: CCCAGGCACA UCAUUUAAUG CGUUAGCUA,
SEQ ID NO: 134: GTCCACACCG TAAACGATCA TCATTAAATG TCGGC,
SEQ ID NO: 135: TAGCTAACGC ATTAAATGAT GTGCCTGGG,
SEQ ID NO: 139: GUCCACACCG UAAACGAUCA UCAUUAAAUG UCGGC, and
SEQ ID NO: 140: UAGCUAACGC AUUAAAUGAU GUGCCUGGG.

86. The method of any one of claims 82–85, wherein said hybridization assay probe consists of one or more reporter groups and said detection nucleotide base sequence.

87. A method for detecting the presence of Ureaplasma in a sample and distinguishing said Ureaplasma from *Mycoplasma genitalium, Mycoplasma pneumoniae,* and *Mycoplasma hominis,* comprising the steps of:
a) providing to said sample a hybridization assay probe comprising a nucleotide base sequence selected from the group consisting of
SEQ ID NO: 14: CGTTCGAGCC GACATTTAAT GATGATCG,
SEQ ID NO: 46: CGUUCGAGCC GACAUUUAAU GAUGAUCG,
SEQ ID NO: 47: CGATCATCAT TAAATGTCGG CTCGAACG, and
SEQ ID NO: 48: CGAUCAUCAU UAAAUGUCGG CUCGAACG; wherein under stringent hybridization assay conditions said hybridization assay probe forms a detectable probe:target hybrid with *Ureaplasma urealyticum* nucleic acid, but not with nucleic acid from *Mycoplasma genitalium, Mycoplasma hominis* and *Mycoplasma pneumoniae;* and
a helper probe consisting of a nucleotide base sequence selected from the group consisting of:
SEQ ID NO: 13: TTTACGGTGT GGACTACTAG GGTAT,
SEQ ID NO: 15: GCGTTAGCTA CAACACCGAC T,
SEQ ID NO: 85: UUUACGGUGU GGACUACUAG GGUAU,
SEQ ID NO: 86: ATACCCTAGT AGTCCACACC GTAAA,
SEQ ID NO: 87: AUACCCUAGU AGUCCACACC GUAAA,
SEQ ID NO: 88: GCGUUAGCUA CAACACCGAC U,
SEQ ID NO: 89: AGTCGGTGTT GTAGCTAACG C, and
SEQ ID NO: 90: AGUCGGUGUU GUAGCUAACG C; and b) employing said stringent hybridization assay conditions and detecting the presence of said detectable probe:target hybrid formed under stringent hybridization assay conditions as an indication that Ureaplasma may be present in said sample.

88. The method of claim 87, wherein said hybridization assay probe consists of one or more reporter groups and a nucleotide base sequence selected from the group consisting of SEQ ID NO: 14, SEQ ID NO: 46, SEQ ID NO: 47, and SEQ ID NO: 48.

89. A method for detecting the presence of Ureaplasma in a sample and distinguishing said Ureaplasma from *Mycoplasma genitalium, Mycoplasma pneumoniae,* and *Mycoplasma hominis* comprising the steps of:
a) providing to said sample a hybridization assay probe comprising a nucleotide base sequence selected from the group consisting of

SEQ ID NO: 17: GCGTCGCAAT AGATGTCAAA CCTAG,

SEQ ID NO: 49: GCGUCGCAAU AGAUGUCAAA CCUAG,

SEQ ID NO: 50: CTAGGTTTGA CATCTATTGC GACGC, and

SEQ ID NO: 51: CUAGGUUUGA CAUCUAUUGC GACGC; wherein under stringent hybridization assay conditions said hybridization assay probe forms a detectable probe:target hybrid with *Ureaplasma urealyticum* nucleic acid, but not with nucleic acid from *Mycoplasma genitalium, Mycoplasma hominis* and *Mycoplasma pneumoniae;* and a helper probe consisting of a nucleotide base sequence selected from the group consisting of:

SEQ ID NO: 16: GTAAGGTTCT ACGTGTATTG TCAAATTAAG CAACATGCTC CACCAC,

SEQ ID NO: 18: CGACAACCAT GCACCACCTG TCATATTGTT AACCTCAAC,

SEQ ID NO: 91: GUAAGGUUCU ACGUGUAUUG UCAAAUUAAG CAACAUGCUC CACCAC,

SEQ ID NO: 92: GTGGTGGAGC ATGTTGCTTA ATTTGACAAT ACACGTAGAA CCTTAC,

SEQ ID NO: 93: GUGGUGGAGC AUGUUGCUUA AUUUGACAAU ACACGUAGAA CCUUAC,

SEQ ID NO: 94: CGACAACCAU GCACCACCUG UCAUAUUGUU AACCUCAAC,

SEQ ID NO: 95: GTTGAGGTTA ACAATATGAC AGGTGGTGCA TGGTTGTCG, and

SEQ ID NO: 96: GUUGAGGUUA ACAAUAUGAC AGGUGGUGCA UGGUUGUCG; and b) employing said stringent hybridization assay conditions and detecting the presence of said detectable probe:target hybrid formed under stringent hybridization assay conditions as an indication that Ureaplasma may be present in said sample.

90. The method of claim 89, wherein said hybridization assay probe consists of one or more reporter groups and a nucleotide base sequence selected from the group consisting of SEQ ID NO: 17, SEQ ID NO: 49, SEQ ID NO: 50, and SEQ ID NO: 51.

91. A hybridization assay probe 10 to 50 nucleotides in length comprising an oligonucleotide sufficiently complementary to a Ureaplasma urealyticum target nucleic acid sequence to form a detectable probe:target hybrid with said *Ureaplasma urealyticum* target nucleic acid sequence under stringent hybridization assay conditions, wherein said *Ureaplasma urealyticum* target nucleic acid sequence is selected from the group consisting of:

SEQ ID NO: 31: ACCUCUCAGU ACAGCUACGC G,

SEQ ID NO: 33: CGCGUAGCUG UACUGAGAGG U,

SEQ ID NO: 37: CGUUAAGCAU CUAGAUUUAA UACCAAACUU ACAAACCCG,

SEQ ID NO: 39: CGGGUUUGUA AGUUUGGUAU UAAAUCUAGA UGCUUAACG,

SEQ ID NO: 40: CCUACUACAC UCUAGGUUUA CAGUUUUUGA UACAGCUAGA,

SEQ ID NO: 42: UCUAGCUGUA UCAAAAACUG UAAACCUAGA GUGUAGUAGG,

SEQ ID NO: 43: GUCAGUGAUA GUCCAAGUUG GC,

SEQ ID NO: 45: GCCAACUUUG ACUAUCACUG AC,

SEQ ID NO: 55: GCUAUUUUCG GCUCUAGAGU GCUUUGACUU CUGUUCGGG AUG,

SEQ ID NO: 57: CAUCCCGAAC ACAGAAGUCA AGCACUCUAG AGCCGAAAAU AGC,

SEQ ID NO: 58: CGGCUCUAGA GUGCUUGACU UCUGUGUUCG,

SEQ ID NO: 60: CGAACACAGA AGUCAAGCAC UCUAGAGCCG,

SEQ ID NO: 61: CAGUAAUCUA AUUCUCAUUA GACUGAGUUU CCUCAUUUCG,

SEQ ID NO: 63: CGAAUGAGGA AACUCAGUCU AAUGAGAAUU AGAUUACUG,

SEQ ID NO: 109: GGAUGGGAAC AGGUAUUUCC ACUCUGAUAU GAUCAC, and

SEQ ID NO 111: GUGAUCAUAU CAGAGUGGAA AUACCUGUCC CCAUCC;

wherein under said stringent hybridization assay conditions said hybridization assay probe does not form a detectable probe:non-target hybrid with nucleic acid from *Mycoplasma hominis.*

92. The hybridization assay probe of claim 91, wherein said hybridization assay probe also does not form said detectable probe:non-target hybrid with nucleic acid from *Mycoplasma genitalium* and *Mycoplasma pneumoniae.*

93. The hybridization assay probe of claim 91, wherein said hybridization assay probe also does not form said detectable probe:non target hybrid with nucleic acid from *Mycoplasma orale, Mycoplasma fermentans, Mycoplasma capricolum, Mycoplasma lipophilum,* and *Mycoplasma salivarium.*

94. The hybridization assay probe of claim 91, wherein said target *Ureaplasma urealyticum* nucleic acid sequence is selected from the group consisting of SEQ ID NO: 31 and SEQ ID NO: 33.

95. The hybridization assay probe of claim 91, wherein said target Ureaplasma urealyticum nucleic acid sequence is selected from the group consisting of SEQ ID NO: 37 and SEQ ID NO: 39.

96. The hybridization assay probe of claim 91, wherein said target *Ureaplasma urealyticum* nucleic acid sequence is selected from the group consisting of SEQ ID NO: 40 and SEQ ID NO: 42.

97. The hybridization assay probe of claim 91, wherein said target *Ureaplasma urealyticum* nucleic acid sequence is selected from the group consisting of SEQ ID NO: 43 and SEQ ID NO: 45.

98. The hybridization assay probe of claim 91, wherein said target *Ureaplasma urealyticum* nucleic acid sequence is selected from the group consisting of SEQ ID NO: 55 and SEQ ID NO: 57.

99. The hybridization assay probe of claim 91, wherein said target *Ureaplasma urealyticum* nucleic acid sequence is selected from the group consisting of SEQ ID NO: 58 and SEQ ID NO: 60.

100. The hybridization assay probe of claim 91, wherein said target *Ureaplasma urealyticum* nucleic acid sequence is selected from the group consisting of SEQ ID NO: 61 and SEQ ID NO: 63.

101. The hybridization assay probe of claim 91, wherein said target *Ureaplasma urealyticum* nucleic acid sequence is selected from the group consisting of SEQ ID NO: 109 and SEQ ID NO: 111.

102. A probe mix comprising:

a) a hybridization assay probe for detecting Ureaplasma under stringent hybridization assay conditions which is 10 to 50 nucleotides in length and comprises a nucleotide base sequence selected from the group consisting of

SEQ ID NO: 2: ACCTCTCAGT ACAGCTACGC G,

SEQ ID NO: 8: CGTTAAGCAT CTAGATTTAA TAC-CAAACTT ACAAACCCG,

SEQ ID NO: 9: CCTACTACAC TCTAGGTTTA CAGTTTTTGA TACAGCTAGA,

SEQ ID NO: 11: GTCAGTGATA GTCCAAGTTG GC,

SEQ ID NO: 20: CGATTTTGCA GCAGTTTGTA TTAGCCATTG,

SEQ ID NO: 22: GCTATTTTCG GCTCTAGAGT GCTTGACTTC TGTGTTCGGG ATG,

SEQ ID NO: 23: CGGCTCTAGA GTGCTTGACT TCTGTGTTCG,

SEQ ID NO: 26: GGATGGGAAC AGGTATTTCC ACTCTGATAT GATCAC,

SEQ ID NO: 29: CAGTAATCTA ATTCTCATTA GACTGAGTTT CCTCATTCG,

SEQ ID NO: 31: ACCUCUCAGU ACAGCUACGC G,

SEQ ID NO: 32: CGCGTAGCTG TACTGAGAGG T,

SEQ ID NO: 33: CGCGUAGCUG UACUGAGAGG U,

SEQ ID NO: 37: CGUUAAGCAU CUAGAUUUAA UACCAAACUU ACAAACCCG,

SEQ ID NO: 38: CGGGTTTGTA AGTTTGGTAT TAAATCTAGA TGCTTAACG,

SEQ ID NO: 39: CGGGUUUGUA AGUUUGGUAU UAAAUCUAGA UGCUUAACG,

SEQ ID NO: 40: CCUACUACAC UCUAGGUUUA CAGUUUUUGA UACAGCUAGA,

SEQ ID NO: 41: TCTAGCTGTA TCAAAAACTG TAAACCTAGA GTGTAGTAGG,

SEQ ID NO: 42: UCUAGCUGUA UCAAAAACUG UAAACCUAGA GUGUAGUAGG,

SEQ ID NO: 43: GUCAGUGAUA GUCCAAGUUG GC,

SEQ ID NO: 44: GCCAACTTGG ACTATCACTG AC,

SEQ ID NO: 45: GCCAACUUGG ACUAUCACUG AC,

SEQ ID NO: 52: CGAUUUUGCA GCAGUUUGUA UUAGCCAUUG,

SEQ ID NO: 53: CAATGGCTAA TACAAACTGC TGCAAAATCG,

SEQ ID NO: 54: CAAUGGCUAA UACAAACUGC UGCAAAAUCG,

SEQ ID NO: 55: GCUAUUUUCG GCUCUAGAGU GCUUGACUUC UGUGUUCGGG AUG,

SEQ ID NO: 56: CATCCCGAAC ACAGAAGTCA AGCACTCTAG AGCCGAAAAT AGC,

SEQ ID NO: 57: CAUCCCGAAC ACAGAAGUCA AGCACUCUAG AGCCGAAAAU AGC,

SEQ ID NO: 58: CGGCUCUAGA GUGCUUGACU UCUGUGUUCG,

SEQ ID NO: 59: CGAACACAGA AGTCAAGCAC TCTAGAGCCG,

SEQ ID NO: 60: CGAACACAGA AGUCAAGCAC UCUAGAGCCG,

SEQ ID NO: 61: CAGUAAUCUA AUUCUCAUUA GACUGAGUUU CCUCAUUUCG,

SEQ ID NO; 62: CGAATGAGGA AACTCAGTCT AATGAGAATT AGATTACTG,

SEQ ID NO: 63: CGAAUGAGGA AACUCAGUCU AAUGAGAAUU AGAUUACUG,

SEQ ID NO: 109: GGAUUGGGAAC AGGUAUUCC ACUCUGAUAU GAUCAC,

SEQ ID NO: 110: GTGATCATAT CAGAGTGGAA ATACCTGTTC CCATCC, and

SEQ ID NO: 111: GUGAUCAUAU CAGAGUGGAA. AUACCGUUC CCAUCC;

wherein under stringent hybridization assay conditions said hybridization assay probe forms a detectable probe:target hybrid with *Ureaplasma urealyticum* nucleic acid, but does not form a detectable probe:non-target hybrid with nucleic acid from *Mycoplasma genitalium, Mycoplasma hominis* and *Mycoplasma pneumoniae* under said stringent hybridization assay conditions; and b) a helper probe.

103. The probe mix of claim 102, wherein said hybridization assay probe comprises a nucleotide base sequence selected from the group consisting of SEQ ID NO: 22, SEQ ID NO: 55, SEQ ID NO: 56, and SEQ ID NO: 57, and said helper probe comprises a nucleotide base sequence selected from the group consisting of:

SEQ ID NO: 24: GGAACAGGTA TTTCCACTCT GATATGATCA CTAC,

SEQ ID NO: 25: GCGTAGCGAT GACCTATTTT ACTTGC,

SEQ ID NO: 103: GGAACAGGUA UUUCCACUCU GAUAUGAUCA CUAC,

SEQ ID NO: 104: GTAGTGATCA TATCAGAGTG GAAATACCTG TTCC,

SEQ ID NO: 105: GUAGUGAUCA UAUCAGAGUG GAAAUACCUG UUCC,

SEQ ID NO: 106: GCGUAGCGAU GACCUAUUUU ACUUGC,

SEQ ID NO: 107: GCAAGTAAAA TAGGTCATCG CTACGC, and

SEQ ID NO: 108: GCAAGUAAAA UAGGUCAUCG CUACGC.

104. The probe mix of claim 103, wherein said probe mix is selected from the group consisting of:

(a) a probe mix comprising:

a hybridization assay probe consisting of one or more reporter groups and the nucleotide base sequence of either SEQ ID NO: 22 or SEQ ID NO: 55;

a first helper probe consisting of the nucleotide base sequence of either SEQ ID NO: 24 or SEQ ID NO: 103; and a second helper probe consisting of the nucleotide base sequence of either SEQ ID NO: 25 or SEQ ID NO: 106; and (b) a probe mix comprising:

a hybridization assay probe consisting of one or more reporter groups and the nucleotide base sequence of either SEQ ID NO: 56 or SEQ ID NO: 57;

a first helper probe consisting of the nucleotide base sequence of either SEQ ID NO: 104 or SEQ ID NO. 105; and a second helper probe consisting of the nucleotide base sequence of either SEQ ID NO: 107 or SEQ ID NO: 108.

105. The probe mix of claim 102, wherein said hybridization assay probe comprises a nucleotide base sequence selected from the group consisting of SEQ ID NO: 23, SEQ ID NO: 58, SEQ ID NO: 59, and SEQ ID NO: 60, and said helper probe comprises a nucleotide base sequence selected from the group consisting of

SEQ ID NO: 26: GGATGGGAAC AGGTATTTCC ACTCTGATAT GATCAC,

SEQ ID NO: 27: GCGTAGCGAT GACCTATTTT ACTGCGCTA TTTT,

SEQ ID NO: 109: GGAUGGGAAC AGGUAUUUCC ACUCUGAUAU GAUCAC,

SEQ ID NO: 110: GTGATCATAT CAGAGTGGAA ATACCTGTTC CCATCC,

SEQ ID NO: 111: GUGAUCAUAU CAGAGUGGAA AUACCUGUUC CCAUCC,

SEQ ID NO: 112: GCGUAGCGAU GACCUAULUU ACUUGCGCUA UUU,

SEQ ID NO: 113: AAAATAGCGC AAGTAAAATA GGTCATCGCT ACGC, and

SEQ ID NO: 114: AAAAUAGCGC AAGUAAAAUA, GGUCAUCGCU ACGC.

106. The probe mix of claim 105, wherein said probe mix is selected from the group consisting of:

(a) a probe mix comprising:
a hybridization assay probe consisting of one or more reporter groups and the nucleotide base sequence of either SEQ ID NO: 23 or SEQ ID NO: 58;
a first helper probe consisting of the nucleotide base sequence of either SEQ ID NO: 26 or SEQ ID NO: 109; and
a second helper probe consisting of the nucleotide base sequence of either SEQ ID NO: 27 or SEQ ID NO: 112; and (a) a probe mix comprising:
a hybridization assay probe consisting of one or more reporter groups and the nucleotide base sequence of either SEQ ID NO: 59 or SEQ ID NO: 60;
a first helper probe consisting of the nucleotide base sequence of either SEQ ID NO: 110 or SEQ IDNO: 111; and
a second helper probe consisting of the nucleotide base sequence of either SEQ ID NO: 113 or SEQ ID NO: 114.

107. A hybridization assay probe 10 to 100 nucleotides in length comprising an oligonucleotide sufficiently complementary to a *Ureaplasma urealyticum* target nucleic acid sequence to form a detectable probe:target hybrid with said *Ureaplasma urealyticum* target nucleic acid sequence under stringent hybridization assay conditions, wherein said *Ureaplasma urealyticum* target nucleic acid sequence is SEQ ID NO: 54: CAAUGGCUAA UACAAACUGC UGCAAAAUCG, and said hybridization assay probe targets at least one nucleotide 5' to "A" at nucleotide position 11 in SEQ ID NO: 54, wherein under said stringent hybridization assay conditions said hybridization assay probe does not form a detectable probe:non-target hybrid with nucleic acid from *Mycoplasma hominis*.

* * * * *